(12) United States Patent
Macary et al.

(10) Patent No.: US 10,923,226 B2
(45) Date of Patent: Feb. 16, 2021

(54) SYSTEMS, METHODS AND ARTICLES FOR MONITORING AND ENHANCING HUMAN WELLNESS

(71) Applicant: DELOS LIVING LLC, New York, NY (US)

(72) Inventors: Richard A. Macary, New York, NY (US); Shaun B. Stewart, New York, NY (US); Dana S. Pillai, New York, NY (US)

(73) Assignee: Delos Living LLC, New York, NY (US)

( * ) Notice: Subject to any disclaimer, the term of this patent is extended or adjusted under 35 U.S.C. 154(b) by 308 days.

(21) Appl. No.: 15/543,114

(22) PCT Filed: Jan. 13, 2016

(86) PCT No.: PCT/US2016/013215
§ 371 (c)(1),
(2) Date: Jul. 12, 2017

(87) PCT Pub. No.: WO2016/115230
PCT Pub. Date: Jul. 21, 2016

(65) Prior Publication Data
US 2018/0330811 A1    Nov. 15, 2018

Related U.S. Application Data

(60) Provisional application No. 62/102,963, filed on Jan. 13, 2015.

(51) Int. Cl.
*G16H 20/70* (2018.01)
*G09B 19/00* (2006.01)
(Continued)

(52) U.S. Cl.
CPC .......... *G16H 20/70* (2018.01); *A61M 21/02* (2013.01); *G06F 19/3481* (2013.01);
(Continued)

(58) Field of Classification Search
None
See application file for complete search history.

(56) References Cited

U.S. PATENT DOCUMENTS

| 628,351 A | 7/1899 | O'Neill |
| 828,733 A | 8/1906 | Fuller |

(Continued)

FOREIGN PATENT DOCUMENTS

| CA | 2 307 458 A1 | 11/2001 |
| CA | 2 740 939 A1 | 3/2010 |

(Continued)

OTHER PUBLICATIONS

Allergy Buyers Club, "Philips Wake up Light Dawn Simulators Alarm Clocks," retrieved from http://www.allergybuyersclub.com/philips-wake-up-light-dawn-simulator-alarm-clocks.html, retrieved on Aug. 13, 2012, 2 pages.

(Continued)

*Primary Examiner* — James B Hull
(74) *Attorney, Agent, or Firm* — Fitch, Even, Tabin & Flannery LLP

(57) ABSTRACT

Wellness monitoring systems and methods that account for both environmental characteristics of habitable environments (e.g., hotel or motel rooms, spas, resorts, cruise boat cabins, offices, hospitals and/or homes, apartments or residences) and biometric feedback. The wellness monitoring systems collect data from a plurality of environmental sensors in one or more habitable environments and collect data from a plurality of body worn sensors. The wellness monitoring systems analyze the collected data to generate (Continued)

reports and/or prompt individuals to take action or complete an activity.

17 Claims, 12 Drawing Sheets

(51) Int. Cl.
<table>
<tr><td>G16H 40/63</td><td>(2018.01)</td></tr>
<tr><td>G06Q 10/06</td><td>(2012.01)</td></tr>
<tr><td>G06F 19/00</td><td>(2018.01)</td></tr>
<tr><td>G06Q 50/12</td><td>(2012.01)</td></tr>
<tr><td>A61M 21/02</td><td>(2006.01)</td></tr>
<tr><td>G06Q 50/22</td><td>(2018.01)</td></tr>
<tr><td>A61M 21/00</td><td>(2006.01)</td></tr>
</table>

(52) U.S. Cl.
CPC ......... *G06Q 10/0639* (2013.01); *G06Q 50/12* (2013.01); *G16H 40/63* (2018.01); *A61M 2021/0011* (2013.01); *A61M 2021/0016* (2013.01); *A61M 2021/0027* (2013.01); *A61M 2021/0044* (2013.01); *A61M 2021/0066* (2013.01); *A61M 2021/0083* (2013.01); *A61M 2205/3303* (2013.01); *A61M 2205/3561* (2013.01); *A61M 2205/50* (2013.01); *G06Q 50/22* (2013.01); *G09B 19/00* (2013.01); *Y02A 90/10* (2018.01)

(56) References Cited

U.S. PATENT DOCUMENTS

| | | | |
|---|---|---|---|
| 853,033 A | 5/1907 | Roberts |
| 1,648,277 A | 11/1927 | Korb |
| 2,184,644 A | 12/1939 | Homberger |
| RE27,027 E | 1/1971 | Cristofv |
| 3,621,838 A | 11/1971 | Harding et al. |
| 3,678,337 A | 7/1972 | Grauvogel |
| 3,782,006 A | 1/1974 | Symmes |
| 4,074,124 A | 2/1978 | Maute |
| 4,273,999 A | 6/1981 | Pierpoint |
| 4,308,911 A | 1/1982 | Mandl |
| 4,638,853 A | 1/1987 | Papak |
| 4,717,343 A | 1/1988 | Densky |
| D295,934 S | 5/1988 | Dyrhood |
| 4,803,625 A | 2/1989 | Fu et al. |
| 4,828,609 A | 5/1989 | Anderson et al. |
| 4,853,854 A | 8/1989 | Behar et al. |
| 4,858,609 A | 8/1989 | Cole |
| 4,882,166 A | 11/1989 | Graham et al. |
| 4,893,291 A | 1/1990 | Bick et al. |
| 4,911,166 A | 3/1990 | Leighton et al. |
| 4,911,737 A | 3/1990 | Yehl et al. |
| 4,916,642 A | 4/1990 | Kaiser |
| 4,930,505 A | 6/1990 | Hatje |
| 4,938,582 A | 7/1990 | Leslie |
| 4,947,928 A | 8/1990 | Parker |
| 4,953,784 A | 9/1990 | Yasufuku |
| 4,962,687 A | 10/1990 | Belliveau et al. |
| D312,018 S | 11/1990 | Giesy |
| 5,006,985 A | 4/1991 | Ehret et al. |
| 5,010,777 A | 4/1991 | Yehl et al. |
| 5,043,840 A | 8/1991 | Yehl et al. |
| 5,079,682 A | 1/1992 | Roberts |
| 5,082,173 A | 1/1992 | Poehlman |
| 5,086,385 A | 2/1992 | Launey |
| 5,092,669 A | 3/1992 | Anderson |
| 5,103,391 A | 4/1992 | Barrett |
| 5,121,030 A | 6/1992 | Schott |
| 5,176,133 A | 1/1993 | Czeisler et al. |
| 5,193,900 A | 3/1993 | Yano et al. |
| 5,197,941 A | 3/1993 | Whitaker |
| 5,207,580 A | 5/1993 | Strecher |
| 5,214,736 A | 5/1993 | Uemiya et al. |
| D335,978 S | 6/1993 | Grahn et al. |
| 5,250,799 A | 10/1993 | Werner |
| 5,259,553 A | 11/1993 | Shyu |
| 5,285,356 A | 2/1994 | Skene |
| 5,285,430 A | 2/1994 | Decker |
| D345,071 S | 3/1994 | Gould |
| 5,292,345 A | 3/1994 | Gerardo |
| 5,304,212 A | 4/1994 | Czeisler et al. |
| 5,343,121 A | 8/1994 | Terman |
| 5,344,068 A | 9/1994 | Haessig |
| 5,350,977 A | 9/1994 | Hamamoto et al. |
| 5,357,170 A | 10/1994 | Luchaco et al. |
| 5,377,258 A | 12/1994 | Bro |
| 5,395,042 A | 3/1995 | Riley et al. |
| 5,433,923 A | 7/1995 | Wolverton et al. |
| 5,462,485 A | 10/1995 | Kinkead |
| D364,762 S | 12/1995 | Compton et al. |
| D365,484 S | 12/1995 | Trattner, Jr. et al. |
| 5,473,537 A | 12/1995 | Glazer et al. |
| 5,503,637 A | 4/1996 | Kyricos et al. |
| 5,545,192 A | 8/1996 | Czeisler et al. |
| 5,589,741 A | 12/1996 | Terman et al. |
| 5,596,994 A | 1/1997 | Bro |
| 5,692,501 A | 12/1997 | Minturn |
| 5,721,471 A | 2/1998 | Begemann et al. |
| 5,722,418 A | 3/1998 | Bro |
| 5,742,516 A | 4/1998 | Olcerst |
| 5,749,365 A | 5/1998 | Magill |
| D396,581 S | 8/1998 | Schubert |
| 5,791,982 A | 8/1998 | Curry et al. |
| 5,805,267 A | 9/1998 | Goldman |
| 5,813,863 A | 9/1998 | Sloane et al. |
| D401,085 S | 11/1998 | Grant |
| 5,833,466 A | 11/1998 | Borg |
| 5,861,717 A | 1/1999 | Begemann |
| 5,892,690 A | 4/1999 | Boatman et al. |
| 5,908,301 A | 6/1999 | Lutz |
| 5,919,217 A | 7/1999 | Hughes |
| 5,937,387 A | 8/1999 | Summerell et al. |
| 5,954,510 A | 9/1999 | Merrill et al. |
| 5,963,294 A | 10/1999 | Schiffer |
| 5,967,789 A | 10/1999 | Segel et al. |
| 6,053,936 A | 4/2000 | Koyama et al. |
| 6,055,480 A | 4/2000 | Nevo et al. |
| D424,356 S | 5/2000 | Hahn |
| 6,118,230 A | 9/2000 | Fleischmann |
| 6,135,970 A | 10/2000 | Kadhiresan et al. |
| 6,166,496 A | 12/2000 | Lys et al. |
| 6,170,318 B1 | 1/2001 | Lewis |
| 6,197,094 B1 | 3/2001 | Thofelt |
| 6,208,905 B1 | 3/2001 | Giddings |
| 6,235,046 B1 | 5/2001 | Gerdt |
| 6,238,337 B1 | 5/2001 | Kambhatla et al. |
| 6,269,339 B1 | 7/2001 | Silver |
| 6,290,140 B1 | 9/2001 | Pesko et al. |
| 6,331,160 B1 | 12/2001 | Bardy |
| 6,340,868 B1 | 1/2002 | Lys et al. |
| 6,344,641 B1 | 2/2002 | Blalock |
| 6,348,867 B1 | 2/2002 | Myllymaki |
| 6,350,275 B1 | 2/2002 | Vreman et al. |
| 6,369,716 B1 | 4/2002 | Abbas |
| 6,387,844 B1 | 5/2002 | Fujishima et al. |
| 6,439,893 B1 | 8/2002 | Byrd et al. |
| 6,441,558 B1 | 8/2002 | Muthu et al. |
| 6,448,550 B1 | 9/2002 | Nishimura |
| 6,448,978 B1 * | 9/2002 | Salvador ................. H04L 67/22 709/204 |
| 6,459,919 B1 | 10/2002 | Lys et al. |
| 6,498,440 B2 | 12/2002 | Stam et al. |
| 6,503,462 B1 | 1/2003 | Michalakos |
| 6,507,159 B2 | 1/2003 | Muthu |
| 6,507,709 B2 | 1/2003 | Hirai et al. |
| 6,525,658 B2 | 2/2003 | Streetman et al. |
| 6,535,190 B2 | 3/2003 | Evanicky |
| 6,554,439 B1 | 4/2003 | Teicher et al. |
| 6,567,009 B2 | 5/2003 | Ohishi et al. |
| 6,582,380 B2 | 6/2003 | Kazlausky et al. |
| 6,583,720 B1 | 6/2003 | Quigley |
| D477,158 S | 7/2003 | Calcerano et al. |

(56) References Cited

U.S. PATENT DOCUMENTS

| | | |
|---|---|---|
| 6,589,912 B2 | 7/2003 | Kawai |
| 6,607,484 B2 | 8/2003 | Suzuki et al. |
| 6,610,127 B2 | 8/2003 | Lu |
| 6,618,723 B1 | 9/2003 | Smith |
| 6,623,512 B1 | 9/2003 | Heller et al. |
| 6,661,798 B2 | 12/2003 | Sano et al. |
| 6,683,419 B2 | 1/2004 | Kriparos |
| 6,691,070 B1 | 2/2004 | Williams et al. |
| 6,711,470 B1 | 3/2004 | Hartenstein |
| 6,720,745 B2 | 4/2004 | Lys et al. |
| 6,727,091 B2 | 4/2004 | Darlington |
| 6,738,551 B2 | 5/2004 | Noda et al. |
| 6,755,783 B2 | 6/2004 | Cosentino et al. |
| 6,756,998 B1 | 6/2004 | Bilger |
| 6,769,915 B2 | 8/2004 | Murgia et al. |
| 6,772,016 B1 | 8/2004 | Örn |
| 6,774,802 B2 | 8/2004 | Bachinski |
| 6,782,351 B2 | 8/2004 | Reichel et al. |
| 6,806,659 B1 | 10/2004 | Mueller et al. |
| 6,834,208 B2 | 12/2004 | Gonzales |
| 6,862,529 B2 | 3/2005 | Brown |
| 6,865,428 B2 | 3/2005 | Gonzales |
| 6,878,191 B2 | 4/2005 | Escaffre et al. |
| 6,879,451 B1 | 4/2005 | Hewlett et al. |
| 6,888,453 B2 | 5/2005 | Lutz et al. |
| 6,888,779 B2 | 5/2005 | Mollicone et al. |
| 6,912,429 B1 | 6/2005 | Bilger |
| 6,923,653 B2 | 8/2005 | Ito |
| 6,933,486 B2 | 8/2005 | Pitigoi-Aron |
| 6,967,565 B2 | 11/2005 | Lingemann |
| 6,991,029 B2 | 1/2006 | Orfield |
| 6,992,803 B2 | 1/2006 | Chang |
| 7,014,336 B1 | 3/2006 | Ducharme et al. |
| 7,038,399 B2 | 5/2006 | Lys et al. |
| 7,065,280 B2 | 6/2006 | Ogawa et al. |
| 7,067,995 B2 | 6/2006 | Gunter et al. |
| D526,512 S | 8/2006 | Hahn |
| 7,092,101 B2 | 8/2006 | Brady et al. |
| 7,097,111 B2 | 8/2006 | Riley et al. |
| 7,099,723 B2 | 8/2006 | Gonzales |
| 7,113,086 B2 | 9/2006 | Shorrock |
| D530,940 S | 10/2006 | Raile |
| 7,145,295 B1 | 12/2006 | Lee et al. |
| 7,145,614 B2 | 12/2006 | Lee et al. |
| 7,173,384 B2 | 2/2007 | Plötz et al. |
| 7,190,126 B1 | 3/2007 | Paton |
| 7,196,619 B2 | 3/2007 | Perlman et al. |
| 7,202,613 B2 | 4/2007 | Morgan |
| 7,213,940 B1 | 5/2007 | Van De Ven et al. |
| 7,215,086 B2 | 5/2007 | Maxik |
| 7,224,282 B2 | 5/2007 | Terauchi et al. |
| 7,256,554 B2 | 8/2007 | Lys |
| 7,260,950 B2 | 8/2007 | Choi |
| 7,274,160 B2 | 9/2007 | Mueller et al. |
| 7,288,902 B1 | 10/2007 | Melanson |
| 7,298,871 B2 | 11/2007 | Lee et al. |
| 7,302,313 B2 | 11/2007 | Sharp et al. |
| 7,308,296 B2 | 12/2007 | Lys et al. |
| 7,319,298 B2 | 1/2008 | Jungwirth et al. |
| 7,324,874 B2 | 1/2008 | Jung |
| 7,327,337 B2 | 2/2008 | Callahan |
| 7,348,949 B2 | 3/2008 | Lee et al. |
| D566,428 S | 4/2008 | Kester |
| 7,354,172 B2 | 4/2008 | Chemel et al. |
| 7,358,679 B2 | 4/2008 | Lys et al. |
| 7,364,583 B2 | 4/2008 | Rose |
| 7,387,405 B2 | 6/2008 | Ducharme et al. |
| 7,415,310 B2 | 8/2008 | Bovee |
| 7,446,303 B2 | 11/2008 | Maniam et al. |
| 7,453,217 B2 | 11/2008 | Lys et al. |
| 7,457,834 B2 | 11/2008 | Jung et al. |
| 7,520,634 B2 | 4/2009 | Ducharme et al. |
| 7,524,279 B2 | 4/2009 | Auphan |
| 7,536,388 B2 | 5/2009 | Jung et al. |
| 7,545,267 B2 | 6/2009 | Stortoni |
| 7,553,039 B2 | 6/2009 | Harris et al. |
| 7,557,521 B2 | 7/2009 | Lys |
| 7,572,028 B2 | 8/2009 | Mueller et al. |
| 7,573,210 B2 | 8/2009 | Ashdown et al. |
| 7,574,320 B2 | 8/2009 | Corwin |
| 7,577,915 B2 | 8/2009 | Hunter |
| 7,624,028 B1 | 11/2009 | Brown |
| 7,647,285 B2 | 1/2010 | Heckerman et al. |
| 7,652,582 B2 | 1/2010 | Littell |
| 7,659,673 B2 | 2/2010 | Lys |
| 7,676,280 B1 | 3/2010 | Bash |
| 7,679,281 B2 | 3/2010 | Kim et al. |
| 7,680,745 B2 | 3/2010 | Hunter |
| 7,689,437 B1 | 3/2010 | Teller et al. |
| 7,725,842 B2 | 5/2010 | Bronkema |
| 7,759,854 B2 | 7/2010 | Miller et al. |
| 7,767,280 B2 | 8/2010 | Klasen-Memmer et al. |
| 7,772,965 B2 | 8/2010 | Farhan et al. |
| 7,827,039 B2 | 11/2010 | Butcher et al. |
| 7,828,205 B2 | 11/2010 | Cronin et al. |
| 7,839,275 B2 | 11/2010 | Spalink et al. |
| 7,840,310 B2 | 11/2010 | Orfield |
| 7,843,353 B2 | 11/2010 | Pan |
| 7,848,945 B2 | 12/2010 | Rozell et al. |
| D632,102 S | 2/2011 | Sato |
| D634,952 S | 3/2011 | Gile |
| 7,901,071 B1 | 3/2011 | Kulas |
| 7,906,789 B2 | 3/2011 | Jung |
| 7,918,406 B2 | 4/2011 | Rosen |
| 7,918,407 B2 | 4/2011 | Patch |
| 7,925,673 B2 | 4/2011 | Beard |
| 7,953,678 B2 | 5/2011 | Hunter |
| 7,967,731 B2 | 6/2011 | Kil |
| 7,973,759 B2 | 7/2011 | Huang et al. |
| 7,977,904 B2 | 7/2011 | Berman et al. |
| 8,028,706 B2 | 10/2011 | Skene et al. |
| 8,038,615 B2 | 10/2011 | Gobeyn et al. |
| 8,064,295 B2 | 11/2011 | Palmer |
| 8,066,405 B2 | 11/2011 | Simon |
| 8,086,407 B2 | 12/2011 | Chan |
| 8,095,153 B2 | 1/2012 | Jenkins et al. |
| 8,100,552 B2 | 1/2012 | Spero |
| 8,100,746 B2 | 1/2012 | Heidel |
| 8,137,108 B2 | 3/2012 | Hamway et al. |
| 8,140,391 B2 | 3/2012 | Jacobi et al. |
| 8,143,792 B2 | 3/2012 | Joo et al. |
| 8,147,302 B2 | 4/2012 | Desrochers |
| 8,150,707 B2 | 4/2012 | Hayet et al. |
| 8,154,398 B2 | 4/2012 | Rolf |
| 8,159,150 B2 | 4/2012 | Ashdown et al. |
| 8,188,873 B2 | 5/2012 | Barth et al. |
| 8,200,744 B2 | 6/2012 | Jung et al. |
| 8,219,115 B1 | 7/2012 | Nelissen |
| 8,226,418 B2 | 7/2012 | Lycas |
| D666,123 S | 8/2012 | Sichello |
| 8,253,349 B2 | 8/2012 | Shteynberg et al. |
| 8,271,575 B2 | 9/2012 | Hunter |
| 8,301,482 B2 | 10/2012 | Reynolds et al. |
| 8,308,784 B2 | 11/2012 | Streeter |
| 8,321,192 B2 | 11/2012 | Boyce et al. |
| 8,344,665 B2 | 1/2013 | Verfuerth |
| 8,352,408 B2 | 1/2013 | Guillama et al. |
| 8,358,214 B2 | 1/2013 | Amigo et al. |
| 8,359,208 B2 | 1/2013 | Slutzky et al. |
| 8,380,359 B2 | 2/2013 | Duchene |
| 8,392,025 B2 | 3/2013 | Orfield |
| 8,429,223 B2 | 4/2013 | Gilley et al. |
| 8,436,556 B2 | 5/2013 | Eisele et al. |
| 8,446,275 B2 | 5/2013 | Utter, II |
| 8,449,300 B2 | 5/2013 | Lycas |
| 8,454,729 B2 | 6/2013 | Mittelmark |
| 8,484,153 B2 | 7/2013 | Mott |
| 8,490,006 B1 | 7/2013 | Reeser |
| 8,497,871 B2 | 7/2013 | Zulch |
| 8,506,612 B2 | 8/2013 | Ashdown |
| 8,508,169 B2 | 8/2013 | Zaharchuk et al. |
| 8,515,785 B2 | 8/2013 | Clark et al. |
| 8,527,213 B2 | 9/2013 | Kailas et al. |
| 8,540,515 B2 | 9/2013 | Williams et al. |

(56) References Cited

U.S. PATENT DOCUMENTS

| | | |
|---|---|---|
| 8,543,244 B2 | 9/2013 | Keeling |
| 8,558,466 B2 | 10/2013 | Curasi et al. |
| 8,558,687 B2 | 10/2013 | Haupt |
| 8,560,344 B2 | 10/2013 | Earles et al. |
| 8,609,121 B2 | 12/2013 | Averett et al. |
| 8,640,038 B1 | 1/2014 | Reeser |
| 8,655,717 B2 | 2/2014 | Schwarzberg et al. |
| 8,660,861 B2 | 2/2014 | Chun et al. |
| 8,666,666 B2 | 3/2014 | Bassa |
| 8,674,842 B2 | 3/2014 | Zishaan |
| 8,690,771 B2 | 4/2014 | Wekell et al. |
| 8,707,619 B2 | 4/2014 | Edwards et al. |
| 8,716,952 B2 | 5/2014 | Van de Ven |
| 8,740,623 B2 | 6/2014 | Walker et al. |
| 8,755,942 B2 | 6/2014 | Bonilla |
| 8,760,370 B2 | 6/2014 | Maxik |
| 8,795,169 B2 | 8/2014 | Cosentino et al. |
| 8,801,636 B2 | 8/2014 | Lewicke et al. |
| 8,823,507 B1 | 9/2014 | Touloumtzis |
| 8,836,243 B2 | 9/2014 | Eisele et al. |
| 8,843,484 B2 | 9/2014 | Gu et al. |
| 8,852,254 B2 | 10/2014 | Moscovici |
| 8,855,757 B2 | 10/2014 | Kapoor |
| 8,862,532 B2 | 10/2014 | Beaulieu et al. |
| 8,870,740 B2 | 10/2014 | Clegg et al. |
| 8,896,427 B1 | 11/2014 | Ramirez |
| 8,907,803 B2 | 12/2014 | Martin |
| 8,924,026 B2 | 12/2014 | Federspiel et al. |
| 8,941,500 B1 | 1/2015 | Faaborg et al. |
| 8,961,414 B2 | 2/2015 | Teller et al. |
| 8,979,913 B2 | 3/2015 | D'Ambrosio |
| 8,986,204 B2 | 3/2015 | Pacey et al. |
| 8,986,427 B2 | 3/2015 | Hauville |
| 9,007,877 B2 | 4/2015 | Godlieb |
| 9,010,019 B2 | 4/2015 | Mittelmark |
| 9,015,610 B2 | 4/2015 | Hunter |
| 9,020,647 B2 | 4/2015 | Johnson et al. |
| 9,041,530 B2 | 5/2015 | Spragg et al. |
| 9,044,567 B2 | 6/2015 | Poirrier et al. |
| 9,066,405 B2 | 6/2015 | Van De Ven |
| D734,958 S | 7/2015 | Gosling et al. |
| 9,095,029 B2 | 7/2015 | Lu |
| D737,078 S | 8/2015 | McKinney |
| 9,098,114 B2 | 8/2015 | Potter et al. |
| 9,104,183 B2 | 8/2015 | Zheng et al. |
| 9,110,958 B2 | 8/2015 | Brust et al. |
| 9,118,499 B2 | 8/2015 | Hunter |
| 9,125,257 B2 | 9/2015 | Eisele et al. |
| 9,125,274 B1 | 9/2015 | Brunault |
| 9,147,296 B2 | 9/2015 | Ricci |
| 9,154,559 B1 | 10/2015 | Bovee |
| 9,155,165 B2 | 10/2015 | Chobot |
| 9,204,518 B2 | 12/2015 | Jung |
| 9,220,202 B2 | 12/2015 | Maxik |
| 9,226,371 B2 | 12/2015 | Mohan |
| 9,230,064 B2 | 1/2016 | Yanev et al. |
| 9,230,560 B2 | 1/2016 | Ehsani |
| 9,235,978 B1 | 1/2016 | Charlton |
| 9,236,026 B2 | 1/2016 | Jia |
| 9,248,309 B2 | 2/2016 | Pugh et al. |
| 9,251,716 B2 | 2/2016 | Drane et al. |
| 9,286,442 B2 | 3/2016 | Csoma et al. |
| 9,297,748 B2 | 3/2016 | Risk |
| 9,306,763 B2 | 4/2016 | Tatzel |
| 9,326,363 B2 | 4/2016 | Godlieb |
| 9,345,091 B2 | 5/2016 | Pickard |
| 9,360,731 B2 | 6/2016 | Berman et al. |
| 9,370,689 B2 | 6/2016 | Guillama et al. |
| D761,598 S | 7/2016 | Goodman |
| 9,392,665 B2 | 7/2016 | Eisele et al. |
| 9,401,098 B2 | 7/2016 | Ellis |
| 9,410,664 B2 | 8/2016 | Krames |
| 9,420,667 B2 | 8/2016 | Mohan |
| 9,429,009 B2 | 8/2016 | Paulk et al. |
| 9,430,617 B2 | 8/2016 | Brust et al. |
| 9,430,927 B2 | 8/2016 | Yu et al. |
| 9,450,904 B2 | 9/2016 | Wheeler et al. |
| 9,456,482 B1 | 9/2016 | Pope |
| 9,465,392 B2 | 10/2016 | Bradley |
| 9,471,751 B1 | 10/2016 | Kahn et al. |
| 9,493,112 B2 | 11/2016 | Thomas |
| 9,501,049 B2 | 11/2016 | Balakrishnan |
| 9,510,426 B2 | 11/2016 | Chemel |
| 9,526,455 B2 | 12/2016 | Horseman |
| 9,576,939 B2 | 2/2017 | Roth |
| 9,589,475 B2 | 3/2017 | Lycas |
| 9,589,480 B2 | 3/2017 | Ellis |
| 9,593,861 B1 | 3/2017 | Burnett |
| 9,595,118 B2 | 3/2017 | Maxik |
| 9,609,724 B2 | 3/2017 | Bulut |
| 9,615,429 B2 | 4/2017 | Roosli |
| 9,636,520 B2 | 5/2017 | Pedersen |
| 9,642,209 B2 | 5/2017 | Eisele et al. |
| 9,655,195 B2 | 5/2017 | Tseng |
| 9,672,472 B2 | 6/2017 | Snyder et al. |
| 9,694,496 B2 | 7/2017 | Martinson et al. |
| 9,696,052 B2 | 7/2017 | Malchiondo |
| 9,699,874 B2 | 7/2017 | Phillips |
| 9,703,931 B2 | 7/2017 | Hinkel |
| 9,715,242 B2 | 7/2017 | Pillai et al. |
| 9,730,298 B2 | 8/2017 | Vangeel et al. |
| 9,734,293 B2 | 8/2017 | Collins, Jr. et al. |
| 9,734,542 B2 | 8/2017 | Ji et al. |
| 9,763,592 B2 | 9/2017 | Le et al. |
| 9,774,697 B2 | 9/2017 | Li et al. |
| 9,788,373 B1 | 10/2017 | Chowdhury |
| 9,794,355 B2 | 10/2017 | Moghaddam et al. |
| 9,820,656 B2 | 11/2017 | Olivier |
| 9,827,439 B2 | 11/2017 | Maxik |
| 9,839,083 B2 | 12/2017 | Van De Ven |
| 9,842,313 B2 | 12/2017 | B'Far et al. |
| 9,870,449 B2 | 1/2018 | Rajan et al. |
| 9,875,667 B2 | 1/2018 | Thompson et al. |
| 9,881,511 B1 | 1/2018 | Srinivasan et al. |
| 9,887,854 B2 | 2/2018 | Park |
| 9,890,969 B2 | 2/2018 | Martin |
| 9,907,149 B1 | 2/2018 | Dolan |
| 9,909,772 B2 | 3/2018 | Bazar |
| 9,913,583 B2 | 3/2018 | Smith, Sr. |
| 9,915,438 B2 | 3/2018 | Cheatham, III |
| 9,916,474 B2 | 3/2018 | Tribble et al. |
| 9,924,243 B2 | 3/2018 | Lupien |
| 9,933,182 B2 | 4/2018 | Alfakhrany |
| 9,939,823 B2 | 4/2018 | Ovadia |
| 9,952,614 B2 | 4/2018 | Hunter |
| 9,955,423 B2 | 4/2018 | Kates |
| 9,955,550 B2 | 4/2018 | Baek |
| 9,958,180 B2 | 5/2018 | Mahar |
| 9,959,997 B2 | 5/2018 | Bailey |
| 9,984,590 B2 | 5/2018 | Stevens |
| 9,986,313 B2 | 5/2018 | Schwarzkopf |
| 9,992,292 B2 | 6/2018 | Gunnarsson et al. |
| 9,993,198 B2 | 6/2018 | Dugan |
| 10,001,789 B2 | 6/2018 | Hunka |
| 10,022,556 B1 | 7/2018 | Holbert |
| 10,024,699 B2 | 7/2018 | Rapetti Mogol |
| 10,030,833 B2 | 7/2018 | Adler |
| 10,031,973 B2 | 7/2018 | Dey |
| 10,039,169 B2 | 7/2018 | Chen |
| 10,042,336 B2 | 8/2018 | Cipollo |
| 10,047,971 B2 | 8/2018 | Nyamjav |
| 10,051,707 B2 | 8/2018 | Deixler |
| 10,052,061 B2 | 8/2018 | Raymann |
| 10,054,534 B1 | 8/2018 | Nourbakhsh |
| 10,057,963 B2 | 8/2018 | Mead |
| 10,064,255 B2 | 8/2018 | Barroso |
| 10,068,297 B2 | 9/2018 | Hull Roskos |
| 10,072,866 B2 | 9/2018 | Bazar |
| 10,075,757 B2 | 9/2018 | Ugan |
| 10,078,865 B2 | 9/2018 | Joshi |
| 10,088,577 B2 | 10/2018 | Klein |
| 10,091,017 B2 | 10/2018 | Landow |
| 10,091,303 B1 | 10/2018 | Ledvina |
| 10,129,367 B2 | 11/2018 | Yan |

(56) References Cited

U.S. PATENT DOCUMENTS

| | | |
|---|---|---|
| 10,178,972 B2 | 1/2019 | Raymann |
| 10,271,400 B2 | 4/2019 | Parker |
| 2002/0072322 A1 | 6/2002 | Sharp |
| 2002/0096121 A1 | 7/2002 | Ingman et al. |
| 2002/0119281 A1 | 8/2002 | Higgins et al. |
| 2002/0128864 A1 | 9/2002 | Maus et al. |
| 2002/0163529 A1 | 11/2002 | Evanicky |
| 2002/0187082 A1 | 12/2002 | Wu et al. |
| 2003/0100837 A1 | 5/2003 | Lys |
| 2003/0133292 A1 | 7/2003 | Mueller et al. |
| 2003/0199244 A1 | 10/2003 | Siddaramanna |
| 2003/0209140 A1 | 11/2003 | Kutt |
| 2003/0209501 A1 | 11/2003 | Leung |
| 2004/0002792 A1 | 1/2004 | Hoffknecht |
| 2004/0060677 A1 | 4/2004 | Huang |
| 2004/0065098 A1 | 4/2004 | Choi et al. |
| 2004/0105264 A1 | 6/2004 | Spero |
| 2004/0160199 A1 | 8/2004 | Morgan et al. |
| 2004/0176666 A1 | 9/2004 | Chait |
| 2004/0178751 A1 | 9/2004 | Mueller |
| 2004/0212321 A1 | 10/2004 | Lys |
| 2004/0245351 A1 | 12/2004 | Orfield et al. |
| 2004/0264193 A1 | 12/2004 | Okumura |
| 2004/0267385 A1 | 12/2004 | Lingemann |
| 2005/0110416 A1 | 5/2005 | Veskovic |
| 2005/0151489 A1 | 7/2005 | Lys |
| 2005/0177957 A1 | 8/2005 | Long |
| 2005/0191505 A1 | 9/2005 | Akarsu et al. |
| 2005/0200578 A1 | 9/2005 | Lee |
| 2005/0213353 A1 | 9/2005 | Lys |
| 2005/0214533 A1 | 9/2005 | Shimosaki et al. |
| 2005/0218870 A1 | 10/2005 | Lys |
| 2005/0225976 A1 | 10/2005 | Zampini et al. |
| 2005/0231133 A1 | 10/2005 | Lys |
| 2005/0236998 A1 | 10/2005 | Mueller et al. |
| 2005/0253533 A1 | 11/2005 | Lys |
| 2005/0281531 A1* | 12/2005 | Unmehopa ........ H04N 21/4333 386/230 |
| 2006/0000257 A1 | 1/2006 | Samadpour et al. |
| 2006/0002110 A1 | 1/2006 | Dowling |
| 2006/0017928 A1 | 1/2006 | Crowther |
| 2006/0018118 A1 | 1/2006 | Lee |
| 2006/0018428 A1 | 1/2006 | Li |
| 2006/0103728 A1 | 5/2006 | Ishigami et al. |
| 2006/0106437 A1 | 5/2006 | Czeisler |
| 2006/0111944 A1 | 5/2006 | Sirmans et al. |
| 2006/0154596 A1 | 7/2006 | Meneely, Jr. |
| 2006/0162552 A1 | 7/2006 | Yost |
| 2006/0172579 A1 | 8/2006 | Murphy et al. |
| 2006/0173580 A1 | 8/2006 | Desrochers |
| 2006/0184283 A1 | 8/2006 | Lee |
| 2006/0207730 A1 | 9/2006 | Berman et al. |
| 2006/0246149 A1 | 11/2006 | Buchholz et al. |
| 2007/0001617 A1 | 1/2007 | Pogodayev et al. |
| 2007/0024210 A1 | 2/2007 | Zwanenburg et al. |
| 2007/0115665 A1 | 5/2007 | Mueller |
| 2007/0162858 A1 | 7/2007 | Hurley et al. |
| 2007/0198226 A1 | 8/2007 | Lee |
| 2007/0240437 A1 | 10/2007 | Yonezawa |
| 2008/0031832 A1 | 2/2008 | Wakefield et al. |
| 2008/0103561 A1 | 5/2008 | Moscovici |
| 2008/0146892 A1 | 6/2008 | Leboeuf |
| 2008/0182506 A1 | 7/2008 | Jackson |
| 2008/0224121 A1 | 9/2008 | Bose et al. |
| 2008/0225021 A1 | 9/2008 | Hekstra et al. |
| 2008/0246629 A1 | 10/2008 | Tsui et al. |
| 2008/0294012 A1 | 11/2008 | Kurtz et al. |
| 2008/0297027 A1 | 12/2008 | Miller |
| 2009/0015403 A1 | 1/2009 | Kuris |
| 2009/0065596 A1 | 3/2009 | Seem et al. |
| 2009/0068089 A1 | 3/2009 | Hussain et al. |
| 2009/0104086 A1 | 4/2009 | Zax et al. |
| 2009/0126382 A1 | 5/2009 | Rubino |
| 2009/0128044 A1 | 5/2009 | Nevins |
| 2009/0169425 A1 | 7/2009 | Park et al. |
| 2009/0177613 A1 | 7/2009 | Martinez |
| 2009/0223126 A1 | 9/2009 | Garner et al. |
| 2009/0241496 A1 | 10/2009 | Pintault et al. |
| 2009/0242485 A1 | 10/2009 | Cabados |
| 2009/0243517 A1 | 10/2009 | Verfuerth et al. |
| 2009/0273470 A1 | 11/2009 | Sinkevicius |
| 2009/0292180 A1 | 11/2009 | Mirow |
| 2010/0021710 A1 | 1/2010 | Hunt et al. |
| 2010/0084996 A1 | 4/2010 | Van De Sluis |
| 2010/0119461 A1 | 5/2010 | Bicard-Benhamou et al. |
| 2010/0146855 A1 | 6/2010 | Ma |
| 2010/0169108 A1 | 7/2010 | Karkanias et al. |
| 2010/0185064 A1 | 7/2010 | Bandic |
| 2010/0197495 A1 | 8/2010 | Filippini et al. |
| 2010/0217099 A1 | 8/2010 | LeBoeuf et al. |
| 2010/0265803 A1 | 10/2010 | Lee |
| 2010/0277106 A1 | 11/2010 | Baaijens |
| 2010/0289643 A1 | 11/2010 | Trundle |
| 2010/0298981 A1 | 11/2010 | Chamorro |
| 2011/0010014 A1 | 1/2011 | Oexman |
| 2011/0066465 A1 | 3/2011 | Orfield |
| 2011/0084614 A1 | 4/2011 | Eisele |
| 2011/0190913 A1 | 8/2011 | Van De Sluis |
| 2011/0237905 A1 | 9/2011 | Kutzik et al. |
| 2012/0011033 A1 | 1/2012 | Salgia |
| 2012/0019386 A1 | 1/2012 | Doraiswami |
| 2012/0031984 A1 | 2/2012 | Feldmeier |
| 2012/0064818 A1 | 3/2012 | Kurelowech |
| 2012/0072032 A1 | 3/2012 | Powell |
| 2012/0158203 A1 | 6/2012 | Feldstein |
| 2012/0176041 A1 | 7/2012 | Birru |
| 2012/0206726 A1 | 8/2012 | Pervez et al. |
| 2012/0279120 A1 | 11/2012 | Prescott |
| 2012/0298599 A1 | 11/2012 | Sichello |
| 2013/0027637 A1 | 1/2013 | Hosoki |
| 2013/0035208 A1 | 2/2013 | Dalebout et al. |
| 2013/0065098 A1 | 3/2013 | Ohkawa |
| 2013/0081541 A1 | 4/2013 | Hasenoehrl et al. |
| 2013/0102852 A1 | 4/2013 | Kozloski et al. |
| 2013/0119891 A1 | 5/2013 | Herremans |
| 2013/0134962 A1 | 5/2013 | Kamel |
| 2013/0141235 A1 | 6/2013 | Utter, II |
| 2013/0208576 A1 | 8/2013 | Loree, IV et al. |
| 2013/0229114 A1 | 9/2013 | Eisele |
| 2013/0276371 A1 | 10/2013 | Birru |
| 2013/0342111 A1 | 12/2013 | Mohan |
| 2014/0058566 A1 | 2/2014 | Rains, Jr. et al. |
| 2014/0067130 A1 | 3/2014 | Pillai |
| 2014/0089836 A1 | 3/2014 | Damani et al. |
| 2014/0093551 A1 | 4/2014 | Averett et al. |
| 2014/0099348 A1 | 4/2014 | Averett et al. |
| 2014/0155705 A1* | 6/2014 | Papadopoulos ...... A61B 5/0022 600/301 |
| 2014/0243935 A1 | 8/2014 | Brainard |
| 2014/0283450 A1 | 9/2014 | Darlington |
| 2014/0298719 A1 | 10/2014 | Mackin |
| 2014/0318011 A1 | 10/2014 | Jarvinen et al. |
| 2015/0015152 A1 | 1/2015 | Aboulnaga et al. |
| 2015/0052975 A1 | 2/2015 | Martin |
| 2015/0066578 A1 | 3/2015 | Manocchia et al. |
| 2015/0088786 A1 | 3/2015 | Anandhakrishnan |
| 2015/0102730 A1 | 4/2015 | Eisele |
| 2015/0126806 A1 | 5/2015 | Barroso et al. |
| 2015/0204561 A1 | 7/2015 | Sadwick |
| 2015/0212057 A1 | 7/2015 | Darveau |
| 2015/0234369 A1 | 8/2015 | Wen |
| 2015/0309484 A1 | 10/2015 | Lyman |
| 2015/0382427 A1 | 12/2015 | Eisele |
| 2016/0019813 A1 | 1/2016 | Mullen |
| 2016/0203700 A1 | 7/2016 | Bruhn |
| 2016/0206898 A1 | 7/2016 | Brainard |
| 2016/0213946 A1 | 7/2016 | Brainard |
| 2016/0231014 A1 | 8/2016 | Ro et al. |
| 2016/0253802 A1 | 9/2016 | Venetianer et al. |
| 2016/0284172 A1 | 9/2016 | Weast et al. |
| 2016/0313245 A1 | 10/2016 | Sato |
| 2016/0339203 A1 | 11/2016 | Krames |
| 2016/0334436 A1 | 11/2016 | Parker |
| 2017/0023225 A1 | 1/2017 | Chen |

(56) References Cited

U.S. PATENT DOCUMENTS

| | | |
|---|---|---|
| 2017/0053068 A1 | 2/2017 | Pillai et al. |
| 2017/0065792 A1 | 3/2017 | Bonvallet |
| 2017/0068782 A1 | 3/2017 | Pillai et al. |
| 2017/0136206 A1 | 5/2017 | Pillai et al. |
| 2017/0139386 A1 | 5/2017 | Pillai et al. |
| 2017/0162548 A1 | 6/2017 | Roth |
| 2017/0189640 A1 | 7/2017 | Sadwick |
| 2017/0191695 A1 | 7/2017 | Bruhn |
| 2017/0196510 A1 | 7/2017 | Ouwerkerk |
| 2017/0208021 A1 | 7/2017 | Ingram et al. |
| 2017/0238401 A1 | 8/2017 | Sadwick |
| 2017/0259079 A1 | 9/2017 | Grajcar |
| 2017/0299210 A1 | 10/2017 | Nyamjav |
| 2017/0300647 A1 | 10/2017 | Goldberg et al. |
| 2017/0300651 A1 | 10/2017 | Strobridge |
| 2017/0300655 A1 | 10/2017 | Lane et al. |
| 2017/0301255 A1 | 10/2017 | Lee et al. |
| 2017/0319816 A1 | 11/2017 | Sokol |
| 2017/0325310 A1 | 11/2017 | Chen |
| 2017/0326380 A1 | 11/2017 | Moore-Ede |
| 2017/0347907 A1 | 12/2017 | Le et al. |
| 2017/0348506 A1 | 12/2017 | Berman |
| 2017/0356670 A1 | 12/2017 | Zhang |
| 2017/0359879 A1 | 12/2017 | Eisele et al. |
| 2018/0011978 A1 | 1/2018 | Reeckmann |
| 2018/0012242 A1 | 1/2018 | Phan |
| 2018/0025125 A1 | 1/2018 | Crane et al. |
| 2018/0025126 A1 | 1/2018 | Barnard et al. |
| 2018/0042077 A1 | 2/2018 | Riley |
| 2018/0043130 A1 | 2/2018 | Moore Ede |
| 2018/0077767 A1 | 3/2018 | Soler |
| 2018/0082261 A1 | 3/2018 | Hendriks et al. |
| 2018/0082393 A1 | 3/2018 | Ahrens et al. |
| 2018/0107962 A1 | 4/2018 | Lundin et al. |
| 2018/0108442 A1 | 4/2018 | Borve |
| 2018/0149802 A1 | 5/2018 | Krames |
| 2018/0157864 A1 | 6/2018 | Tribble et al. |
| 2018/0160944 A1 | 6/2018 | Aubert |
| 2018/0165588 A1 | 6/2018 | Saxena et al. |
| 2018/0166171 A1 | 6/2018 | Pulitzer et al. |
| 2018/0178063 A1 | 6/2018 | Silver et al. |
| 2018/0182472 A1 | 6/2018 | Preston et al. |
| 2018/0193589 A1 | 7/2018 | McLaughlin et al. |
| 2018/0196925 A1 | 7/2018 | Mukherjee et al. |
| 2018/0197625 A1 | 7/2018 | Lobach |
| 2018/0197637 A1 | 7/2018 | Chowdhury |
| 2018/0197638 A1 | 7/2018 | Blanshard et al. |
| 2018/0206783 A1 | 7/2018 | Yoon |
| 2018/0207445 A1 | 7/2018 | Maxik |
| 2018/0218289 A1 | 8/2018 | Albrecht |
| 2018/0226158 A1 | 8/2018 | Fish et al. |
| 2018/0247029 A1 | 8/2018 | Fish et al. |
| 2018/0285934 A1 | 10/2018 | Baughman |
| 2018/0295696 A1 | 10/2018 | Li |
| 2018/0295704 A1 | 10/2018 | Haverlag |
| 2018/0311464 A1 | 11/2018 | Krames |
| 2018/0318602 A1 | 11/2018 | Ciccarelli |
| 2018/0320919 A1 | 11/2018 | Tang |
| 2018/0322240 A1 | 11/2018 | Goyal |
| 2018/0322253 A1 | 11/2018 | Goyal |
| 2018/0322255 A1 | 11/2018 | Connell, II et al. |
| 2018/0330626 A1 | 11/2018 | Donadio |
| 2018/0331845 A1 | 11/2018 | Warren |
| 2018/0336500 A1 | 11/2018 | Pinho et al. |
| 2018/0336530 A1 | 11/2018 | Johnson et al. |
| 2018/0339127 A1 | 11/2018 | Van Reen |
| 2018/0342327 A1 | 11/2018 | Madan et al. |
| 2018/0349689 A1 | 12/2018 | Lee |
| 2018/0349945 A1 | 12/2018 | Jayaraman |
| 2018/0350455 A1 | 12/2018 | Rosen |
| 2018/0350456 A1 | 12/2018 | Kendrick et al. |
| 2018/0351758 A1 | 12/2018 | Becker |
| 2018/0351761 A1 | 12/2018 | Li |
| 2018/0353073 A1 | 12/2018 | Boucher et al. |
| 2018/0353108 A1 | 12/2018 | Prate |
| 2018/0358117 A1 | 12/2018 | Neagle |
| 2018/0358129 A1 | 12/2018 | Gorzelniak et al. |
| 2018/0358130 A1 | 12/2018 | Schmidt |
| 2018/0369637 A1 | 12/2018 | Hoang et al. |
| 2018/0374053 A1 | 12/2018 | Willamowski et al. |
| 2018/0374572 A1 | 12/2018 | Ackerman |
| 2018/0374586 A1 | 12/2018 | Baughman et al. |
| 2019/0001059 A1 | 1/2019 | Handler |
| 2019/0005844 A1 | 1/2019 | Dragicevic et al. |
| 2019/0007424 A1 | 1/2019 | Ford et al. |
| 2019/0007927 A1 | 1/2019 | Blahnik et al. |
| 2019/0013960 A1 | 1/2019 | Sadwick |
| 2019/0014643 A1 | 1/2019 | Gharabegian |
| 2019/0028549 A1 | 1/2019 | Ledvina |
| 2019/0046109 A1 | 2/2019 | Lewis |
| 2019/0320516 A1 | 10/2019 | Parker |

FOREIGN PATENT DOCUMENTS

| | | |
|---|---|---|
| CN | 1150882 A | 5/1997 |
| CN | 1544222 A | 11/2004 |
| CN | 101421558 A | 4/2009 |
| CN | 201414191 Y | 2/2010 |
| CN | 202551821 U | 11/2012 |
| CN | 103040443 A | 4/2013 |
| CN | 103197659 A | 7/2013 |
| CN | 103277870 A | 9/2013 |
| CN | 203175090 U | 9/2013 |
| CN | 103531174 A | 1/2014 |
| CN | 103604198 A | 2/2014 |
| CN | 203454309 U | 2/2014 |
| CN | 204759076 | 11/2015 |
| EP | 1 067 825 B1 | 12/2004 |
| EP | 1 821 582 A1 | 8/2007 |
| EP | 2 132 960 | 12/2009 |
| EP | 2 431 541 A2 | 3/2012 |
| EP | 2 488 912 | 8/2012 |
| JP | 60-110520 A | 6/1985 |
| JP | 5-52361 A | 3/1993 |
| JP | 6-58593 A | 3/1994 |
| JP | 6-159763 A | 6/1994 |
| JP | 6-225858 A | 8/1994 |
| JP | 9-303842 A | 11/1997 |
| JP | 10-238089 A | 9/1998 |
| JP | 2000-130828 A | 5/2000 |
| JP | 2000-294388 A | 10/2000 |
| JP | 2001-224078 A | 8/2001 |
| JP | 2001-286226 A | 10/2001 |
| JP | 2001-314882 A | 11/2001 |
| JP | 2002-42546 A | 2/2002 |
| JP | 2002-59152 A | 2/2002 |
| JP | 2003-42507 A | 2/2003 |
| JP | 2003-42509 A | 2/2003 |
| JP | 2003-83590 A | 3/2003 |
| JP | 2003-232559 A | 8/2003 |
| JP | 2004005313 A | 1/2004 |
| JP | 2004-53130 A | 2/2004 |
| JP | 2005-040769 A | 2/2005 |
| JP | 2005-177726 A | 7/2005 |
| JP | 2005-211319 A | 8/2005 |
| JP | 2005-235634 A | 9/2005 |
| JP | 2006-210045 A | 8/2006 |
| JP | 2006-522699 A | 10/2006 |
| JP | 2006-321721 A | 11/2006 |
| JP | 2007-170761 A | 7/2007 |
| JP | 2007-184436 A | 7/2007 |
| JP | 2008-125541 A | 6/2008 |
| JP | 2008-157548 A | 7/2008 |
| JP | 2008-204640 A | 9/2008 |
| JP | 2010-182661 A | 8/2010 |
| JP | 2010-239878 A | 10/2010 |
| JP | 2011-146137 A | 7/2011 |
| JP | 2012-1931 A | 1/2012 |
| JP | 2012149839 A | 8/2012 |
| JP | 2013140523 A | 7/2013 |
| KR | 2000-0009824 A | 2/2000 |
| KR | 2001-0048235 A | 6/2001 |
| KR | 2003-0074107 A | 9/2003 |
| KR | 10-2005-0003899 A | 1/2005 |

(56) References Cited

FOREIGN PATENT DOCUMENTS

| KR | 10-0771486 | B1 | 10/2007 |
|---|---|---|---|
| KR | 10-0804892 | B1 | 2/2008 |
| KR | 10-2012-0004243 | A | 1/2012 |
| KR | 10-1102733 | B1 | 1/2012 |
| KR | 10-1135926 | B1 | 4/2012 |
| KR | 20120039359 | A | 4/2012 |
| KR | 20130108709 | | 10/2013 |
| KR | 10-2013-0124184 | A | 11/2013 |
| WO | 00/39964 | A1 | 7/2000 |
| WO | 2004/037301 | A2 | 5/2004 |
| WO | 2007/026387 | A2 | 3/2007 |
| WO | 2008/043396 | A1 | 4/2008 |
| WO | 2008/102308 | A2 | 8/2008 |
| WO | 2008/120127 | A1 | 10/2008 |
| WO | 2008/135093 | A1 | 11/2008 |
| WO | 2009/030641 | A1 | 3/2009 |
| WO | 2009/044330 | A1 | 4/2009 |
| WO | 2010/046875 | A2 | 4/2010 |
| WO | 2010/087386 | A1 | 8/2010 |
| WO | 2010/115720 | A2 | 10/2010 |
| WO | 2011/033377 | A2 | 3/2011 |
| WO | 2011/046875 | A1 | 4/2011 |
| WO | 2012/104773 | A1 | 8/2012 |
| WO | 2012/151407 | A1 | 8/2012 |
| WO | 2013/014337 | A2 | 1/2013 |
| WO | 2013/049297 | A2 | 4/2013 |
| WO | 2013175348 | | 11/2013 |
| WO | 2014036133 | | 3/2014 |
| WO | 2015/130786 | A1 | 9/2015 |
| WO | 2015200730 | A1 | 12/2015 |
| WO | 2016019005 | A1 | 2/2016 |

OTHER PUBLICATIONS

American Ultraviolet, "Handheld Germicidal Fixtures," retrieved from http://americanultraviolet.com/germicidal_solutions/commercial_products/handheld . . . , retrieved on Aug. 13, 2012, 1 page.
American Ultraviolet, "In Room Germicidal Solutions," retrieved from http://www.americanultraviolet.com, 2 pages.
Averett et al., "Titanium Dioxide Photocatalytic Compositions and Uses Thereof," U.S. Appl. No. 61/482,393, filed May 4, 2011, 25 pages.
Brookstone, "Tranquil Moments® Advanced Sleep Sounds," retrieved from http://www.brookstone.com/tranquil-moments-advanced-sleep-sound . . . , retrieved on Apr. 28, 2014, 3 pages.
Canadian Office Action, dated Jul. 18, 2017, for Canadian Application No. 2,946,367, 3 pages.
Canadian Office Action, dated Jul. 25, 2017, for Canadian Application No. 2,940,766, 6 pages.
Chinese Office Action, dated May 5, 2016, for Chinese Application No. 201380051774.0, 10 pages.
Delos, "Delos and MGM Grand Las Vegas Introduce First-Ever Stay Well Rooms," Sep. 20, 2012, retrieved from http://delosliving.com/staywell/delos-mgm-grand-las-vegas-introduce-first-ever-stay-well- . . . retrieved on May 14, 2014, 4 pages.
Delos, "Delos Announces First-Ever WELL™ Certified Office at CBRE Headquarters in Los Angeles," Nov. 19, 2013, retrieved from http://delosliving.com/press-release/delos-the-pioneer-of-wellness-real-estate-announces-fi . . . , retrieved on May 14, 2014, 4 pages.
Delos, "Introducing Wellness Real Estate—Can Your Home Actually Improve Your Health?," May 1, 2012, retrieved from http://delosliving.com/press-release/can-your-home-actually-improve-your-health/, retrieved on May 14, 2014, 3 pages.
Delos, "MGM Grand and Delos Complete Expansion of Stay Well Experience and Introduce New Stay Well Lounge," Feb. 26, 2014, retrieved from http://delosliving.com/press-release/mgm-grand-and-delos-complete-expansion-of-stay-we . . . , retrieved on May 14, 2014, 4 pages.
Delos, "World's First WELL® Certified Restaurants Introduced by Delos and LYFE Kitchen," Dec. 4, 2013, retrieved from http://delosliving.com/press-release/worlds-first-well-certified-restaurants-introduced-by-d . . . retrieved on May 14, 2014, 4 pages.
Delos, "World's First Wellness-Infused Student Housing Model in Philadelphia for St. Joseph's University Introduced by Delos and Cross Properties," Nov. 25, 2013, retrieved from http://delosliving.com/press-release/delos-the-pioneer-of-wellness-real-estate-and-cross-pr . . . , retrieved on May 14, 2014, 4 pages.
Eisele et al., "LED Lighting System," Amendment filed Oct. 24, 2012, for U.S. Appl. No. 12/900,158, 12 pages.
Eisele et al., "LED Lighting System," Notice of Allowance dated Jan. 9, 2013, for U.S. Appl. No. 12/900,158, 9 pages.
Eisele et al., "LED Lighting System," Notice of Allowance, dated Apr. 21, 2015, for U.S. Appl. No. 14/486,753, 9 pages.
Eisele et al., "LED Lighting System," Notice of Allowance, dated Mar. 14, 2016, for U.S. Appl. No. 14/805,243, 6 pages.
Eisele et al., "LED Lighting System," Notice of Allowance, dated May 13, 2014, for U.S. Appl. No. 13/863,589, 6 pages.
Eisele et al., "LED Lighting System," Office Action dated Feb. 4, 2015, for U.S. Appl. No. 14/486,753, 7 pages.
Eisele et al., "LED Lighting System," Office Action dated Jul. 26, 2012, for U.S. Appl. No. 12/900,158, 13 pages.
Eisele et al., "LED Lighting System," Office Action dated Jun. 5, 2013, for U.S. Appl. No. 13/863,589, 6 pages.
Eisele et al., "LED Lighting System," Office Action dated Nov. 1, 2013, for U.S. Appl. No. 13/863,589, 7 pages.
Eisele et al., "LED Lighting System," Office Action dated Oct. 22, 2015, for U.S. Appl. No. 14/805,243, 14 pages.
Eisele et al., "LED Lighting System," Preliminary Amendment filed Dec. 30, 2014, for U.S. Appl. No. 14/486,753, 69 pages.
Eisele et al., "LED Lighting System," Preliminary Amendment, filed Sep. 15, 2015, for U.S. Appl. No. 14/805,243, 9 pages.
Eisele et al., "LED Lighting System," Response filed Jan. 27, 2014, for U.S. Appl. No. 13/863,589, 3 pages.
Eisele et al., "LED Lighting System," Response filed Jan. 5, 2016, for U.S. Appl. No. 14/805,243, 3 pages.
Eisele et al., "LED Lighting System," Response filed Mar. 6, 2015, for U.S. Appl. No. 14/486,753, 3 pages.
Eisele et al., "LED Lighting System," Response filed Sep. 4, 2013, for U.S. Appl. No. 13/863,589, 3 pages.
Eisele et al., "LED Lighting System," Second Preliminary Amendment filed Dec. 30, 2014, for U.S. Appl. No. 14/486,753, 9 pages.
Eisele et al., "LED Lighting System," U.S. Appl. No. 61/249,858, filed Oct. 8, 2009, 58 pages.
European communication pursuant to Rule 164(1) EPC, dated Mar. 30, 2016, for European Application No. 13833105.3-1853 / 2891019, 9 pages.
European Search Report for EP Application No. 15160578.9, dated Aug. 11, 2015, 8 pages.
Extended European Search Report, dated Jul. 12, 2017, for European Application No. 15754628.4-1958, 11 pages.
Extended European Search Report, dated Jul. 28, 2016, for European Application No. 13833105.3-1853 / 2891019, 17 pages.
Extended European Search Report, dated Nov. 5, 2014, for European Application No. 12779504.5-1352, 6 pages.
Fabrictech International, "PureCare™ Antibacterial Silver," retrieved from http://www.fabrictech.com/shop/purecaresilver.html, retrieved on Aug. 13, 2012, 1 page.
Fabrictech International, "Total Health & Wellness Protection Package," retrieved from http://www.fabrictech.com/shop/custom-package/total-healthawellness-protection.html, retrieved on Aug. 13, 2012, 3 pages.
Goodman, "Green Wall Frame," Amendment After Allowance, filed May 11, 2016, for U.S. Appl. No. 29/528,147, 8 pages.
Goodman, "Green Wall Frame," Notice of Allowance, dated Feb. 11, 2016, for U.S. Appl. No. 29/528,147, 11 pages.
GSky Plant Systems, Inc., "Smart Wall Cabinet," 2012, retrieved from http://gsky.com/green-walls/smartwall/, retrieved on Apr. 29, 2015, 3 pages.
International Search Report and the Written Opinion of the International Searching Authority, dated Jun. 8, 2015, for International Application No. PCT/US2015/017528, 20 pages.

(56) References Cited

OTHER PUBLICATIONS

International Search Report and Written Opinion of the International Searching Authority, dated Aug. 29, 2016, for International Application No. PCT/US2016/034416, 22 pages.
International Search Report for PCT Application No. PCT/US2010/051791, dated Feb. 4, 2011.
International Search Report, dated Apr. 28, 2016, for International Application No. PCT/US2016/013215, 5 pages.
International Search Report, dated Dec. 26, 2013, for International Application No. PCT/US2013/057070, 4 pages.
Japanese Office Action dated Apr. 25, 2017 for JP Application No. 2015-529995, with English summary, 14 pages.
Jernigan, "Light studies focus on circadian rhythms," BioPhotonics, Jul. 2009, retrieved from http://www.photonics.com/Article.aspx?PID=1&VID=43&IID=396&AID=38995, retrieved on Nov. 3, 2014, 2 pages.
Jernigan, R., "Light Studies Focus on Circadian Rhythms," Photonics Showcase, Nov. 2009, p. 12. (Copy not provided).
Jones, "Acoustical Treatment for Indoor Areas," in *Handbook for Sound Engineers*, Ballou (ed.), Burlington, MA, Focal Press, 2008, 65-94.
Land et al., "Using Vitamin C to Neutralize Chlorine in Water Systems," *United States Department of Agriculture Forest Service Technology and Development Program*, Apr. 2005, retrieved from http://www.fs.fed.us/t-d/pubs/html/05231301/05231301.html on Mar. 1, 2016, 6 pages.
Mold Inspection California, "Killing Mold With Ozone & Thermal Heat," retrieved from http://moldinspectioncalifornia.com/kill_mold_with_ozone.html, 3 pages.
Notice of Allowance, dated Jun. 26, 2017, for U.S. Appl. No. 14/012,444, Pillai et al., "Systems, Methods and Articles for Enhancing Wellness Associated With Habitable Environments," 2 pages.
Notice of Allowance, dated Jun. 6, 2017, for U.S. Appl. No. 14/012,444, Pillai et al., "Systems, Methods and Articles for Enhancing Wellness Associated With Habitable Enviornments," 2 pages.
Oxititan, "Light Powered Protection," retrieved from http://www.oxititan.com, retrieved on Aug. 13, 2012, 2 pages.
Pervez et al., "Photonic Crystal Spectrometer," U.S. Appl. No. 61/349,570, filed May 28, 2010, 52 pages.
Pervez et al., "Photonic Crystal Spectrometer," U.S. Appl. No. 61/278,773, filed Oct. 12, 2009, 78 pages.
Pillai et al., "Systems, Methods and Articles for Enhancing Wellness Associated With Habitable Environments," Amendment, filed Jul. 21, 2016, for U.S. Appl. No. 14/012,444, 25 pages.
Pillai et al., "Systems, Methods and Articles for Enhancing Wellness Associated With Habitable Environments," Preliminary Amendment, filed Mar. 25, 2015, for U.S. Appl. No. 14/012,444, 149 pages.
Pillai et al., "Systems, Methods and Articles for Enhancing Wellness Associated With Habitable Environments," Office Action, dated Mar. 22, 2016, for U.S. Appl. No. 14/012,444, 29 pages.
Preliminary Amendment, filed Sep. 8, 2016, for U.S. Appl. No. 15/187,317, Eisele et al., "LED Lighting System," 9 pages.
Suryadevara et al., "Sensor Data Fusion to determine Wellness of an Elderly in Intelligent Home Monitoring Environment," IEEE, 2012, 6 pages.
Vitashower Corp., "Ascorbic Acid Reduction of Residual Active Chlorine in Potable Water Prior to Halocarboxylate Determination," *Journal of Environmental Monitoring* 2(3): 253-256, 2000, 2 pages.
Vitashower Corp., "Frequently Asked Questions," retrieved from http://www.vitashowercorp.com/FAQs.html, retrieved on May 13, 2014, 3 pages.
Vitashower Corp., "Products," retrieved from http://www.vitashowercorp.com/products.html, retrieved on May 13, 2014, 8 pages.
Vitashower Corp., "Welcome to Vitashower Corporation," retrieved from http://www.vitashowercorp.com/index.html, retrieved on May 13, 2014, 4 pages.

Wikipedia, "Thermostat," as archived on Jan. 24, 2014, URL=https://en.wikipedia.org/w/index.php?title=Thermostat&oldid=592239648, download date Jun. 30, 2017, 10 pages.
Written Opinion of the International Searching Authority, dated Apr. 28, 2016, for International Application No. PCT/US2016/013215, 16 pages.
Written Opinion, dated Dec. 26, 2013, for International Application No. PCT/US2013/057070, 5 pages.
Amendment, filed Jan. 25, 2018, for U.S. Appl. No. 15/421,046, Eisele et al., "LED Lighting System," 6 pages.
Australian Examination report No. 1, dated Dec. 13, 2017, for Australian Application No. 2017200995, 6 pages.
Extended European Search Report, dated Feb. 1, 2018, for European Application No. 17167920.2-1213, 10 pages.
NaturVention, "Science," URL=https://www.naturvention.com/technology-and-science/science/, download date Apr. 5, 2016, 4 pages.
NaturVention, "Technology," URL=https://www.naturvention.com/technology-and-science/, download date Apr. 5, 2016, 6 pages.
Office Action, dated Oct. 27, 2017, for U.S. Appl. No. 15/421,046, Eisele et al., "LED Lighting System," 8 pages.
Communication pursuant to Article 94(3) EPC, dated Mar. 15, 2018, for European Application No. 15 754 628.4-1222, 9 pages.
Extended European Search Report, dated May 28, 2018, for European Application No. 16737803.3-1222 / 3245631, 7 pages.
Office Action, dated May 21, 2018, for U.S. Appl. No. 15/121,953, Pillai et al., "Systems and Articles for Enhancing Wellness Associated With Habitable Environments," 38 pages.
Office Action, dated May 31, 2018, for U.S. Appl. No. 15/421,046, Eisele et al., "LED Lighting System," 9 pages.
"Active Design Guidelines: Promoting Physical Activity and Health in Design," New York City Departments of Design and Construction, 2010.
"Assembly: Civic Design Guidelines," Center for Active Design, 2018.
Australian Patent Examination Report, dated Sep. 14, 2016, for Australian Application No. 2013308871, 5 pages.
Communication pursuant to Article 94(3) EPC, dated Nov. 23, 2016, for European Application No. 13833105.3, 8 pages.
Eisele et al, "LED Lighting System," Office Action, dated Oct. 22, 2015, for U.S. Appl. No. 14/805,243, 18 pages.
Examiner's Report issued in CA Application No. 2,940,766 dated Jan. 11, 2019.
International Search Report for PCT/US2017/048382 dated Jan. 4, 2018 (4 pages).
Office Action issued in CN Application No. 201580021358.5 dated Feb. 2, 2019.
Pillai et al., "Systems, Methods and Articles for Enhancing Wellness Associated With Habitable Environments," U.S. Appl. No. 15/409,233, filed Jan. 18, 2017, 84 pages.
Pillai et al., "Systems, Methods and Articles for Enhancing Wellness Associated With Habitable Environments," U.S. Appl. No. 15/421,022, filed Jan. 31, 2017, 84 pages.
Summons to attend oral proceedings issued in EP Application No. 15754628.4 on Sep. 10, 2018.
Vitashower Corporation, "Vitamin C Shower Filter SF-2000," 2003, retrieved from http://www.vitashowercorp.com/products.html, retrieved on May 13, 2014, 8 pages.
Examination Report issued in AU Application No. 2016202287 dated May 8, 2020.
Extended European Search Report issued in EP Application No. 17844397.4 dated Jun. 17, 2020 (8 pages).
Extended European Search report issued in EP Application No. 20152815.5 dated Aug. 4, 2020.
First Examination Report issued in in Application No. 201617032677 dated Jul. 30, 2020.
Klein, Laura et al., "Coordinating occupant behavior for building energy and comfort management using multi-agent systems," Automatoin in Construction, vol. 22, Mar. 2012, pp. 525-536.

* cited by examiner

SYSTEMS, METHODS AND ARTICLES FOR MONITORING AND ENHANCING HUMAN WELLNESS

CROSS-REFERENCE TO RELATED APPLICATIONS

This application is a U.S. national phase application filed under 35 U.S.C. § 371 of International Application No. PCT/US2016/013215, filed Jan. 13, 2016, designating the United States, which claims priority from U.S. Provisional Application No. 62/102,963, filed Jan. 13, 2015.

BACKGROUND

Technical Field

This disclosure generally relates to habitable environments, for instance, vehicles, homes, hotel or motels, offices and hospitals, and particularly to techniques for enhancing human wellness in such environments.

Description of the Related Art

Most people spend significant amounts of time in habitable environments such as enclosed spaces associated with vehicles, homes, apartments, condominium units, hotel suites or rooms, motel suites or rooms, spas, hospitals, and other public and private facilities. Sometimes these enclosed spaces are controlled, or even owned by, the principal occupants, such as homes, apartments or condominium units. Other times these enclosed spaces are controlled by others, for example, a facility owner or operator who may own and/or operate a hotel, motel, spa or hospital.

Significant time in these spaces exposes the occupant to a wide range of environmental factors, any of which may have either adverse of beneficial effects on the occupant's health, well-being or sense of well-being. Minimizing exposure to environmental factors that tend to have an adverse effect is desirable, as is increasing exposure to environmental factors that tend to have a beneficial effect.

New approaches that enhance habitable environments or monitor human wellness are desirable.

BRIEF SUMMARY

There are numerous factors or conditions that may affect an individual's wellness. These factors may be environmental, biological, event-based, diet-based, activity-based, etc. Often, factors that negatively or positively affect an individual's wellness go undetected by the individual. In some instances, this may be the case because one or more factors that affect an individual's wellness may interact in complex ways or patterns that are undetectable by an individual. In some instances, the effects of one or more factors or conditions may accumulate over time. In some instances, the individual may not collect the relevant data needed to make a wellness assessment or to identify one or more factors or conditions that affect wellness. Thus, without knowledge of the one or more factors that affect an individual's wellness, the individual is unable to take action that may improve his or her wellness.

Various approaches described herein autonomously track wellness information for one or more individuals over time, and across one or more different environments. For example, the wellness monitoring systems described herein may track wellness information for an individual across one or more residential environments, one or more work environments, one or more exercise environments, and/or one or more other environments for instance a spa, clinic or studio (e.g., yoga studio) environment and/or a vehicle environment (e.g., automobile, aircraft, ship).

The wellness monitoring systems described herein may autonomously track wellness information for one or more individuals using a combination of body worn sensors or transducers and/or environmental sensors or transducers. The wellness monitoring systems may assess wellness for one or more individuals based on the tracked wellness information, for example, assessing such based on time, place or location, and/or in light of one or more defined wellness protocols. The wellness monitoring systems may also autonomously prompt one or more individuals to take action based on the wellness assessment. For example, the wellness monitoring systems may prompt an individual to cease an action determined to have a negative effect on the individual's wellness, or to take an action determined to have a positive effect on the individual's wellness. By tracking wellness information from a plurality of sources over time, the wellness monitoring systems described herein can advantageously detect factors, conditions, activities or events that positively or negatively affect an individual's wellness.

A method of operation in a wellness monitoring system which includes at least one processor and at least one nontransitory processor-readable medium which stores at least one of processor-executable instructions or data may be summarized as including, for a first individual, determining a respective value of at least one wellness parameter associated with the first individual, via the at least one processor; determining a respective value of at least one wellness parameter associated with an environment which the first individual occupies, via the at least one processor; assessing a wellness of the first individual, via the at least one processor, based at least in part on a determined respective value of the at least one wellness parameter associated with the first individual and a determined respective value of the at least one wellness parameter associated with the environment which the first individual occupies; and causing a prompting of the first individual to take an action based at least in part on the assessment.

The method of operation in a wellness monitoring system which includes at least one processor and at least one nontransitory processor-readable medium which stores at least one of processor-executable instructions or data may further include receiving information from a number of body worn sensors worn by the first individual, and wherein determining a respective value of at least one wellness parameter associated with the first individual may include determining the respective value of the at least one wellness parameter associated with the first individual from the received information from the number of body worn sensors worn by the first individual.

Receiving information from a number of body worn sensors worn by the first individual may include receiving information representative of at least one of a bodily temperature, a heart rate, a bodily level of oxygen, an amount of perspiration, an electrocardiographic, an amount of bodily activity, a glucose level, a blood pressure, bodily weight, body mass index, bodily alcohol level, an amount of sleep, or a level of sleep.

The method of operation in a wellness monitoring system which includes at least one processor and at least one nontransitory processor-readable medium which stores at least one of processor-executable instructions or data may further include receiving information from a number of ambient environmental sensors located in the environment which the first individual occupies, and wherein determining a respective value of at least one wellness parameter associated with an environment which the first individual occupies may include determining the respective value of the at least one wellness parameter associated with an environment which the first individual occupies from the received information from the number of ambient environmental sensors located in the environment which the first individual occupies.

Receiving information from a number of ambient environmental sensors located in the environment which the first individual occupies may include receiving information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment.

The method of operation in a wellness monitoring system which includes at least one processor and at least one nontransitory processor-readable medium which stores at least one of processor-executable instructions or data may further include receiving information in the form of responses from the first individual to a number of queries proposed to the first individual.

Determining a respective value of at least one wellness parameter associated with the first individual may include determining the respective value of at least one wellness parameter associated with the first individual based on at least one of the responses from the first individual. Determining a respective value of at least one wellness parameter associated with an environment which the first individual occupies may include determining the respective value of at least one wellness parameter associated with the environment which the first individual occupies based on at least one of the responses from the first individual.

The method of operation in a wellness monitoring system which includes at least one processor and at least one nontransitory processor-readable medium which stores at least one of processor-executable instructions or data may further include: detecting a change over time in at least one bodily characteristic of the first individual, via the at least one processor; determining whether the detected change over time in at least one bodily characteristic of the first individual is a positive change or a negative change based at least in part on a defined wellness protocol, via the at least one processor; associating the detected change over time with at least one human controlled activity, via the at least one processor; and determining a corresponding action to prompt the first individual to take based on the associated at least one human controlled activity, via the at least one processor, before prompting the first individual to take an action based at least in part on the assessment, wherein causing a prompting of the first individual to take an action based at least in part on the assessment includes causing at least one of an aural or a visual prompt to be presented.

The method of operation in a wellness monitoring system which includes at least one processor and at least one nontransitory processor-readable medium which stores at least one of processor-executable instructions or data of operation in a wellness monitoring system which includes at least one processor and at least one nontransitory processor-readable medium which stores at least one of processor-executable instructions or data may further include: detecting a change over time in at least one bodily characteristic of the first individual; determining whether the detected change over time in at least one bodily characteristic of the first individual is a positive change or a negative change; associating the detected change over time with at least one action, via the at least one processor; and causing the at least one action to be take autonomously by at least one actuator.

A wellness monitoring system may be summarized as including: at least one processor; and at least one nontransitory processor-readable medium which stores at least one of processor-executable instructions or data, which when executed by the at least one processor causes the at least one processor to: for a first individual, determine a respective value of at least one wellness parameter associated with the first individual; determine a respective value of at least one wellness parameter associated with an environment which the first individual occupies; assess a wellness of the first individual based at least in part on a determined respective value of the at least one wellness parameter associated with the first individual, a determined respective value of the at least one wellness parameter associated with the environment which the first individual occupies, and a defined wellness protocol; and cause a prompting of the first individual to take an action based at least in part on the assessment.

The at least one processor may further receive information from a number of body worn sensors worn by the first individual, and may determine the respective value of the at least one wellness parameter associated with the first individual from the received information from the number of body worn sensors worn by the first individual. The at least one processor may receive information representative of at least one of a bodily temperature, a heart rate, a bodily level of oxygen, an amount of perspiration, an electrocardiographic, an amount of bodily activity, a glucose level, a blood pressure, bodily weight, body mass index, bodily alcohol level, an amount of sleep, a level of sleep. The at least one processor may receive information from a number of ambient environmental sensors located in the environment which the first individual occupies, and may determine the respective value of the at least one wellness parameter associated with an environment which the first individual occupies from the received information from the number of ambient environmental sensors located in the environment which the first individual occupies. The at least one processor may receive information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment. The at least one processor may receive information in the form of responses from the first individual to a number of queries proposed to the first individual. The at least one processor may determine the respective value of at least one wellness parameter associated with the first individual based on at least one of the responses from the first individual. The at least one processor may determine the respective value of at least one wellness parameter associated with the environment which the first individual occupies based on at least one of the responses from the first individual. The at least one processor may: detect a change over time in at least one bodily characteristic of the first individual; determine whether the detected change over time in at least one bodily characteristic of the first individual is a positive change or a negative change; associate the detected change over time with at least one human controlled activity; and determine a corresponding action to prompt the first individual to take based on the associated at least one human controlled activity, before prompting the first individual to take an action based at least in part on the assessment, wherein causing a prompting of the first individual to take an action based at least in part on the assessment may include causing at least one of an aural or a visual prompt to be presented. The at least one processor may: detect a change over time in at least one bodily characteristic of the first individual; determine whether the detected change over time in at least one bodily characteristic of the first individual is a positive change or a negative change; associate the detected change over time with at least one action; and cause the at least one action to be taken autonomously by at least one actuator.

A method of operation in a wellness monitoring system which includes at least one processor and at least one nontransitory processor-readable medium which stores at least one of processor-executable instructions or data may be summarized as including: for a first individual, repeatedly determining a respective value of at least one wellness parameter associated with the first individual, via the at least one processor; repeatedly determining a respective value of at least one wellness parameter associated with a first environment which the first individual occupies, via the at least one processor; assessing a wellness of the first individual, via the at least one processor, based at least in part on the determined respective values of the at least one wellness parameter associated with the first individual and the determined respective values of the at least one wellness parameter associated with the first environment which the first individual occupies; and from time to time, causing a providing of a wellness report based at least in part on the assessment.

The method of operation in a wellness monitoring system which includes at least one processor and at least one nontransitory processor-readable medium which stores at least one of processor-executable instructions or data may further include: repeatedly determining a respective value of at least one wellness parameter associated with a second environment which the first individual occupies, via the at least one processor, and wherein assessing a wellness of the first individual may include assessing the wellness of the first individual based at least in part on the determined respective values of the at least one wellness parameter associated with the first individual, the determined respective values of the at least one wellness parameter associated with the first environment and the second environment which the first individual occupies, and based at least in part on a defined wellness protocol.

Assessing a wellness of the first individual may include compensating for an amount of time that the first individual occupies the first environment relative to an amount of time that the first individual occupies at least the second environment.

The method of operation in a wellness monitoring system which includes at least one processor and at least one nontransitory processor-readable medium which stores at least one of processor-executable instructions or data may further include: determining at least an approximation of the amount of time that the first individual occupies the first environment, via the at least one processor; and determining at least an approximation of the amount of time that the first individual occupies at least a second environment, via the at least one processor, the second environment different from the first environment.

Assessing a wellness of the first individual may include prorating at least one environmental exposure measurement based on a relative amount of time that the first individual occupies each of a plurality of environments including the first environment and at least the second environment.

The method of operation in a wellness monitoring system which includes at least one processor and at least one nontransitory processor-readable medium which stores at least one of processor-executable instructions or data may further include: receiving information from a number of ambient environmental sensors located in at least the first environment which the first individual occupies; and determining a respective value of at least one wellness parameter associated with at least the first environment which the first individual occupies from the received information from the number of ambient environmental sensors located in at least the first environment which the first individual occupies.

Receiving information from a number of ambient environmental sensors located in at least the first environment which the first individual occupies may include receiving information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment.

The method of operation in a wellness monitoring system which includes at least one processor and at least one nontransitory processor-readable medium which stores at least one of processor-executable instructions or data may further include: receiving information from a number of ambient environmental sensors located in at least a second environment which the first individual occupies, the second environment different from the first environment.

The first environment may be a first indoor environment and determining a respective value of at least one wellness parameter associated with the first individual may include determining the respective values of at least one wellness parameter associated with the first individual while the first individual occupies the first indoor environment.

The method of operation in a wellness monitoring system which includes at least one processor and at least one nontransitory processor-readable medium which stores at least one of processor-executable instructions or data may further include: receiving information from a number of body worn sensors worn by the first individual in a second environment, wherein the second environment may be an outdoor environment, and determining a respective value of at least one wellness parameter associated with the first individual may include determining the respective values of at least one wellness parameter associated with the first individual while the first individual occupies the second environment.

Causing a providing of a wellness report based at least in part on the assessment may include providing a wellness dashboard. Causing a providing of a wellness report based at least in part on the assessment may include electronically transmitting a message with an electronic copy of the wellness report attached or with a hyperlink to an electronic copy of the wellness report attached.

A wellness monitoring system may be summarized as including: at least one processor; and at least one nontransitory processor-readable medium which stores at least one of processor-executable instructions or data, which when executed by the at least one processor causes the at least one processor to: for a first individual, repeatedly determine a respective value of at least one wellness parameter associated with the first individual; repeatedly determine a respective value of at least one wellness parameter associated with a first environment which the first individual occupies; assess a wellness of the first individual based at least in part on the determined respective values of the at least one wellness parameter associated with the first individual and the determined respective values of the at least one wellness parameter associated with the first environment which the first individual occupies; and from time to time, cause a wellness report to be provided based at least in part on the assessment.

The at least one processor may further: repeatedly determine a respective value of at least one wellness parameter associated with a second environment which the first individual occupies, and wherein assessing a wellness of the first individual may include assessing the wellness of the first individual based at least in part on the determined respective values of the at least one wellness parameter associated with the first individual and the determined respective values of the at least one wellness parameter associated with the first environment and the second environment which the first individual occupies, and based at least in part on a defined wellness protocol.

The at least one processor may compensate for an amount of time that the first individual occupies the first environment relative to an amount of time that the first individual occupies at least the second environment. The at least one processor may: determine at least an approximation of the amount of time that the first individual occupies the first environment; and determine at least an approximation of the amount of time that the first individual occupies at least a second environment, the second environment different from the first environment. The at least one processor may prorate at least one environmental exposure measurement based on a relative amount of time that the first individual occupies each of a plurality of environments including the first environment and at least the second environment. The at least one processor may: receive information from a number of ambient environmental sensors located in at least the first environment which the first individual occupies; and determine a respective value of at least one wellness parameter associated with at least the first environment which the first individual occupies from the received information from the number of ambient environmental sensors located in at least the first environment which the first individual occupies. The at least one processor may receive information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment. The at least one processor may: receive information from a number of ambient environmental sensors located in at least a second environment which the first individual occupies, the second environment different from the first environment. The first environment may be a first indoor environment and the at least one processor may determine the respective values of at least one wellness parameter associated with the first individual while the first individual occupies the first indoor environment. The at least one processor may: receive information from a number of body worn sensors worn by the first individual in a second environment, wherein the second environment may be an outdoor environment, and wherein determining a respective value of at least one wellness parameter associated with the first individual may include determining the respective values of at least one wellness parameter associated with the first individual while the first individual occupies the second environment. The at least one processor may cause a wellness dashboard to be provided. The at least one processor may cause a transmission of an electronic message with an electronic copy of the wellness report attached or with a hyperlink to an electronic copy of the wellness report attached.

A method of operation in a wellness monitoring system which includes at least one processor and at least one nontransitory processor-readable medium which stores at least one of processor-executable instructions or data may be summarized as including: identifying a presence of a first individual in a first environment during at least a first period; determining a value of at least one wellness parameter associated with the presence during the first period of the first individual in the first environment; identifying a presence of the first individual in a second environment during at least a second period, the second environment remote from the first environment, the second period different from the first period; determining a value of at least one wellness parameter associated with the presence during the second period of the first individual in the second environment; and assessing a wellness of the first individual based at least in part on the determined values of the at least one wellness parameter associated with the presence during at least the first and the second periods of the first individual in the first and the second environments, respectively.

The method of operation in a wellness monitoring system which includes at least one processor and at least one nontransitory processor-readable medium which stores at least one of processor-executable instructions or data may further include: receiving information from a number of ambient environmental sensors located in respective ones of at least the first environment and the second environment which the first individual occupies, and wherein determining a value of at least one wellness parameter associated the presence during the first period and the second period, may include determining the respective value of the at least one wellness parameter associated with the first environment which the first individual occupies from the received information from the number of ambient environmental sensors located in the first environment which the first individual occupies and determining the respective value of the at least one wellness parameter associated with the second environment which the first individual occupies from the received information from the number of ambient environmental sensors located in the second environment which the first individual occupies.

Receiving information from a number of ambient environmental sensors located in respective ones of the first and the second environments may include receiving information representative of at least one of a room temperature, a level of light, a spectral distribution of light, an amount of noise, a measure of air quality, a measure of water quality, or a measure of pressure asserted by at least a portion of the first individual on at least one of a piece of furniture or flooring. Assessing a wellness of the first individual may include prorating at least one environmental exposure measurement based on a relative amount of time that the first individual occupies each of at least the first and the second environments.

The method of operation in a wellness monitoring system which includes at least one processor and at least one nontransitory processor-readable medium which stores at least one of processor-executable instructions or data may further include: receiving information from a number of body worn sensors worn by the first individual, and wherein determining a respective value of at least one wellness parameter associated with the first individual may include determining the respective value of the at least one wellness parameter associated with the first individual from the received information from the number of body worn sensors worn by the first individual.

Receiving information from a number of body worn sensors worn by the first individual may include receiving information representative of at least one of a bodily temperature, a heart rate, a bodily level of oxygen, an amount of perspiration, an electrocardiographic, an amount of bodily activity, a glucose level, a blood pressure, bodily weight, body mass index, bodily alcohol level, an amount of sleep, a level of sleep.

The method of operation in a wellness monitoring system which includes at least one processor and at least one nontransitory processor-readable medium which stores at least one of processor-executable instructions or data may further include: detecting a change over time in at least one bodily characteristic of the first individual, via the at least one processor; determining whether the detected change over time in at least one bodily characteristic of the first individual is a positive change or a negative change, via the at least one processor; associating the detected change over time with at least one human controlled activity, via the at least one processor; determining a corresponding action to prompt the first individual to take based on the associated at least one human controlled activity, via the at least one processor, before prompting the first individual to take an action based at least in part on the assessment; and causing a prompting of the first individual to take an action based at least in part on the assessment.

Causing a prompting of the first individual to take an action based at least in part on the assessment may include causing at least one of an aural or a visual prompt to be presented.

The method of operation in a wellness monitoring system which includes at least one processor and at least one nontransitory processor-readable medium which stores at least one of processor-executable instructions or data may further include: from time to time, causing a providing of a wellness report based at least in part on the assessment.

Identifying a presence of a first individual in a first environment during at least a first period may include reading a unique identifier from an electronic device associated with the first user.

The method of operation in a wellness monitoring system which includes at least one processor and at least one nontransitory processor-readable medium which stores at least one of processor-executable instructions or data may further include: identifying a presence of a second individual in the first environment; determining a value of at least one wellness parameter associated with the presence of the second individual in the first environment; and assessing a wellness of the second individual based at least in part on the determined values of the at least one wellness parameter associated with the presence of the second individual in at least the first environment.

Identifying a presence of a second individual in the first environment may include identifying the presence of the second individual in the first environment during at least the first period. Assessing a wellness of the first individual may include assessing a wellness based at least in part on a defined wellness protocol.

A wellness monitoring system may be summarized as including: at least one processor; and at least one nontransitory processor-readable medium which stores at least one of processor-executable instructions or data, which when executed by the at least one processor causes the at least one processor to: identify a presence of a first individual in a first environment during at least a first period; determine a value of at least one wellness parameter associated with the presence during the first period of the first individual in the first environment; identify a presence of the first individual in a second environment during at least a second period, the second environment remote from the first environment, the second period different from the first period; and determine a value of at least one wellness parameter associated with the presence during the second period of the first individual in the second environment; and assess a wellness of the first individual based at least in part on the determined values of the at least one wellness parameter associated with the presence during at least the first and the second periods of the first individual in the first and the second environments, respectively.

The at least one processor may: receive information from a number of ambient environmental sensors located in respective ones of at least the first environment and the second environment which the first individual occupies, and wherein determining a value of at least one wellness parameter associated the presence during the first period and the second period, may include determining the respective value of the at least one wellness parameter associated with the first environment which the first individual occupies from the received information from the number of ambient environmental sensors located in the first environment which the first individual occupies and determining the respective value of the at least one wellness parameter associated with the second environment which the first individual occupies from the received information from the number of ambient environmental sensors located in the second environment which the first individual occupies. The at least one processor may: receive information representative of at least one of a room temperature, a level of light, a spectral distribution of light, an amount of noise, a measure of air quality, a measure of water quality, or a measure of pressure asserted by at least a portion of the first individual on at least one of a piece of furniture or flooring. The at least one processor may prorate at least one environmental exposure measurement based on a relative amount of time that the first individual occupies each of at least the first and the second environments. The at least one processor may: receive information from a number of body worn sensors worn by the first individual, and determine the respective value of the at least one wellness parameter associated with the first individual from the received information from the number of body worn sensors worn by the first individual. The at least one processor may receive information representative of at least one of a bodily temperature, a heart rate, a bodily level of oxygen, an amount of perspiration, an electrocardiographic, an amount of bodily activity, a glucose level, a blood pressure, bodily weight, body mass index, bodily alcohol level, an amount of sleep, a level of sleep. The at least one processor may: detect a change over time in at least one bodily characteristic of the first individual; determine whether the detected change over time in at least one bodily characteristic of the first individual is a positive change or a negative change; associate the detected change over time with at least one human controlled activity; and determine a corresponding action to prompt the first individual to take based on the associated at least one human controlled activity. The at least one processor may cause a prompt to take an action based at least in part on the assessment to be provided to the first individual. The at least one processor may, from time to time, cause a wellness report to be provided based at least in part on the assessment. The at least one processor may identify the presence of the first individual in the first environment during at least the first period based at least in part on a unique identifier read from an electronic device associated with the first user. The at least one processor may: identify a presence of a second individual in the first environment; determine a value of at least one wellness parameter associated with the presence of the second individual in the first environment; and assess a wellness of the second individual based at least in part on the determined values of the at least one wellness parameter associated with the presence of the second individual in at least the first environment. The at least one processor may identify the presence of the second individual in the first environment during at least the first period. The at least one processor may assess wellness based at least in part on a defined wellness protocol.

A method of operation in a wellness monitoring system which includes at least one processor and at least one nontransitory processor-readable medium which stores at least one of processor-executable instructions or data may be summarized as including: receiving information from at least one of a number of body worn sensors worn by a first individual or a number of environmental sensors; monitoring a level of activity of the first individual in each of at least two environments over a period of time, a first one of the environments different from a second one of the environments; assessing a wellness of the first individual, via the at least one processor, based at least in part on the monitored level of activity of the first individual in the at least two different environments; and causing at least one message to be presented to the first individual based on the assessment of wellness of the first individual.

Receiving information from at least one of a number of body worn sensors worn by the first individual or a number of environmental sensors may include receiving information from at least one motion sensor or accelerometer worn by the first individual. Receiving information from at least one of a number of body worn sensors worn by the first individual or a number of environmental sensors may include receiving information from at least one pressure sensor located in at least one shoe worn by the first individual. Receiving information from at least one of a number of body worn sensors worn by the first individual or a number of environmental sensors may include receiving location specific information from at least one global position transceiver or wireless communications transceiver. Receiving information from at least one of a number of body worn sensors worn by the first individual or a number of environmental sensors may include receiving information from at least one of a number of sensors in at least one of a chair, a sofa, a bed, or a seat in a vehicle. Receiving information from at least one of a number of body worn sensors worn by the first individual or a number of environmental sensors may include receiving information from a residential environment, a business environment, and a vehicle environment. Monitoring a level of activity of a first individual in each of at least two environments over a period of time may include combining information received from both body worn sensors and environmental sensors. Monitoring a level of activity of a first individual in each of at least two environments over a period of time may further include determining a level of activity on a basis of a time and a location based on the received information. Monitoring a level of activity of a first individual in each of at least two environments over a period of time may further include identifying a pattern in the determined level of activity based on the time and the location. Assessing a wellness of the first individual may include assessing the wellness of the first individual based at least in part on a defined wellness protocol. Causing at least one message to be presented to the first individual may include causing an alert to be provided in response to an out of threshold condition. Causing at least one message to be presented to the first individual may include causing a suggestion for improving wellness to be provided.

A wellness monitoring system may be summarized as including: at least one processor; and at least one nontransitory processor-readable medium which stores at least one of processor-executable instructions or data, which when executed by the at least one processor causes the at least one processor to: receive information from at least one of a number of body worn sensors worn by the first individual or a number of environmental sensors; monitor a level of activity of a first individual in each of at least two environments over a period of time, a first one of the environments different from a second one of the environments; assess a wellness of the first individual, via the at least one processor, based at least in part on the monitored level of activity of the first individual in the at least two different environments; and cause at least one message to be presented to the first individual based on the assessment of wellness of the first individual.

The at least one processor may receive information from at least one motion sensor or accelerometer worn by the first individual. The at least one processor may receive information from at least one pressure sensor located in at least one shoe worn by the first individual. The at least one processor may receive location specific information from at least one global position transceiver or wireless communications transceiver. The at least one processor may receive information from at least one of a number of sensors in at least one of a chair, a sofa, a bed, or a seat in a vehicle. The at least one processor may receive information from a residential environment, a business environment, and a vehicle environment. The at least one processor may combine information received from both body worn sensors and environmental sensors. The at least one processor may determine a level of activity based on a time and a location based on the received information. The at least one processor may identify a pattern in the determined level of activity based on the time and the location. The at least one processor may assess the wellness of the first individual based at least in part on a defined wellness protocol. The at least one processor may cause an alert to be provided in response to an out of threshold condition. The at least one processor may cause a suggestion for improving wellness to be provided.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale.

For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with environmental control such as fans, blowers, heaters, coolers such as air conditioners or swamp coolers, compressors, and control systems such as computing systems, as well as networks and other communications channels have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
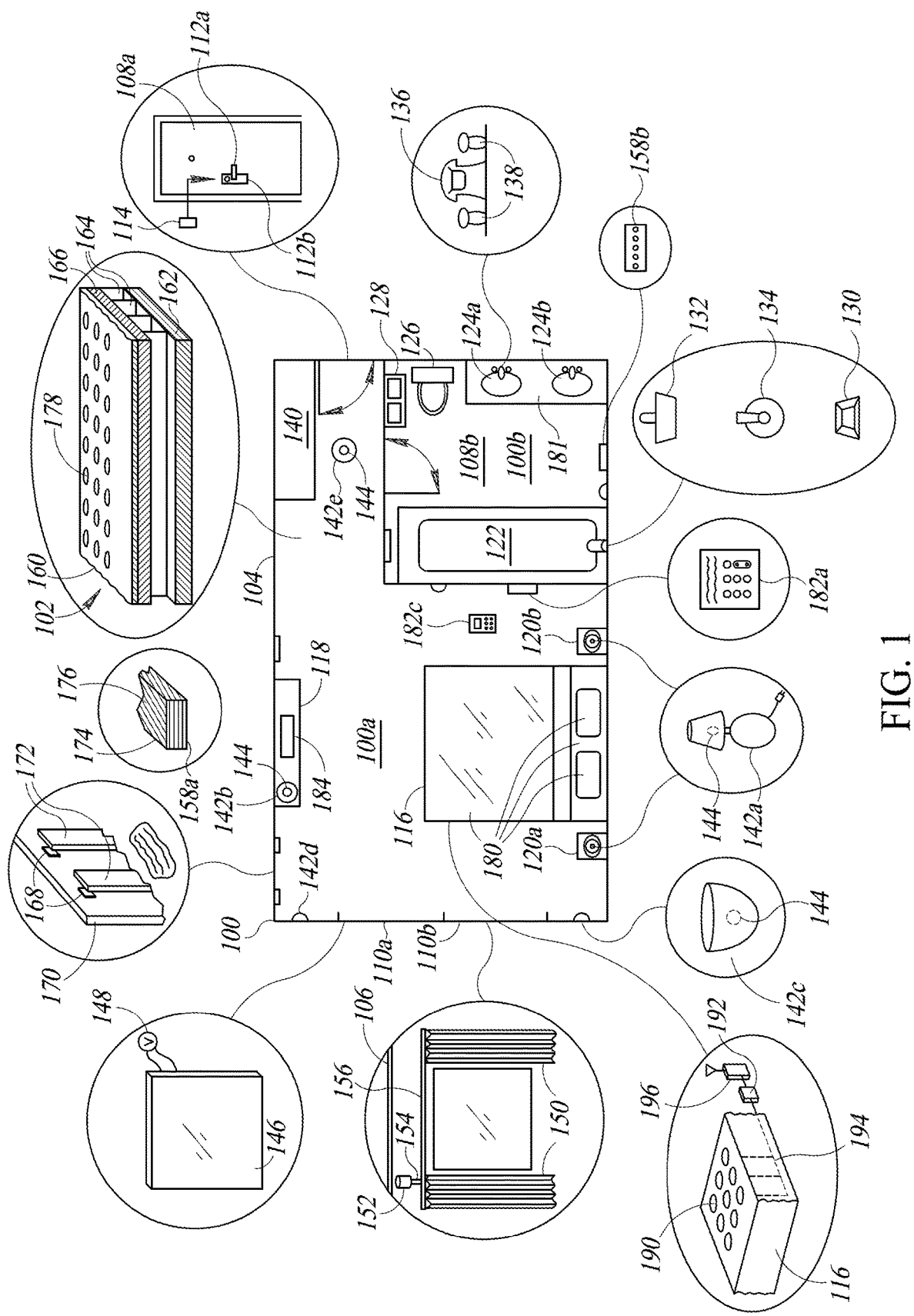
FIG. 1 is a schematic diagram of a habitable environment according to one illustrated embodiment, including enlarged views of various elements or components of the habitable environment.

FIG. 1 shows a habitable environment 100, according to one illustrated embodiment in which various apparatus, methods and articles described herein may operate.

The habitable environment 100 may take the form or one or more enclosed spaces, such as one or more rooms, for instance, in a house, hotel, spa, condominium unit, apartment, office, hospital, vehicle or other accommodation which people typically occupy, inhabit or frequent. The habitable environment 100 may in some implementations be an indoor environment and/or an outdoor environment.

The habitable environment 100 includes a floor system 102, wall system 104, and ceiling system 106, and may include one or more doors 108a, 108b (collectively 108) and/or windows 110a, 110b (collectively 110). The doors 108 may provide ingress and egress to an exterior environment, or may provide ingress and egress to other enclosed spaces within the habitable environment 100. For instance, one door 108a may provide passage between the habitable environment 100 and a hallway (not called out) outside of the habitable environment 100. Another door 108b may provide passage between one portion and another portion of the habitable environment 100, such as between a bedroom or living area 100a and a bathroom 100b.

The door 108a to the exterior may have a handle 112a with associated lock, for instance, a cardkey entry lock 112b. The cardkey entry lock 112b reads an identifier either encoded in a magnetic stripe or in a wireless transponder (e.g., radio frequency identification (RFID) transponder or smartcard) of a cardkey 114. The identifier may be logically associated with an inhabitant or occupant of the habitable environment 100. For example, a hotel guest may be assigned to a given suite, and issued a cardkey 114 that provides access to the suite. The identity of the guest may be stored in a database or other data structure with a logical relationship (e.g., key, pointer) to the suite. Likewise, various attributes of the guest may be stored in the database or other data structure, logically associated with the identity of the guest. As explained below, this may allow various aspects of the environment of the habitable environment 100 to be customized for the particular occupant.

As illustrated, the habitable environment 100 may be a suite, with a combined sleeping and living area 100a, and a separate bathroom 100b. The habitable environment 100 may include various pieces of furniture or fixtures. For example, the habitable environment 100 may include a bed 116, dresser 118, and end tables 120a, 120b (collectively 120). Also for example, the habitable environment 100 may include a bathtub or shower 122, sinks 124a, 124b (collectively 124), commode 126 and optionally towel racks 128 in the bathroom portion 100b. The bath or shower 122 may have a faucet 130, a showerhead 132 and a control handle 134. The control handle 134 is operable to control a flow of water via the faucet 130 and/or the showerhead 132, from a supply of water (not shown in FIG. 1). The sink(s) 124 may have a faucet 136 and control handle(s) 138. The control handle(s) 138 is operable to control a flow of water via the faucet 136 from a supply of water (not shown in FIG. 1). The habitable environment 100 may additionally include one or more closets 140.

The habitable environment 100 may include a number of components (e.g., devices, articles, structures) which contribute to a wellness or sense of wellness of the occupant of the habitable environment 100. Some of these components are active components, driven in response to commands or signals, while other components are passive components. These components are brought together as a system, in order to provide synergistic results, thereby enhancing the health, wellness or sense of well-being of an inhabitant or occupant of a habitable environment or enclosed space. The various components are discussed below with reference to FIGS. 1 and 2, and exemplary operation of such are discussed below with reference to FIGS. 3-11.

The habitable environment 100 may include a number of active components operable to achieve desired environmental characteristics, for example, related to illumination, heating, ventilation and air conditioning (HVAC), water treatment, and acoustics.

Controlled lighting or illumination is one aspect of achieving the desired environmental characteristics of the habitable environment 100. Thus, the habitable environment 100 may include a number of artificial luminaires 142a-142e (collectively 142), which are controlled to produce desired output, for example, by varying intensity and/or composition of wavelengths or color. Luminaires 142 may take a variety of forms, for example, lamps (e.g., tabletop, floor standing) 142a, 142b, sconces 142c, 142d, and/or overhead lighting 142e. The luminaires 142 may employ a variety of illumination sources 144, for example, incandescent lights, fluorescent lights, compact fluorescent lights, and light emitting diode (LED) lighting. The luminaires 142 may optionally include ballasts (e.g., electronic ballasts) and/or other electrical or electronic components required for operation. The luminaires 142 may also include various passive and/or active thermal management components to remove heat, thereby prolonging the operational life of the luminaires 142. Each luminaire 142 may include a plurality of individual illumination or light sources 144, respective ones or sets of the illumination sources 144 operable to emit light in a respective range of wavelengths. Some of the ranges may overlap, while other ranges may or may not overlap. The ones or sets of the illumination sources 144 may be individually operable to achieve any desired distribution of wavelengths at any given time. Each luminaire 142 may include one or more intensity adjustment circuits (e.g., dimmer circuits), which may take a large variety of forms depending on the type of illumination sources 144 employed. For example, an adjustable resistance type dimmer switch may be employed with incandescent sources, while a more sophisticated pulse width modulation technique may be used to control intensity of LED sources.

The habitable environment 100 may additionally or alternatively include a number of components which are controlled to adjust natural light being received in the habitable environment 100 via one or more windows 110 from an exterior thereof, for example, from a natural source of light (e.g., the sun). These may include "smart" panes or electrochromatic panes 146 in the window 110a and associated actuator, for instance, a voltage source 148 coupled to control a transmissivity of the electrochromatic panes 146. Electrochromatic panes 146 may commonly be referred to as electrochromatic glass, but the embodiments herein are not intended to be limited to glass. These may include one or more drapes, shades or curtains or other window coverings (collectively window covering 150) and an actuator such as an electric motor 152 coupled by a transmission 154 to drive the window covering along a track 156 relative to the window(s) 110b. Electrochromatic panes 146 may include glass, mirror or other material which is controllably or selectively transmissive of a light some wavelengths in response to a stimulus, for instance, in response to an applied signal such as an applied voltage and/or applied current. For example, electrochromatic panes 146 may be generally or substantially transparent to various wavelengths (e.g., white light) in response to a first signal, and generally or substantially opaque to various wavelengths (e.g., white light) in response to a second signal, different from the first signal. The electrochromatic panes 146 may be adjustable to control the intensity of light which is substantially passed or substantially blocked, and/or control wavelengths which are selectively substantially passed or substantially blocked. The electrochromatic panes 146 may utilize any suitable technology including, but not limited to, electrochromic, photochromic, thermochromic, suspended particle, microblind or liquid crystal devices.

HVAC is another aspect by which the desired environmental characteristics of the habitable environment 100 may be achieved. Thus, the habitable environment 100 may include a number of vents 158a-158b (only three shown, collectively 158) that provide air to the habitable environment 100 or portions thereof having desired air temperature, humidity, and/or air quality. At least one of the vents 158 may selectively supply scent(s) to the habitable environment 100 or portion thereof. Architectural solutions may be employed to work in tandem with an HVAC system and related devices to synergistically improve air quality. For example, an air displacement system in which cool air flows into a space near the floor and displaces existing air through vents in the ceiling can improve performance for HVAC and air purifier devices.

Likewise, water is yet another aspect by which the desired environmental characteristics of the habitable environment 100 may be achieved. Thus, the habitable environment 100 may include a number of faucets 130, 136 and/or showerheads 132 which supply water which has been treated in a variety of ways to enhance wellness.

The habitable environment 100 may include a number of passive components to achieve desired environmental characteristics, for example, related to flooring system 102, wall system 104, ceiling system 106, acoustics, air quality (e.g., zero or low volatile organic compound (VOC) emitting), and hygiene or sanitation (e.g., anti-pathogen). Many of these are discussed below.

The habitable environment 100 may include flooring system 102, wall system 104, ceiling system 106 and/or bed 116 designed to achieve a variety of benefits. For example, the flooring system 102, wall system 104 and/or ceiling system 106 may be designed to reduce exposure to noise.

Loud environments have become a part of modern life. Fans, overhead planes, passing traffic, and loud neighbors all contribute to ambient noise conditions in the home. About half of Americans live in areas where background noise is above 55 decibels (dB)—a level that most consider bothersome. On the logarithmic decibel scale, 0 dB is the point where sounds become discernible to the human ear, and every increase of 10 dB increases the sound pressure level by a factor of 10. Regular exposure to 85 dB for over eight hours at a time can lead to permanent hearing loss. In outdoor urban spaces not immediately adjacent to any sound generators the background noise is often close to 40 db. The World Health Organization recommends an ambient sound level of under 45 dB inside homes and 30 dB for bedrooms.

Thus, the habitable environment 100 may include various passive approaches to achieve the benefit of reduced noise.

Much of the bothersome noise in homes originates from the outside, so acoustic barriers are an important part of overall sound balance. Many of the same technologies that provide effective thermal insulation in walls and windows concurrently block noise. This allows for acoustic protection solutions, while incurring little additional cost. In addition, floor lining reduces sound transmission between apartments and improves perceptions of privacy.

For example, the habitable environment 100 may include a flooring system 102 designed to achieve a variety of benefits. The flooring system 102 may include floor covering 160, subflooring 162, and optionally acoustically damping floor mounts 164 coupling the flooring 160 to the subflooring 162. The flooring system 102 may include one or more additional layers of flooring 166, which provides a resilient member or layer(s) (e.g., cork), as discussed below. The flooring system 102 may include baffle material or insulation (not illustrated), for instance, between the additional layer of flooring 164 and the subflooring 162. The flooring system 102 may additionally or alternatively include pads or sheets of material (not shown) that acoustically isolate sources of vibration (e.g., vibrating appliances such as washing machines). The flooring system 102 may additionally or alternatively include impact-resistant engineering or elements, specifically designed to lessen a force experienced in the event of a fall by a person.

The flooring system 102 uses non-toxic, natural materials that are intended to absorb the sound of footfalls and other vibrations, and provide isolation from exterior or interior sound.

Also, for example, the habitable environment 100 may include a wall system 104 designed to achieve acoustic damping. The wall system 104 may include specially constructed walls which incorporate resilient channels 168, double-wallboard or sheetrock 170, double-studs 172, and acoustic insulation designed to decrease sound transmission. The resilient channels 168 resiliently couple the double-wallboard or sheetrock 170 to the double-studs 172 to reduce transmission of vibration.

As another example, the habitable environment 100 may employ acoustically damping doors 108. For instance, solid oak doors that tightly seal to a door frame may achieve sound reduction on par with well-constructed walls.

As a further example, the habitable environment 100 may employ acoustic damping windows 110. For instance, triple glazed windows 110 with vacuum or rare earth gases trapped therebetween may minimize sound transmission from the exterior.

As yet a further example, the habitable environment 100 may employ acoustically damping plumbing insulation 174. For instance, non-toxic blankets of acoustically damping material 174 may be wrapped around water pipes (not shown) and air ducts 176 to reduce the sound transmitted by metal conduits.

The health effects of flooring have become the focus of a growing number of studies. Research shows that standing on surfaces without any give or cushioning for extended periods of time forces muscles into a constant state of flexion. This decreases circulation, promotes bad posture, causes lower back pain and can lead to orthopedic ailments. Cushioned mats decrease the impact on joints and promote muscle relaxation.

The habitable environment 100 may employ a cushion-lined flooring system 102 in order to realize a number of benefits, including increased circulation and promotion of healthy posture. The result may be fewer reports of joint pain, discomfort, and low energy. In addition, standing on softer surfaces decreases the risk of developing plantar fasciitis, and can alleviate symptoms for those already suffering from the condition. The flooring system 102 should be soft or resilient enough to allow for underfoot comfort, yet strong enough to improve lumbar support. The flooring system 102 consists of floating construction, for example, with cork under layer(s) 166 to reduce forces generated from impacts by increased deflection.

Reflexology is a traditional practice of massage, which aims to reduce the symptoms of various ailments. Practitioners use stimulation of specific areas of the hands and feet to reduce tension and stress. Evidence has shown that the practice of reflexology has powerful anxiety reduction with reduced blood pressure and pulse rates. The habitable environment 100 may employ a custom-designed pathway (e.g., bathroom pathway), with textured floor covering 178, designed to improve blood circulation and general well-being by encouraging reflexology therapy.

Due to large surface area, floor finishing can often be a major source of VOCs. The habitable environment 100 uses natural flooring materials chosen to reduce the emissions of harmful indoor air pollutants and volatile organic compounds.

Electromagnetic fields (EMF) are created when charged particles are in motion. The movement of electrical charge through wires and appliances creates electromagnetic fields. The strength of the electric field depends on the voltage (e.g., typically 120 V for households) and is present near live wires, whether or not an electrical appliance is in use. Research suggests that long-term and significant occupational exposure to EMFs may increase the risk of both Alzheimer's disease and breast cancer.

Thus, EMF shielding is incorporated into the habitable environment 100. The EMF shields are designed to block the spread of the electric field by creating a barrier composed of conductive or magnetic materials. EMF shields have traditionally been made out of solid metal, though this poses challenges regarding weight, corrosion, and malleability. Treated metal mesh or screens with openings smaller than the electromagnetic wavelength may provide a more practical solution.

Thus, for example, the habitable environment 100 may include EMF shielding for wiring. In particular, wiring may be insulated with foil wraps designed to shield EMF from occupied parts of the habitable environment 100. Also for example, low EMF electrical wiring may be employed.

Another passive approach takes advantage of anti-bacterial or anti-pathogen (i.e., "treated") materials to reduce or eliminate the presence of bacteria or pathogens. The anti-bacterial or anti-pathogen materials may be incorporated into or deposited on bedding (e.g., sheets, bedspreads, throws, pillows, pillow covers) 180, window coverings (e.g., drapes, shades, curtains) 150 and/or surfaces (e.g., counters 181, tubs or shower stalls 122, table tops 120, walls 104). For example, various materials may be impregnated with or coated with anti-bacterial or anti-pathogen materials. These materials may have opening or pore sizes on the order of 1 micron, providing an effective barrier against penetration by various undesirable particles. Any seams in the bedding should be sealed. At least in the case of bedding, these materials preferably completely encase or envelope mattress, box springs, pillows, and/or comforters. Such may provide protection against bedbugs, allergens, and/or dust mites.

Examples of suitable materials may contain or include, silver (Ag) in ionic form, which has proven effective against a variety of pathogens. Additionally or alternatively, other non-toxic antimicrobials may be employed, for instance, silane quaternary ammonium compounds and/or zinc pyrithione.

In order to reduce exposure to pathogens and toxins without excessive use of chemicals or cleaning, the amenities below lower the effort required in maintaining a healthy environment.

As a further example, titanium dioxide nanoparticles have emerged as an effective means of reducing air pollutants through photocatalyst which creates a self-cleaning surface powered by ambient light exposure. For example, the nanoparticles may catalyze a reaction converting VOCs to harmless carbon dioxide. Such may be incorporated into a photo-catalytic coating which may be used on walls to break down bacteria, viruses, and VOCs when exposed to light.

The habitable environment 100 may include anti-bacterial or anti-pathogen materials as structural materials. For example, cedar may be employed in closets and/or used as baseboards. Certain species of cedar act as a natural pest control, repelling many insects. Oils present in cedar wood have been shown to repel fungi (such as mold), bacteria, insects, termites and ticks.

Figure 2:
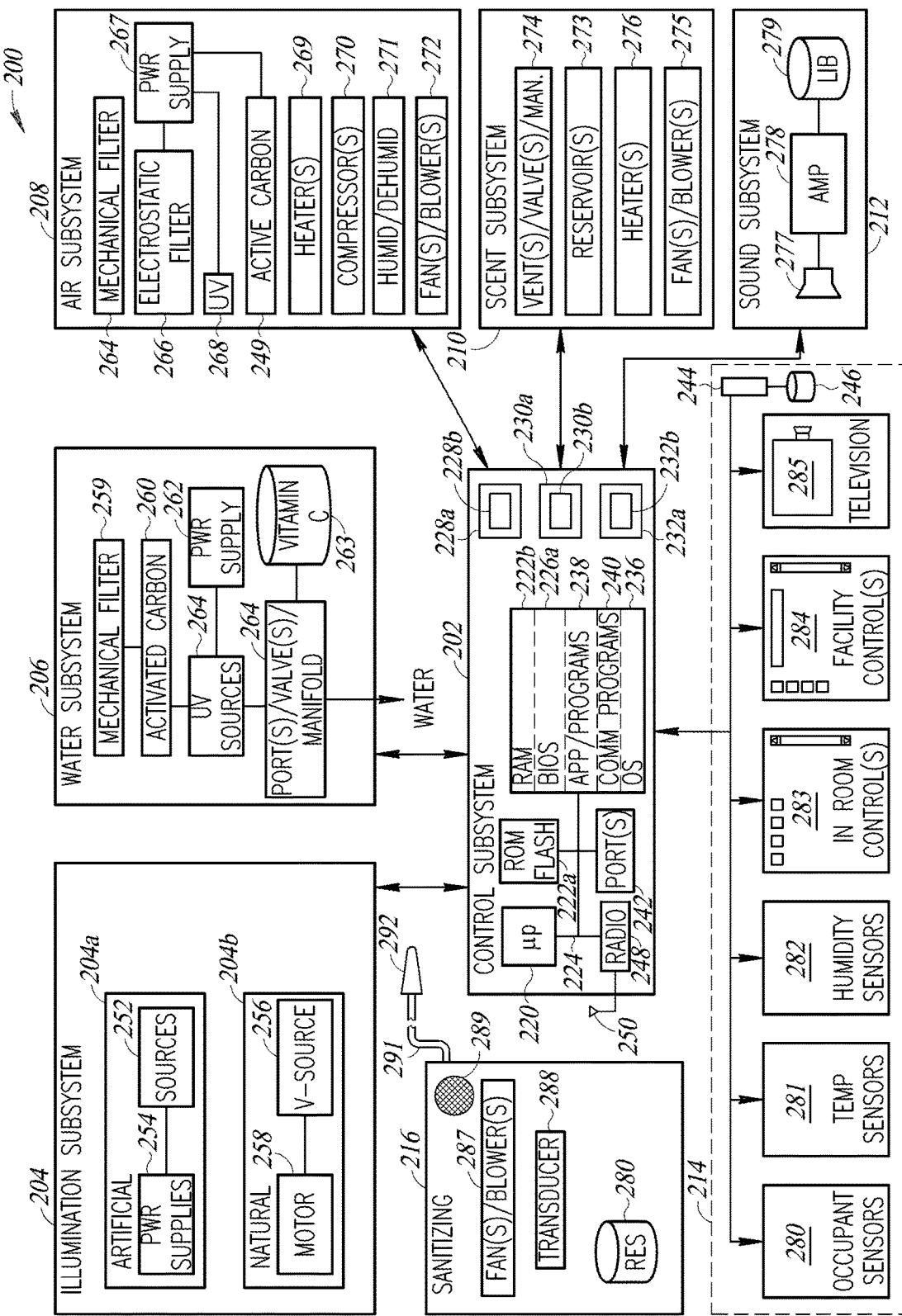
FIG. 2 is a block diagram that shows a portion of a habitable environment enhancement system to enhance a habitable environment, according to one illustrated embodiment.

The bed 116 and associated bedding may be designed to enhance wellness in a variety of ways. For example, the bed 116 may include a plurality of sensors 190 operative to detect one or more characteristics. In some implementations, the sensors 190 detect at least one of pressure, motion or temperature. The sensors 190 may be operatively coupled to a multiplexer 192 via suitable wired or wireless couplings 194 (e.g., electrical wire). The multiplexer 192 may be coupled to a wireless transceiver 196 that communicates sensor data from the sensors 190 to one or more computing devices, such as one or more user operable input/output (I/O) devices, controls, panels or kiosks 182, or a control subsystem 202 (FIG. 2).

One or more queries associated with the bed 116 may also be provided to a user through a suitable interface, such as one or more user operable I/O devices, controls, panels or kiosks 182, or control subsystems.

The bed 116 may also include one or more controllable actuators that adjust a physical characteristic of the bed. For example, the bed 116 may include a plurality of controllably inflatable members that may be used to selectively adjust a firmness of the bed 116. The control subsystem 202 may selectively adjust one or more of the controllable actuators based on information received from the sensors 190 or from other data sources (e.g., survey results) that may be relevant to sleep quality or wellness in general.

The sensors 190 may also be used to provide feedback to the user regarding one or more sleeping habits, such as whether the user primarily sleeps in a prone (stomach) position, lateral (side) position, or supine (back) position. The sensors 190 may also be used to provide feedback to the user regarding movement of the user, which may indicate one or more characteristics of the user's wellness.

There are five major types of mattresses: innerspring, foam, latex, air, water and futon. There is variation in nearly every conceivable metric within and among each of these types, making sufficient clinical and survey-level data for sleep and musculoskeletal health across each practically infeasible. Online surveys reveal memory foam, latex, and air mattresses have higher owner satisfaction (78-81%) compared with innerspring (62%). Owner satisfaction was based on a host of different metrics. These averaged numbers must be qualified, however, given clinical reports that innersprings can lead to substantial improvement in sleep quality. Additionally, it has been observed that acute back pain may result when switching to foam mattresses, which was subsequently relieved upon switching back to a regular cotton mattress. However, it has also been observed that people sleeping on both a high-quality innerspring mattress and a unique foam support mattress found one sleep-quality metric associated with insomnia to be significantly reduced in those sleeping on the foam mattress, suggesting better recuperation.

The inconsistency of the above findings is indicative of the diverse interactions between mattress types and anthropometric variation among test subjects. Thus, comparing mattresses according to broadly defined categories is less useful than an examination of the relationship between performance-based mattress qualities, (e.g., firmness) and measurable health responses.

Mattresses are known to have an impact on spinal recovery and sleep quality, two vital aspects of health.

One of the simplest and most studied mattress-characteristics believed to affect spinal health and sleep quality is overall firmness. The limited number of scientific reports investigating mattress firmness and sleep quality seem to agree that, in general, mattresses must neither be too firm nor too soft. It has been observed that significant improvements in physical pain, sleep comfort and sleep quality result when replacing existing mattresses with new "medium-firm" ones. It has also been observed that medium-firm mattresses reduce pain-related disability more than firm mattresses in patients with chronic, nonspecific low-back pain. Further, while softest and the firmest mattresses are associated with worsened pain and sleep, there is still high variation among individuals' sleep quality response within the mid-range firmness levels. It has further been observed that on a firm surface, people assumed a posture between lateral and prone, presumably in order to avoid the lateral bending when the shoulder and pelvis are not allowed to sink into the surface. This bending was less extreme than on a soft surface, however, when the pelvis sinks too far into the mattress, the spine bends even further in the frontal plane than on a firm mattress.

It is assumed in most sleep studies that spinal alignment, contact pressure and sleep quality are always positively associated with one another, however, this may be an overly simplistic assumption. One study measured both contact pressure and spinal alignment to evaluate four "top of the line" mattresses in a male population. The study reported significant differences between mattresses, but the pattern of results was not consistent; the mattress with the highest maximal contact pressure tended to have the lowest spinal distortions. The impact on sleep was not incorporated in the study. Interestingly, another study found that spinal alignment was greater in the mid-range to higher firmness levels.

One study did find differences in sleep architecture, with significantly more slow-wave sleep (SWS) and higher sleep efficiency on 'comfortable' than on 'uncomfortable' mattresses. However, the study did not provide quantitative characteristics to describe the meaning of 'comfortable' and 'uncomfortable'. These studies suggest that two central aims of a mattress, to exhibit low maximum pressures and minimize spinal distortion may in fact be at cross-purposes. Although pressure distribution is the primary concern for the prevention of pressure ulcers in bedridden patients, it is sufficient merely to avoid concentrated pressure peaks in a healthy population. Thus, experts generally tend to give preference to a sleeping position that allows the spine to be kept in a neutral and elongated position.

Sleep is essential for allowing the body's muscles and intervertebral discs to recover from continuous loading throughout the day. Intervertebral disc (IVD) volume increases 20-25% at night, regenerating the discs' ability to support gravity-induced compression the following day, and injecting nutrients into the spinal column. This process is most efficient when the spine is allowed to remain in a neutral position. It is also possible that spinal health and sleep quality (not merely duration) are also intrinsically linked; it has been hypothesized that REM, and non-REM phases play important and perhaps complementary roles in efficient IVD decompression during sleep.

There are three major types of sleeping positions, prone (stomach), lateral (side), and supine (back). Though many studies have examined various sleep effects associated with each, little research has been conducted to examine how mattress types affect different sleep positions. When sleep quality and spinal alignment across two bed types, a sagging spring mattress, and a customizable air-chamber mattress, was examined, it was found that prone sleepers were more negatively affected by a sagging bed and additionally saw a more significant increase in sleep quality when switching to a customized air-chamber bed, when compared with supine sleepers, who reported no difference between the two bed types.

The consideration of sleep posture is further complicated by the fact that all sleepers shift positions several times throughout the night; in-fact, this natural shifting is thought to be an important feature of healthy sleep. The ideal amount of sleep movement, however, is unknown. One study found that although some activity and posture change is normal, relatively turbulent sleep relates to a reported worse sleep quality. Furthermore, there is evidence that the average proportion of various sleeping positions assumed changes with age: Whereas in children, prone, supine and lateral positions were assumed to occupy an equal proportion of sleep time, there is a significant progressive disappearance of prone positions with age, and preference for right-side positions in the elderly.

An association between side-predominant sleepers and lower shoulder and back pain has been observed. However, this correlation does not necessarily indicate that sleeping position is the primary cause of back pain; it is conceivable that those with back and/or shoulder injuries might naturally assume lateral positions, depending on the type of injury. Regardless, if a mattress is observed to change one's natural sleeping position from prone or supine to lateral, it could improve sleep quality.

In light of the complex interactions between individual physiology and mattress performance, it is little wonder that people are unable to choose the best mattress for themselves. Even when customers are allowed to assess bed comfort in a 15-minute evaluation, the customers did not accurately select the mattress type that would later be shown to minimize morning pain and stiffness, and optimize sleep quality and daytime energy levels.

The results of most mattress investigations suggest that while the extremely soft or firm mattresses are worse on average than medium-firm mattresses, there is high variance in the degree of mattress firmness necessary to reduce an individual's morning pain and optimize their sleep quality. The variation in mattress efficacy across individuals suggests that mattress firmness and perhaps even the goal of maintaining a neutral spine may be over-simplifying the problem. Interactions between various mattress qualities, and physiological measurements such as weight, height, BMI and preferred sleeping position all contribute to the observed variation in spinal distortion, pressure distribution and sleep-quality among individuals.

Given the high individual variation in posture type, anthropometrics, and poor correlation between initial comfort evaluation and objective sleep measurements, the need becomes apparent for an individualized, objective evaluation of spinal alignment, pressure distribution, and, ideally, sleep-quality performance for a variety of mattress configurations. Therefore, for example, the bed 116 may be able to detect posture changes using the sensors 190 and, in a second step, actively change its mechanical properties to optimize spinal support for each assumed posture; in essence, an 'active' sleep system. Due to the cost and inefficiency inherent in such a recommendation, however, it may be more practical to use anthropometric metrics for predicting optimal mattress configurations wherever possible. Alternatively, mattresses that are designed to automatically adjust based on weight-distribution, such as air-mattresses with air-bladder compartments, or an innerspring with customizable firmness "zones" may not require an advanced sleep-monitoring analysis to achieve an adequate measure of performance.

Temperature is another important contributor to sleep quality. Memory foam in particular tends to absorb and retain heat, which may interfere with sleep. A strong link between sleep and thermoregulation has been observed. Human core body temperature naturally cycles in a 24-hour period and is linked with the circadian rhythm and sleep-wake cycles. Before and during sleep, skin temperature increases and core temperature decreases with increased peripheral blood flow. Even mild heat exposure during sleep can increase wakefulness, decrease REM sleep and slow-wave sleep. Humid heat exposure further increases wakefulness, decreases REM and SWS, and excessively suppresses the decrease in core body temperature. Temperature sensitivity depends largely on age and acclimatization to local conditions. Generally, as long as sweating is avoided, major sleep disturbances are avoided.

Many mattresses may contain chemicals that are known to cause respiratory problems and skin irritation. Volatile organic compounds (VOCs) are emitted gases that have been associated with a number of short- and long-term adverse health effects including eye, nose, and throat irritation, headaches, nausea, liver, kidney and central nervous system damage.

Foam mattresses, which are traditionally made of petroleum, may contain up to 61 different VOCs. Toxic chemicals may be found in the core, padding, flame-retardant material, the cover, or the joints of mattresses. Even non-petroleum based mattresses may contain toxic chemicals. Formaldehyde and Benzene, still found in many mattress varieties, are regulated as probable human carcinogens by the EPA. Many mattress makers use one or more chemicals of concern, including antimony, vinyl, polyurethane, and other VOCs; vinyl coverings; proprietary formulas for waterproofing, flame retardants or antibacterial chemicals. While some manufacturers offer "green" components, they do not appear to take meaningful steps to ensure products are free of all toxic chemicals. Additionally only a small fraction of mattress manufacturers avoid potential allergens.

Mice exposed for 1-hour to six brands of waterproof crib mattresses caused various combinations of sensory irritation, pulmonary irritation, and decrease in airflow. Gas chromatography revealed the mattresses emitted mixtures of chemicals known to cause a variety of acute toxic effects, including asthma-like reactions.

Major leading brands of mattresses do not divulge which flame-retardant chemicals they use, claiming they are trade secrets. Complaints of "off-gassing" smells from traditional foam mattresses are still common, and can last for several weeks.

Thus it is important to select specific brands and mattress varieties that minimize or omit any noxious gases that may impact allergies, or pose even more serious health risks.

Exposure and sensitization to house dust mite (HDM) allergens has been established as an important risk factor for the development of asthma in most parts of the world. The amount of dust-mite exposure increases the risk developing an allergy, and the severity of the response once an allergic response is developed. Asthma symptoms are more severe in patients who are exposed to higher allergen levels, including dust mites.

In addition to mattress cover and materials, design also plays an important role. The smaller the surface area, both inside and outside of the mattress, the fewer spaces to trap dust and the lower the overall dust mite population. Mattresses that allow some degree of ventilation throughout the interior may also reduce moisture buildup that can harbor dust and mold.

Mattress durability and longevity is important for reducing the cost of replacement, and ensuring optimal performance throughout its expected lifetime. Air beds tend to have low durability, but high longevity. This is because the air pumps that support them can malfunction or be damaged, but given that the problem is fixed, the materials in an air mattress can last up to 10 years. Latex mattresses are also known to have good longevity, with an average of about 7 years. Memory foam averages around 6 years, while futon and inner spring mattresses rarely last beyond 5 years.

Most people use pillows when they sleep at night, and therefor are an important consideration in spinal alignment. While it is true that some people may be more comfortable without a pillow, this may cause for poorer or better spinal alignment than with a pillow, depending on mattress type, body type and sleeping position. In fact, pillows have been designed specifically to meet the needs of various kinds of sleepers. For example, body pillows, knee pillows and ergonomic head pillows are commercially available.

A rating system may be employed to facilitate mattress and/or bedding selection. The rating system may include three categories, progressively from lowest to highest denominated as: 1) basic certification, 2) silver certification, and 3) gold certification.

For example, with respect to firmness and spinal support to qualify for basic certification a foam mattress must have an ILD rating between 13 and 16, be between 3-4" thick, and have a density of between 3 and 5 lbs per ft². While to qualify for basic certification a spring mattress must have a coil density of at least 800 pocketed springs, and feature a foam edge support. To qualify for silver certification, a foam mattress must have an ILD rating between 13 and 16, be between 3-4" thick, and have a density of at least 5 lbs per ft². To qualify for silver certification, a spring mattress must have a coil density of at least 900 linear pocketed springs, foam edge support, and additionally must have at least five compartmentalized zones, divided by positioning at the shoulder, waist, hips and legs. The spring mattress must have linear pocketed springs that are 15-30% less stiff in the shoulder and hip zones. Meanwhile, to qualify for silver certification, an air mattress must have an adjustable internal pressure between 1,000 and 4,000 Pa.

Also, for example, with respect to toxicity to qualify for basic certification a mattress must conform to all sections of CertiPUR-US certification. To qualify for silver certification, a mattress must conform to the strictest certification class of OEKO-Tex 100 testing criteria (Limit 1 Values), and where CertiPUR-US levels are stricter, the mattress must meet those stricter criteria. To qualify for gold certification, a mattress must have a total VOC emission not exceeding 0.001 ppm.

Also, for example, with respect to asthma and allergies to qualify for basic certification a mattress must be constructed without grooves, pockets or indentations on the outer surface. To qualify for silver certification, a mattress must be free of all potentially allergenic materials, including wool and natural latex.

Also, for example, with respect to temperature control to qualify for basic certification a foam mattress must have a ventilation layer. To qualify for silver certification, a mattress must have adequate ventilation to maintain humidity levels below 60% at standard pressure, 25° ambient temperature and 50% Relative Humidity, between the surface of the mattress and exposed human skin over a 30-minute period.

An ability to control a function or operation of at least the active components may be useful in realizing the amenities and benefits offered in the habitable environment 100. Thus, a number of user operable input/output (I/O) devices, controls, panels or kiosks 182 may be supplied.

For example, an in-room user operable I/O panel or dashboard 182a may include a display (e.g., LCD) to display information. The in-room user operable I/O panel 182a may include user actuatable controls (e.g., user selectable icons displayed on touch screen, keys, buttons) manipulation of which allows a user, for instance, an occupant of the habitable environment 100, to select parameters or programs to execute to control one or more of the environmental characteristics of the habitable environment 100.

Also, for example, a mobile or handheld device 182c may serve as an I/O device. The mobile or handheld device 182c may include a display (e.g., LCD) to display information and user actuatable controls (e.g., user selectable icons, keys, buttons), manipulation of which allows a user, for instance, an occupant of the habitable environment 100 or facility personnel, to select parameters or programs to execute to control one or more of the environmental characteristics of the habitable environment 100. The mobile or handheld device 182c may be owned by the end user, for example, the occupant. The mobile or handheld device 182c may execute a downloaded customized application or "app" that communicatively interfaces via a wireless protocol (e.g., IEEE 802.11, BLUETOOTH®, WI-FI®).

Alternatively or additionally, a remote user operable I/O controls, panel or kiosk 283 (FIG. 2) may include a display (e.g., LCD) to display information. The remote user operable I/O controls, panel or kiosk 182c may include user actuatable controls (e.g., user selectable icons displayed on touch screen, keys, buttons) manipulation of which allows a user, for instance, personnel of the facility in which the habitable environment 100 is located, to select parameters or programs to execute to control one or more of the environmental characteristics of the habitable environment 100.

Information about the amenities and benefits afforded by the wellness system in the habitable environment 100 may be useful in realizing the benefits of such. Information may be provided via a server and presented via a variety of devices. For instance, information may be presented via a television 184, for instance, on a dedicated channel, via in-room or other display, panel or kiosk 182a, via handheld device 182c, etc.

FIG. 2 shows an active portion of an environmental control system 200 for controlling environmental characteristics of a habitable environment 100 (FIG. 1), according to one illustrated embodiment. FIG. 2 provides a more detailed representation of some of the components of FIG. 1.

The active portion of an environmental control system 200 includes a number of subsystems. For example, the active portion may include a control subsystem 202, illumination subsystem 204, water treatment subsystem 206, air treatment subsystem 208, scent subsystem 210, sound subsystem 212 and input/output (I/O) subsystem 214. The active portion may optionally include a sanitizing subsystem 216, which, as described below, may be either built in or a fixture of the habitable environment 100, or may be portable, being located in the habitable environment 100 only during use. Each of the subsystems 202-216 and/or components is discussed in turn below with reference to FIG. 2.

The control subsystem 202 may take the form of a programmed computer or other processor-based system or device. For example, the control subsystem 202 may take the form of a conventional mainframe computer, minicomputer, workstation computer, personal computer (desktop or laptop) or handheld computer.

The control subsystem 202 may include one or more processors or processing units 220 (one illustrated), non-transitory processor-readable system memories 222a-222b (collectively 222) and a system bus 224 that couples various system components including the system memory 222 to the processing unit(s) 220. The processing unit(s) 220 may be any logic processing unit, such as one or more central processing units (CPUs), digital signal processors (DSPs), application-specific integrated circuits (ASICs), field programmable gate arrays (FPGAs), programmable logic controllers (PLCs), artificial neural network circuits or systems or any other logic components. Non-limiting examples of commercially available computer systems include, but are not limited to, an 80×86, Pentium, or i7 series microprocessor from Intel Corporation, U.S.A., a PowerPC microprocessor from IBM, a Sparc microprocessor from Sun Microsystems, Inc., a PA-RISC series microprocessor from Hewlett-Packard Company or a 68xxx series microprocessor from Motorola Corporation. The system bus 224 can employ any known bus structures or architectures, including a memory bus with memory controller, a peripheral bus and a local bus. The system memory 222 includes nontransitory Flash or read-only memory ("ROM") 222a and nontransitory random access memory ("RAM") 222b. A basic input/output system ("BIOS") 226a, which can form part of the ROM 222a or RAM 222b, contains basic routines that help transfer information between elements within the control subsystem 202, such as during start-up.

The control subsystem 202 may include a hard disk drive 228a for reading from and writing to a hard disk 228b, an optical disk drive 230a for reading from and writing to removable optical disks 230b, and/or a magnetic disk drive 232a for reading from and writing to magnetic disks 232b. The optical disk 230b can be a CD/DVD-ROM, while the magnetic disk 232b can be a magnetic floppy disk or diskette. The hard disk drive 228a, optical disk drive 230a and magnetic disk drive 232a may communicate with the processing unit 220 via the system bus 224. The hard disk drive 230a, optical disk drive 230a and magnetic disk drive 232a may include interfaces or controllers (not shown) coupled between such drives and the system bus 224, as is known by those skilled in the relevant art. The drives 228a, 230a, 232a, and their associated computer-readable storage media 22b, 230b, 232b, may provide nonvolatile and non-transitory storage of computer readable instructions, data structures, program engines and other data for the environmental control system 200. Although control subsystem 202 is illustrated employing a hard disk 228a, an optical disk 230a and a magnetic disk 232a, those skilled in the relevant art will appreciate that other types of computer- or processor-readable storage media that can store data accessible by a computer may be employed, such as magnetic cassettes, flash memory, digital video disks ("DVD"), Bernoulli cartridges, RAMs, ROMs, smart cards, etc. The hard disk 228a may, for example, contain instructions and data for controlling the other subsystems, for example, based on specific aspects or characteristics of an occupant of the habitable environment 100 (FIG. 1), to provide environmental characteristics that promote the wellness or well-being of the occupant(s). The hard disk 228a may, for example, contain instructions and data for presenting information about the various attributes and benefits provided by the active and passive components or measures, and instructions on how to use the environmental control system 200 and the passive components to maximize enjoyment, comfort, and well-being.

Program engines can be stored in the system memory 222b, such as an operating system 236, one or more application programs 238, other programs or engines and program data. Application programs 238 may include instructions that cause the processor(s) 220 to automatically generate signals to control various of the other subsystems to achieve various environmental characteristics in the habitable environment 100 (FIG. 1), for example, based on one or more aspects, characteristics or attributes of an occupant thereof. Application programs 238 may include instructions that cause the processor(s) 220 to automatically receive input and/or display output via various user operable input/output (I/O) devices, controls, panels or kiosks 182 or television 184.

Other program engines (not specifically shown) may include instructions for handling security such as password or other access protection and communications encryption. The system memory 220 may also include communications programs 240, for example, a server for permitting the control subsystem 202 to provide services and exchange data with other subsystems or computer systems or devices via the Internet, corporate intranets, extranets or other networks (e.g., LANs, WANs), as well as other server applications on server computing systems such as those discussed further herein. The server in the depicted embodiment may be markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers are commercially available such as those from Microsoft, Oracle, IBM and Apple.

While shown in FIG. 2 as being stored in the system memory 222b, the operating system 236, application programs 238, other programs/engines, program data and communications applications (e.g., server, browser) 240 can be stored on the hard disk 228b of the hard disk drive 228a, the optical disk 230b of the optical disk drive 230a and/or the magnetic disk 232b of the magnetic disk drive 232a.

An operator can enter commands and information (e.g., configuration information, data or specifications) into the control subsystem 202 via various user operable input/output (I/O) devices, controls, panels or kiosks 182 or television 184, or through other input devices such as a dedicated touch screen or keyboard (not shown) and/or a pointing device such as a mouse (not shown), and/or via a graphical user interface. Other input devices can include a microphone, joystick, game pad, tablet, scanner, etc. These and other input devices are connected to one or more of the processing units 220 through an interface such as a serial port interface 242 that couples to the system bus 224, although other interfaces such as a parallel port, a game port or a wireless interface or a universal serial bus ("USB") can be used. A monitor or other display device is coupled to the system bus 224 via a video interface, such as a video adapter (not shown). The control subsystem 202 can include other output devices, such as speakers, printers, etc.

The control subsystem 202 can operate in a networked environment using logical connections to one or more remote computers and/or devices as described above with reference to FIG. 1. For example, the control subsystem 202 can operate in a networked environment using logical connections to one or more other subsystems 204-214, one or more server computer systems 244 and associated nontransitory data storage device 246. The server computer systems 244 and associated nontransitory data storage device 246 may, for example, be controlled and operated by a facility (e.g., hotel, spa, apartment building, condominium building, hospital) in which the habitable environment 100 (FIG. 1) is located. Communications may be via wired and/or wireless network architectures, for instance, wired and wireless enterprise-wide computer networks, intranets, extranets and the Internet. Thus, the control subsystem 202 may include wireless communications components, for example, one or more transceivers or radios 248 and associated antenna(s) 250 for wireless (e.g., radio or microwave frequency communications, collectively referred to herein as RF communications). Other embodiments may include other types of communication networks including telecommunications networks, cellular networks, paging networks, and other mobile networks.

Illumination (e.g., electromagnetic radiation or energy with wavelengths in the visible, near infrared (NIR) and/or near ultraviolet (NUV or UVA) portions of the electromagnetic spectrum) can have a significant effect on human health. As used herein and in the claims, the terms illumination or light include energy in the portions of the electromagnetic spectrum which are visible to humans (e.g., approximately 400 nm-approximately 700 nm) and not visible to humans (e.g., NIR or UVA). Light influences the human body in a number of unconscious ways. Metabolism has been deeply linked to the daily solar cycle through melatonin and the endocrine system. This cycle in the human body is called the circadian rhythm. Humans and animals have an internal clock that keeps the body on an approximately 24-hour cycle which matches the Earth's daily solar cycle, even in continuous darkness. Multiple bodily processes, from periods of alertness and sleep to digestion efficiency, are partially regulated by the intensity and color of light received by the eyes. However, light adjusts this internal timing to align the person to the Earth's daily solar cycle. Exposure to light comparable to the intensity of direct sunlight will aid in resetting the circadian rhythm if it has been upset by shift work or long distance travel.

The intensity and color of light impacts different systems of the body. For example, blue light impedes the body's production of melatonin, a chemical messenger used to induce sleep. High intensities in the evening delay sleep, while light in the morning aids in waking. The appropriate brightness and color also contribute to alertness and concentration throughout the day. Melatonin is a natural antioxidant and counteracts the cancer-causing tendencies of free radicals. As a result, melatonin depletion from inappropriate exposure to bright lights leads to an increased risk of cancer. Bright light during midday and dimmer light at dinnertime aid in the digestion of carbohydrates.

Additionally, many individuals suffer from light-related mood irregularities, such as Seasonal Affective Disorder (SAD). Proper exposure to specific types of light at specific times addresses these irregularities. Exposure in the morning to gradual light brightening through dawn simulation has been shown to reduce depression. Daylight aids in the healthy development of eyesight. Myopia in children has been linked with low exposure to daylight and conversely, high reliance on dim artificial light. Age related macular degeneration, or the deterioration of eyesight with age, particularly in seniors with blue eyes, can be minimized by reducing the exposure to high color temperature.

The illumination subsystem 204 may also be controlled to deliver light therapy, with or without topical photoactive substances. Such may, for example, be used to treat a variety of conditions, for instance, Seasonal Affective Disorder (SAD). People who live in high latitudes often experience depression during the winter as a result of long periods of reduced sunlight, a condition identified as SAD. For those affected by SAD, measures of sleep efficiency in the winter are noticeably different from those in the summer. Light therapy may be especially effective at treating SAD, producing results comparable to treatment with medication.

Another condition or syndrome commonly referred to as "jet lag" results from the relative shift between the circadian rhythm and the daily solar cycle. The effects are a disruption of sleep and a significant deterioration in mood, concentration and cognitive performance. Controlled light exposure to help match the solar and circadian light cycles can help alleviate these symptoms.

In some individuals, the body's production or interpretation of melatonin slightly varies relative to the solar cycle, resulting in a set of symptoms identified as Delayed Sleep-Phase Syndrome (DSPS). Approximately one tenth of all adolescents and some adults find themselves falling asleep two to six hours after conventional bedtime. If left undisturbed, these individuals will often sleep soundly for approximately eight hours before waking in the middle of the day. Controlled lighting may help treat DSPS.

Emerging research indicates that different brain activity occurs when the human body is exposed to different parts of the light spectrum. Color can subconsciously affect people's abilities to do different types of tasks. For example, in one study, participants performed analytical tasks better in red light, and were more creative in blue-colored environments.

Research into workplace environments has found that people in brightly colored offices had higher measured emotional status than those in subdued or neutral surroundings. On the other hand, studies have shown that intense colors may be irritating to certain individuals. Chromotherapy employs illumination of certain wavelengths or combinations of wavelengths as an effective manipulator of mood given individual preferences. Practitioners use this therapy to address issues such as meditation, intuition, speech, nervousness and anxiety.

The illumination subsystem 204 may be operated to provide dynamic custom coloring throughout the habitable environment 100 (FIG. 1) or portion thereof in order to provide chromotherapy. Additionally, the habitable environment 100 (FIG. 1) may optionally employ a chromotherapy wall wash in the form of a wall colored by light (e.g., via cover lights or sconces) that dynamically changes color to create a desired light spectrum for different settings and times of day. Additionally or alternatively, chromotherapy lighting can be added to specific areas where colored lights may be more desirable, such as meditation spaces and steam showers.

The illumination subsystem 204 discussed below is used to preserve and remediate the disruption of circadian rhythm, enhancing health, including the natural sleep cycle, the healthy development of the eyes among some attributes and treating or alleviating the symptoms of various disorders, syndromes and/or afflictions. The illumination subsystem 204 may, for example, expose occupants or residents of a habitable environment 100 (FIG. 1) or portion thereof to short periods of intense artificial light for therapeutic effects while subjects are awake as part of delivering light therapy.

The illumination subsystem 204 includes an artificial illumination subsystem 204a and a natural illumination subsystem 204b, which are operated in tandem to provide desired illumination in the habitable environment 100 (FIG. 1). In particular, the illumination subsystem 204 provides lighting in the habitable environment 100 (FIG. 1) with gradually adjusted color temperature and intensity to, for example, improve circadian rhythm. As discussed below, the illumination subsystem 204 may implement a dawn simulator to gradually increase light and sound levels, which are designed to awaken the body when it enters a light stage of sleep. Such may replace standard alarm clocks producing a more natural environment from which to slowly wake. Such may be realized by slow opening blackout shades or slowly allowing more light to pass through an electrochromatic pane over a wakeup period. Active sound may also be slowly increased in volume. Sounds may be those found in the natural environment or may be other sounds, such as music. Such may be realized in an integral unit, or via a dedicated bedside unit, which may provide for sounds as well as artificial lighting.

Also as discussed below, the illumination subsystem 204 may implement nightlights, employing dim (e.g., low-wattage) long wavelength LED or incandescent luminaires that engage in response to motion or ambient light levels, and are designed to sufficiently illuminate rooms for safe navigation without disturbing melatonin levels.

The artificial illumination subsystem 204a includes a plurality of illumination sources 252, and optionally one or more power supplies 254. As previously noted, the illumination sources 252 may take a wide variety of forms, for instance, incandescent, fluorescent, compact fluorescent, or LED lights. LED lighting may be preferable since such is extremely energy efficient and may have a long operating life. The illumination sources 252, either alone or in combination, should be capable of selectively providing a broad range of intensities and a broad range of wavelengths. Such allows the illumination sources 252 to be selectively controlled to produce a wide variety of artificial illumination conditions, for instance, conditions that mimic natural light, diurnal light patterns, circadian light patterns, light therapy patterns, and/or light patterns to accommodate for changes in location (e.g., latitude and/or longitude) or changes in season (e.g., spring, summer, autumn, winter). A circadian light pattern may be a pattern of light during a defined period of time (e.g., solar day, approximately 24 hours) which mimics the intensity and/or color of naturally occurring light (e.g., sunlight and darkness) for a given location (e.g., latitude and/or longitude) and/or at a given time of year (e.g., season, month). A produced, generated or provided circadian light pattern may be produced by a combination of artificial and naturally occurring light, which may be controlled to produce a defined or desired circadian light pattern. The defined or desired circadian light pattern may itself be different from a naturally occurring circadian light pattern at a particular location and/or time of year, or may simply be shifted relative to the naturally occurring circadian light pattern at a particular location and/or time of year. The illumination sources 252 may take the form of arrays of LEDs, each LED capable of producing one or more ranges of wavelengths. Wavelength of emitted light may be adjusted by varying a drive current supplied to the LEDs. Thus, desired wavelengths may be achieved by selectively operating certain sets of LEDs (e.g., LEDs that emit in a given range of wavelengths), and/or by varying a current level supplied to any given LEDs. Intensity may be adjusted by selectively operating more or less LEDs, or by controlling power supplied to one or more LEDs via the power supply or supplies 254. For example, a duty cycle of a pulse width modulated (PWM) drive signal may be varied to adjust intensity of the output.

The power supply or supplies 254 may take a wide variety of forms, mostly dependent on the source of power (e.g., AC line current, DC line current), and the illumination sources (e.g., LEDs). The power supply or supplies 254 may include a transformer to electrically isolate the rest of the circuit from the source of power, and/or step down or step up a voltage. The power supply or supplies 254 may include a switch mode converter, operable to step down and/or step up a voltage. The power supply or supplies 254 may include one or more rectifiers (e.g., passive diode bridge, active transistor bridge of MOSFETs or IGBTs) to rectify AC power to DC power. Less likely, the power supply or supplies 254 may include one or more inverters, to invert DC power to AC power. The power supply or supplies 254 may include one or more dedicated power supply controllers, for instance, a microcontroller such as a microprocessor, DSP, ASIC, PGA, or PLC and/or associated nontransitory computer- or processor-readable media. The power supply or supplies 254 is or are communicatively coupled to control a supply of electrical power to the illumination sources.

The natural light subsystem 204b may include one or more actuators, which are drivingly coupled to control an amount of natural light received in the habitable environment 100 (FIG. 1) via one or more windows 110. As previously discussed, the actuators may, for example, take the form of an electrical power source 256 coupled to control a transmissivity of one or more electrochromatic panes or panels 146 (FIG. 1). As also previously discussed, the actuators may, for example, take the form of an electric motor 258, solenoid or other element drivingly coupled that controls a position of one or more window coverings 150 (FIG. 1) relative to the window, and thereby adjusting an amount of illumination that passes. The window coverings 150 may take the form of "blackout shades," that are automatically operated to shield an occupant or resident of the habitable environment 100 (FIG. 1) from outdoor light. The actuators 256, 258 may receive electrical power from a voltage source, or may receive control signals from a microcontroller. Electrochromatic panes or panels 146 (FIG. 1) may be capable of adjusting (i.e., selectively substantially passing, selectively substantially blocking) ranges of wavelengths passed or blocked, as well as intensity of natural illumination passed or blocked. Thus, electrochromatic panes or panels 146 (FIG. 1) may be preferred over the window covering approach.

Controlling ingress of ambient light (e.g., sunlight, light from street lamps, buildings or signage, security lighting) from an exterior environment aids in management of exposure to levels of light in order to help maintain healthy circadian rhythms. This is particularly important during early summer mornings and long summer evenings, particularly at high latitudes (e.g., above or greater than approximately 40 degrees North or South) and/or urban environments.

The illumination subsystem 204 may also receive illumination information from one or more ambient light sensors or other data sources. For example, one or more ambient light sensors may be positioned within a habitable space to detect ambient light therein. Additionally or alternatively, one or more ambient light sensors may be positioned outdoors to detect ambient light so that the illumination subsystem 204 receives information relating to sunlight proximate the habitable space. In some implementations, the illumination subsystem 204 may receive ambient light information from one or more data sources, such as a table of sunset and sunrise times or status information for one or more light sources or actuators, etc.

In some implementations, the illumination subsystem 204 may include an optical detector that detects information indicative of one or more of wavelength, position, or intensity of optical energy. For example, a photonic crystal array operatively coupled to one or more optical detectors (e.g., CCD detector, CMOS detector) may be used to separately detect one or more ranges of wavelengths of optical energy.

The illumination subsystem 204 may control the ingress of ambient light and/or control artificial illumination in the habitable space environment 100 using the received ambient light information (e.g., from one or more photosensors, from one or more databases). For example, the illumination subsystem 204 may sense the ambient light and control the ingress of ambient light to maintain a constant ambient light level throughout a time period. As another example, the illumination subsystem 204 may detect the presence or absence of a particular range of wavelengths of light, and may adjust the natural or artificial illumination of the habitable space environment based on the detected presence or absence of the range of wavelengths of light.

Municipal water systems use many methods to control the purity of water. Although these methods generally succeed in bringing contaminant levels within national and state limits, water quality occasionally becomes an issue. For example, the Las Vegas sodium and sulfate levels in water would fail New York City standards. In New York, byproducts formed by chlorination are near the federal limit. In response to these concerns, habitable environments 100 may use supplemental treatment technologies to bring contaminant concentrations to well within the safety limits set by American regulatory agencies, as well as international safety standards.

New York City water is currently unfiltered, but a filtration plant is under construction for water drawn from the Croton Reservoir. Additionally, a UV sanitization facility is under construction for germicidal irradiation for the remaining water sources (Catskill/Delaware system).

Sediments-solids of sulfates and chlorides can be suspended in water and produce a cloudy opacity, or turbidity. Water with high turbidity is not inherently unhealthy but elevated levels may be indicative of problems in the filtration process, which may imply that other contaminants have not been adequately removed. Coarse filters 259 reduce suspended solids in water. This is often the first stage of treatment, which optimizes performance of subsequent filters in the system.

Municipal water systems often add chlorine-based disinfectants to the water supply to remove bacteria. This affects water odor and taste, and causes potential irritation of the eyes. The human body contains beneficial symbiotic bacteria, which are necessary for the proper function of the skin and digestive tract. These microbes on the skin are harmed by chlorine. When chlorinated water comes into extended contact with organic matter, byproducts such as tri-halomethanes and halo-acetic acids can form, which are carcinogenic.

Pharmaceuticals and Personal Care Products (PPCPs) comprise a myriad of different chemicals used as active ingredients in medications, cleaning products, and health supplies. PPCPs enter the water system through multiple pathways, such as incomplete metabolism of drugs in the body, improper disposal of pills or personal care and cleaning products. Potentially unsafe levels of PPCPs have accumulated in lakes and rivers, where they can enter municipal water systems. PPCPs are the likely cause of hermaphroditism in fish and lake amphibians, as well as other reproductive harm. Further contamination of water supplies is expected and increases in the quantity of PPCPs in the water are the subject of numerous research programs. The water treatment subsystem 206 may include activated carbon water filters 260 that reduce disinfectant byproducts, pesticides, dissolved gases, chlorine, chloramine, and some pharmaceutical and personal care products, resulting in cleaner and better-tasting water. "Activated" carbon filters contain a maze of passageways and openings, giving activated carbon some 1000 square meters of surface per gram.

Numerous forms of micro-organisms may be damaging to health or an indicator of poor water quality.

For example, coliforms are common, rod-shaped bacteria that are harmless in and of themselves. Like turbidity and suspended solids, coliforms act as indicators: their presence suggests that other, more dangerous microorganisms could survive water treatment and may be present in the supply. The EPA goal for coliforms is zero trace, but the enforceable limit allows 5% of all samples within a single month to test positive. New York City tested positive for 46 of 9958 samples taken in 2010 (or 1.3% of samples in the highest month).

Also, for example, *Escherichia coli* (*E. coli*) bacteria are also rod-shaped bacteria, and the majority of strains are harmless. Some strains, such as O157:H7, cause food poisoning by excreting toxic chemicals that can be life threatening for vulnerable individuals. *E. coli* is transmitted as a result of eating unwashed or undercooked food. Infectious *E. coli* can also be found in water contaminated with fecal matter, such as agricultural runoff.

As further examples, *Cryptosporidium* and *Giardia* are single-celled microbes often found in water systems contaminated by sewage. Much larger than bacteria, these protozoa cause digestive problems, especially in vulnerable populations.

The water treatment subsystem 206 ensures that a supply of clean, healthy water is supplied to the habitable environment 100 (FIG. 1), for example, via taps such as the faucets 130, 136 (FIG. 1) or showerhead 132 (FIG. 1). The water treatment subsystem 206 may use a multi-step approach.

The water treatment subsystem 206 may include one or more mechanical filters 259. The mechanical filters 259 may include one or more sediment or coarse filters to filter sediment or larger particulate matter from the water. The mechanical filters 259 may include one or more fine filters to filter fine particulate from the water. Various types of coarse filter and/or fine filter media may be employed, including wire mesh screens, diatomaceous earth, or ceramic water filter elements.

The water treatment subsystem 206 may include one or more activated charcoal filters 260. The activated charcoal filters may remove particulate in the size range of approximately 0.5 micrometers to 50.0 micrometers.

As an alternative to adding chemical disinfectants, water can be disinfected by irradiation with UV light. The high-energy UV light damages the DNA of microorganisms, making it less possible for them to reproduce. UV treatment is highly effective in clear, sediment-free water. Thus, the water treatment subsystem 206 may employ Ultra-Violet Germicidal Irradiation (UVGI), in an attempt to eliminate microorganisms without using chemical-based filtering. In particular, the water treatment subsystem 206 may include one or more ultraviolet (UV) illumination sources 261 operable to expose the water to UV illumination of sufficient intensity and for sufficient time as to render pathogens in the water non-harmful. The UV illumination sources 261 may be supplied electrical power from one or more dedicated electrical power supplies 262.

As an alternative, a reverse osmosis system (not shown) preceded by a carbon filter may replace the sediment filter and ultraviolet irradiation for the removal of chlorine, PPCPS, disinfectant byproducts, heavy metals, microbes and water hardeners.

The water treatment subsystem 206 may include one or more reservoirs of vitamin C 263 and one or more ports, valves, or manifolds 264 operable to release vitamin C into the water. The ports, valves, or manifolds 264 may be fluidly coupled to release vitamin C only in certain plumbing runs, for example, supplying vitamin C only to water going to the showerhead 132 (FIG. 1) or optionally the faucet 130 associated with the tub or shower stall 122 (FIG. 1). An infusion of vitamin C into shower water may remove residual chlorine. In high concentrations, the skin can absorb vitamin C, for example, when applied as a topical cream. While these levels are significantly higher than those present in the showers, the shower water still provides the skin with small amounts of nutrients.

The air treatment subsystem 208 may include a variety of components to ensure that air supplied to the habitable environment 100 (FIG. 1) is healthy and comfortable for the occupant(s).

Good air quality is one of the most important features of a healthy environment. Stationary adults typically inhale 6 to 10 liters of air each minute. This amount doubles with moderate activity and doubles again with rigorous exercise. Approximately 15 cubic meters of air pass through the lungs of a moderately active adult each day.

Minute quantities of gaseous pollutants and particulates are present in the air from both natural and anthropogenic sources, which can cause serious health problems. Reducing the sources of gases and particulates in the home will decrease their negative effects. Airborne contaminants generated by materials, and the presence of individuals in the home, require expulsion through ventilation to the outdoors, and filtration to ensure that they do not return to the indoor air supply.

The major health effects of poor air quality are lung cancer and cardio-pulmonary disease. A significantly greater number of deaths from these ailments are attributable to periods of higher levels of particulate matter. Other effects of air quality are asthma attacks, emphysema, and interference with the immune system.

At the microscopic scale, natural laws concerning fluid dynamics and gravity work differently, allowing solids and liquids to float in the air almost indefinitely. Put broadly, this microscopic particulate matter is divided into two categories: fine particles, smaller than 2.5 μm ($PM_{2.5}$); and coarse particles larger than 2.5 μm and smaller than 10 μm ($PM_{10-2.5}$). Fine particles are inhalable particles that can lead to a number of health issues. Due to physical processes that govern their formation, fine particles are inherently more acidic and mutagenic than their larger counterparts. Fine particles are drawn deep into the lungs, maximizing damage. Most cases of mortality from inhalation of coarse particulate matter and larger contaminants arise from the toxic chemicals they contain rather than the particles themselves.

Coarse particles do not penetrate as deeply into the lungs as fine particles, and therefore are the less dangerous of the two. However, many coarse particles are allergens. For example, dust mites are microscopic arachnids that feed on pet dander, dead human skin cells, and other biological matter. They thrive in carpets, mattresses, and curtains, and tend to dwell in synthetic fibers rather than natural materials. Mites are not inherently dangerous, but their droppings contain chemicals that trigger an immune response in some individuals. The resulting symptoms often include itchy eyes, runny nose, and wheezing, a reaction that can be particularly debilitating for asthmatics. Nearly one quarter of American homes have dust mite levels associated with symptomatic asthma, and almost half contain enough dust mites to cause allergic reactions in susceptible individuals.

The air treatment subsystem 208 may include one or more mechanical air filters (e.g., mesh, screen, woven, or piled material) 265, through which air passes to remove larger particulate. Suitable mechanical air filters may include an activated carbon air filter, high efficiency particulate (HEPA) air filter (i.e., MERV equivalent 17+), MERV 13-16 air filter, a quantity of Zeolite, or a porous material.

The air treatment subsystem 208 may include one or more electrostatic filters or precipitators 266 to remove fine particulate. In particular, electrostatic filter(s) 266 trap particles that could contain allergens, toxins and pathogens. In addition, the electrostatic filter(s) 266 are installed to reduce dust mites, pollen, carpet fibers, mold spores, bacteria, smoke and diesel particulate matter from the air. The electrostatic filter(s) 266 attracts particles using an electrostatic charge and extracts them from the air into a wire mesh.

The electrostatic filters 266 may take a variety of forms, for instance, ones which place a charge on particles and an opposite charge on a screen or other electrode element to attract the charged particles. An example of such is a corona discharge type of electrostatic filter. The electrostatic filter 266 may be supplied charge via an electrical power supply 267.

Various airborne pathogens may present problems, particularly in enclosed spaces or habitable environments. This may be of particular concern with newer construction techniques which are employed to reduce the exchange of air with the exterior environment, for instance, to reduce heat loss and thereby increase thermal efficiency. Although most airborne microbes are pervasive and generally harmless, some can be dangerous pathogens easily spread throughout a home's ventilation system.

Mold spores can induce skin, nose, throat and eye irritation, and trigger asthma attacks. These fungi release volatile organic compounds that produce a characteristic "moldy" odor and have been linked to dizziness and nausea. Humidity control has been proven effective in reducing mold, and insulated windows reduce condensation so as to prevent mold from growing in nearby joints.

Individual microbes are very small and can evade some filters if not attached to other particles. In order to reduce the probability of airborne pathogens from traveling through the enclosed space or habitable environment 100 (FIG. 1), UVGI can be used to provide additional protection. UVGI is based on a specific frequency of UV light that specifically targets the DNA of microbes and viruses passing through the ventilation system.

The air treatment subsystem 208 may include a UV air sanitizer designed to disinfect air via UV light within one or more components (e.g., ducts) of a ventilation system. The aim is to sterilize airborne bacteria, viruses, dust mites, and mold spores that may have escaped filtration.

Thus, the air treatment subsystem 208 may include one or more UV illumination sources 268. The UV illumination source(s) 268 is positioned to illuminate air with UV illumination of a sufficient intensity for a sufficient time as to render pathogens non-harmful.

Various gaseous pollutants may produce harmful effects in humans, particularly where allowed to accumulate in habitable enclosed spaces. Volatile Organic Compounds (VOCs) are carbon-based chemicals that evaporate into gases at room temperature. Many paints, cleaning products, and pest control chemicals emit VOCs, whose presence in buildings is 2 to 5 times as high as outside levels. Some furniture and building materials also slowly release some kinds of VOC, such as formaldehyde. In the short term, exposure can cause dizziness, nausea, headaches, throat irritation and fatigue, while chronic effects include damage to the liver, kidneys and central nervous system.

Nitrogen dioxide is a product of combustion and mainly found near burning sources. Indoor areas that contain gas stoves, fireplaces and cigarette smoke often have a much higher concentration of nitrogen dioxide. Epidemiological studies suggest that excessive nitrogen dioxide inhalation may decrease lung function, particularly in children. In the short term, it can also trigger allergic responses from the immune system, resulting in irritation of the eyes, nose and throat.

Ozone is created by reactions between molecular oxygen, nitrogen oxides, and sunlight. It is the major catalyst in the formation of smog. Ozone impedes cellular respiration, resulting in reduced cell activity. High concentrations of inhaled ozone can result in an itchy throat and chest tightness; chronic exposure scars the lung tissue, which can lead to emphysema. In addition, ozone interferes with the body's immune system, which compounds the danger from air or water-borne pathogens. Under current standards, the E.P.A. expects ozone to cause more than 110,000 lost work days and 1,100,000 lost school days between 2008 and 2020.

The design of the habitable environment 100 (FIG. 1) avoids or at least reduces the use of materials which emit VOCs, for example, omitting or avoiding products or materials containing certain glues or resins (e.g., particle board). In day-to-day use, materials which emit VOCs are also avoided. For instance, the care or maintenance of the habitable environment 100 (FIG. 1) avoids the use of cleaning compounds which are known to result in VOC emission.

Nevertheless, some VOCs and other gaseous pollutants may appear in the habitable environment 100. Thus, the air treatment subsystem 208 may include one or more activated carbon air filters 249 in the flow path to reduce VOC, nitrogen dioxide and ozone that pass through activated carbon media filters designed to intercept gas molecules. Activated carbon air filters 249 are most useful in areas with sources of fumes or odors.

Additionally or alternatively the air treatment subsystem 208 may also include the use of ion generators, which are devices that emit negative, positive and/or bipolar ions through a variety of methods. The purpose of these ions is to permeate the air and neutralize, inactivate and/or agglomerate harmful airborne particles, including ultrafine and fine particles, viruses, mold spores and/or other pathogens. These ion generators may work alone or as part of a synergistic solution in tandem with media filters or other air-purification devices. Since there is evidence that effectiveness of the purifying effects of ions are altered by humidity and temperature, control systems may be designed to optimize those environmental parameters in order to increase the effectiveness of ion generators.

Additionally or alternatively, the electrostatic filter 266 or some other element may optionally include one or more catalysts selected to catalyze certain impurities in the air. For instance, the electrostatic filter 266 may include one or more catalysts (e.g., non-metal catalysts, for instance: titanium dioxide, chromium oxide or aluminum oxide, or metal catalysts, for instance: Fe, Co, Ni, Cu, Ru, Rh, Pd, Ag, Ir, Pt and Au, as well as combinations or alloys thereof, such as an alloy of Pt and Rh) to catalyze species of VOCs into more acceptable or less harmful forms.

The air treatment subsystem 208 may include one or more heaters 269 to heat air. The heaters 269 may take any of a large variety of forms. Heaters 269 may take the form of various electric heaters, which employ a resistive radiant element to heat air. Heaters 269 may take the form of forced air heaters which typically include burners that burn a fuel such as natural gas or propane. Heaters 269 may alternatively take the form of oil furnaces, or the like.

The air treatment subsystem 208 may include one or more compressors 270 which may form part of an air conditioner cooling unit. The compressors 270 may be fluidly coupled to control pressure of a fluid, coupled with one or more coils or other heat exchangers, and may operate in a similar fashion to standard air conditioner units to remove heat from the air.

Relative humidity is the measure of water vapor in the air compared to the total amount that can be held at a given temperature. In the spring and summer months, humidity levels can be high enough to cause discomfort. When cool air flows through central air systems, humidity in the air is reduced, since cooler air holds less water vapor. However, as dry air is drawn in and heated within a building in the winter, relative humidity falls, so the air feels dry.

To maintain comfort, and prevent the establishment and growth of mold, dust mites and bacteria, relative humidity in the habitable environment 100 should be kept between 30% and 50%. Using high-temperature water within the ventilation system of the home suppresses bacteria growth. Humidity towards the bottom of this range is better in terms of air quality, but extremely low moisture levels may lead to dry skin and respiratory irritation.

Thus, the air treatment subsystem 208 may include a humidifier and/or dehumidifier 271 which controls humidity throughout the enclosed habitable environment 100 (FIG. 1). This is particularly important when moisture levels in the air fall in winter, thus the air treatment subsystem 208 must increase the moisture (i.e., humidify) during dry periods. Conversely, the air treatment subsystem 208 lowers moisture (i.e., dehumidifies) during humid periods. The humidifier and/or dehumidifier 271 may include a reservoir (not shown) that retains water to either be added to the air in a humidification mode or removed from the air in a dehumidification mode. The humidifier and/or dehumidifier 271 may include a compressor (not shown) used to, for example, cool air as part of removing moisture. The humidifier and/or dehumidifier 271 may optionally include a heating element to heat air as part of adding moisture.

To control relative humidity, the air treatment subsystem 208 may additionally employ exhaust vents 158*a* (FIG. 1), particularly in the bathroom 100*b* (FIG. 1), used to increase the ventilation rate in that portion of the habitable environment in order to rapidly lower humidity generated therein, for example, from showers 122, 132 (FIG. 1).

The air treatment subsystem 208 may include one or more fans and/or blowers 272 coupled to one or more ducts (FIG. 1) and/or vents (FIG. 1). The fans and/or blowers 272 may circulate air within the air treatment subsystem 208 and/or within the habitable environment 100 (FIG. 1). The fans and/or blowers 272 may expel air to an exterior environment and/or draw fresh air from the exterior environment, prior to treating the fresh air. In particular, a high flow ventilation system expels indoor air to reduce the buildup of internally generated air impurities such as volatile organic compounds, dust mites and pet dander. A heat exchanger may advantageously be employed to recover energy from the outgoing air.

As an alternative for humidity control, a waterfall (not shown) in the enclosed space can both increase and decrease the relative humidity. When chilled water is circulated in the waterfall, the system absorbs water vapor from the air. When room temperature or warm water is circulated in the waterfall, the system releases water vapor into the air. The waterfall may also provide a soothing background sound in the habitable environment 100.

The practice of aromatherapy employs a wide variety of oils and extracts, with differing effects on mood and emotion. Supporters of contemporary aromatherapy practices suggest that various fruit and plant-based aromas have the ability to positively affect mood, behavior and perceptions of wellness. Examples of plant-based scents and their corresponding benefits include:

Lavender effects include restful sleep during exposure at night, increased vigor the morning after night time exposure, enhanced mood, decreased heart rate and increased positive mood. Jasmine effects include relaxation, decreased heart rate and increased positive mood. Orange scent has been used to reduce anxiety and help maintain better mood in stressful circumstances. Rosemary has been shown to enhance memory and increases reaction times.

The scent subsystem 210 is operable to selectively dispense or disperse one or more scents into the air in the habitable environment 100 (FIG. 1) or portion thereof. The scent subsystem 210 may include a number of reservoirs 273 which hold various scents (e.g., lavender, rosemary), typically in a liquid form. One or more vents, valves or manifolds 274 are selectively operable to fluidly communicably couple selected ones of the reservoirs to emit or disperse scent into the habitable environment 100 (FIG. 1) or portion thereof, for example, via ducts or vents of the air treatment subsystem 208. The scent subsystem 210 may optionally include one or more fans and/or blowers 275 to assist in dispersing the scent(s) into the habitable environment 100 (FIG. 1) or portion thereof. The scent subsystem 210 may optionally include one or more heaters 276, thermally (e.g., conductively, radiantly or convectively) coupled to the reservoirs 273 or an output of the reservoirs 273 to heat and thereby vaporize liquid forms of the scent(s) into a gaseous form more easily dispersible into the habitable environment 100 (FIG. 1) or portion thereof.

Additionally or alternatively, one or more passive components may be employed to diffuse scents into the habitable environment 100. For example, various items or objects may be impregnated with specific scents. Such items or objects may include various fabrics, such as curtains, linens or bedding (e.g., pillow cases, pillows, sheets, blankets, comforters, duvets), carpets, towels, etc. Such items may include a pouch, sack or other breathable encasement or enclosure, which may be positioned at various locations about the habitable environment 100, for instance, in a flow path of a vent or within a pillow case. The pouch or sack may be distributed in an air-tight packet, container or envelope which is opened immediately prior to use. Such may advantageously maintain the scent emitting materials fresh between manufacture and use, and may prevent undesired scents from being emitted into the habitable environment. Thus, certain packets may be opened to customize the scent to a specific occupant or occupants of the habitable environment 100, and the scent(s) allowed to disperse through the habitable environment 100.

Thus, active or passive components of a scent subsystem 210 deliver room-specific aromatherapy based on the room's function and aroma benefit. A wide variety of essential oils and crafted aromas are available for use in the dispenser with the option to tailor to individual specifications.

The sound subsystem 212 provides sound into the habitable environment 100 (FIG. 1) or portion thereof. In particular, the sound system may, for example, provide soothing sounds (e.g., running water, forest sounds, waves, "white" noise, "pink" noise, music). The sound subsystem 212 may include one or more speakers 277, which may be positioned throughout the habitable environment 100 (FIG. 1) or portion thereof. Sounds may be selected to produce relaxation or to allow an occupant to focus more intently than the occupant would focus without the sounds, for example, while reading or working. The sound subsystem 212 may include one or more amplifiers 278 electrically, optically or wirelessly coupled to provide signals to the speakers 277 (e.g., typically analog or digital electrical signals) that cause the speakers 277 to reproduce the sounds represented by the signals. The sound subsystem 212 may optionally include a nontransitory computer- or processor-readable storage media 279 that stores digital versions of the sounds, for example, in a library. The amplifier 278 may include one or more CODECs and/or microcontrollers to convert the digital versions of the sounds into signals for controlling the speakers 277. The sound subsystem 212 may include one or more microphones (not shown) to detect noise in the habitable space. The sound subsystem 212 may provide masking sound to offset or cancel the noise.

The input/output (I/O) subsystem 214 is communicatively coupled to the control subsystem 202 to supply input thereto and/or to provide output therefrom. The input/output (I/O) subsystem 214 may include various sensors 280-282, user operable input/output (I/O) devices, controls, panels or kiosks 283, 284, and other devices or components such as televisions 285.

For example, one or more occupant sensors or detectors 280 may be positioned in, or proximate to, the habitable environment 100 (FIG. 1) or portions thereof. The occupant sensor(s) or detector(s) 280 sense or detect a presence, or conversely an absence, of an occupant in the habitable environment 100 (FIG. 1). The occupant sensors or detectors 280 may take any of a large variety of forms. For example, the occupant sensor(s) or detector(s) 280 may take the form of various motion detectors, for instance, passive infrared based motion detectors, proximity (RF) based motion detectors, microwave or radar based motion detectors, ultrasonic based motion detectors, vibration based motion detectors and/or video based motion detectors. The occupant sensor(s) or detector(s) 280 may include simple contact switches which detect movement or operation of a fixture or some other element (e.g., turning on a radio, television, stereo, appliance) by an occupant. The occupant sensor(s) or detector(s) 280 may take the form of simple cameras (e.g., digital cameras) which may capture images, from which changes from frame to frame may indicate a presence or absence of an occupant. The occupant sensor(s) or detector(s) 280 may detect a presence or absence of an object associated with the occupant, for instance, a smartcard or keycard, or a handheld or mobile device.

Also, for example, one or more temperature sensors or detectors 281 may be positioned in, or proximate the habitable environment 100 (FIG. 1) or portions thereof. The temperature sensor(s) or detector(s) 281 sense or detect a temperature proximate the temperature sensor or detector and provides signals to the control subsystem 202 and/or air treatment subsystem 208 indicative of the sensed or detected temperature. The temperature sensor(s) or detector(s) 281 may employ various components, for example, thermocouples or thermally responsive resistors.

Also, for example, one or more humidity sensors or detectors 282 may be positioned in, or proximate the habitable environment 100 (FIG. 1) or portions thereof. The humidity sensor(s) or detector(s) 282 sense or detect humidity or relative humidity proximate the humidity sensor or detector 282 and provides signals to the control subsystem 202 and/or air treatment subsystem 208 indicative of the sensed or detected humidity. The humidity sensor(s) or detector(s) 282 may employ various components.

One or more in-room user operable input/output (I/O) controls, panels or kiosks 283 may allow an occupant or facility personnel (e.g., cleaner, maintenance) to interact with the environmental control system 200. The in-room I/O control(s), panel(s) or kiosk(s) 283 may include a touch-sensitive or touch-responsive display, which allows presentation of information and a graphical user interface (GUI). The information may include information about the current settings of the environmental control system 200 and different settings which may be selected by the user. The GUI may include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs to select from. The programs may be presented in a simple fashion with simple labels or names, yet may have fairly complicated sets of settings for various combinations of the subsystems 202-214.

The in-room user operable I/O control(s), panel(s) or kiosk(s) 283 may also allow collection of information from an occupant which is indicative of the occupant's impressions and overall satisfaction with the habitable environment 100, and particularly the health and wellness amenities. Such may be captured with an automated survey, which includes various questions and possible ratings, presented, for instance, via a graphical user interface (GUI).

One or more facility user operable I/O controls, panels or kiosks 284 may allow facility personnel (e.g., clerk, concierge, cleaner, maintenance personnel) to interact with the environmental control system 200. The facility I/O control(s), panel(s) or kiosk(s) 284 may include a touch-sensitive or touch-responsive display, which allows presentation of information and a GUI. The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound or other aspects of the environment. The GUI may present the user with a set of defined programs to select from. The programs may be presented in a simple fashion with simple labels or names, yet may have fairly complicated sets of settings for various combinations of the subsystems 202-214. The GUI may optionally allow facility personnel to define new programs, delete old programs, and/or modify existing programs.

The GUI may, for example, allow facility personnel to enter information about a specific guest or other occupant that will occupy a respective habitable environment. Information may, for example, include a location from which the occupant originated. The location may be specified in a variety of forms including name (e.g., city, state, country) and/or geographic coordinates (e.g., latitude and/or longitude). Such may allow the environmental control system 200 to determine a control program that accommodates for changes experienced by the occupant due to travel to a new location. Thus, the environmental control system 200 may adjust for changes in the diurnal cycle and/or circadian cycle. Information may include an age or approximate age of the occupant, which may affect or be related to circadian cycle and the ability to adjust for travel (e.g., "jet lag"). Such may allow accommodation or treatment for other issues, for instance, seasonal affective disorder or providing light therapy to treat certain ailments or symptoms.

As noted previously, one or more televisions 285 may be used to at least present information to an occupant. In some implementations, a control, such as a remote control, maybe used by the occupant to interact with the television 285 to make selection of various user-selectable options for controlling one or more components of the environmental control system 200. As also previously noted, an occupant may use a handheld or mobile device 182c (FIG. 1), such as a smart phone, tablet computer, etc., to interact with environmental control system 200.

The server 244 and nontransitory computer- or processor-readable medium 246 may store and provide information to other components of the environmental control system 200. Such may, for instance, include a schedule that specifies which occupants will occupy which habitable environments 100 (FIG. 1) of the facility, and at what times. This information may also specify, or be mapped to, information which specifies desired environmental characteristics for the respective occupants. Thus, the environmental control system 200 may automatically adjust environmental characteristics in a variety of habitable environments 100, customized for the particular occupant.

A sanitizing subsystem 216 may be an integral part of the habitable environment 100, or may be selectively provided thereto or therein, for example, when preparing for another occupant or guest. For instance, the sanitizing subsystem 216 may be provided as a cart 293 with wheels 294, as illustrated in FIG. 2, for selectively being wheeled into the habitable environment 100. While illustrated as a cart, the sanitizing subsystem 216 may be provided as a portable unit which may be hung from a pole mounted approximately centrally in the habitable environment, or less preferably hung from a wall or other structure in the habitable environment 100. Such may advantageously allow the sanitizing subsystem 216 or portion thereof to be positioned at a higher point than might otherwise be achieved via a cart 293.

The sanitizing subsystem 216 may provide a sanitizing agent into the habitable environment 100 to destroy or render non-harmful various pests or pathogens. The sanitizing subsystem 216 may optionally evacuate the sanitizing agent from the habitable environment 100 (FIG. 1), after a sufficient time has passed for the sanitizing agent to destroy or render non-harmful the pests or pathogens.

The sanitizing agent may take a variety of forms. The sanitizing agent may be in a gaseous form, or may be a vapor or "dry vapor" (i.e., non-wetting) form. Suitable sanitizing agents may, for example, include forms chlorine dioxide, peracetic acid, hydrogen peroxide and electrochemically activated solutions (e.g., electrolyzed water). Suitable sanitizing agents may, for example, include photocatalytic antimicrobial materials (e.g., composite photocatalyst, nanoparticle sized zinc metal in a matrix of nano-crystalline titanium dioxide ($TiO_2$) available under the trademark OXITITAN™ from EcoActive Surfaces, Inc. of Pompano Beach, Fla.). Such may provide an antimicrobial surface, reduce odor and VOCs, provide for hydrophilic or hydrophobic self-cleaning, and/or UV or corrosion protection. The UV protection may be particularly advantageous where UV illumination is also utilized in sanitizing the habitable environment 100.

The sanitizing agent may be a photocatalytic composition that includes $TiO_2$ nanoparticles doped with at least one doping agent. The addition of the doping agent may increase the absorbance of light across a range of wavelengths of light (e.g., about 200 nm to about 500 nm). In some implementations, the addition of the doping agent increases the absorbance of light across the range of about 350 nm to about 450 nm, for example. The doping agent useful in the photocatalytic composition may be any suitable doping agent including, but not limited to, Ag, Zn, Si, C, N, S, Fe, Mo, Ru, Cu, Os, Re, Rh, Sn, Pt, Li, Na, and K, and combinations thereof. The doping agent may disrupt the crystal lattice structure of the titanium dioxide nanoparticles thereby altering the absorbance spectrum of the composition.

While some of the examples given here are based on $TiO_2$, a variety of other photocatalysts such as $Fe_2O_3$ also may be similarly optimized, for example by inclusion of $SnO_2$ at differing levels.

Alternatively, or additionally, the sanitizing agent may be in the form of electromagnetic energy or radiation, for example, specific ranges of wavelengths such as UV of electromagnetic energy.

The sanitizing subsystem 216 may include one or more reservoirs of sanitizing agent(s) or materials 286 which when combined produce a sanitizing agent. The sanitizing subsystem 216 may include one or more fans or blowers 287 to assist in dispersing the sanitizing agent into the habitable environment 100 (FIG. 1). In some implementations, the fan(s) or blower(s) 287 may also assist in removing or evacuating the sanitizing agent into the habitable environment 100 (FIG. 1). The sanitizing subsystem 216 may optionally include one or more transducers 288 operable to place the sanitizing agent in a form more amenable to dispersion. The transducer(s) 288 may take the form of a heater, for example, to vaporize the sanitizing agent. Additionally or alternatively, the transducer(s) 288 may take the form of one or more a high frequency vibration elements (e.g., piezoelectric element) to pulverize or otherwise particalize either dry sanitizing agent into a very fine particulate form or to break up droplets of liquid sanitizing agent into a very fine form, for instance, that does not wet surfaces. Other types of transducers 288 may be employed.

The sanitizing subsystem 216 may include one or more ports or vents 289 for dispersing the sanitizing agent. Ports or vents 289 may be built into a housing 290 of the sanitizing subsystem 216. Additionally, or alternatively, the sanitizing subsystem 216 may include one or more one or more hoses 291 with nozzles 292 or other openings for dispersing the sanitizing agent.

The sanitizing subsystem 216 may include one or more wands selectively operable to emit electromagnetic energy or radiation, for example, specific ranges of wavelengths such as UV of electromagnetic energy. The wand(s) may include one or more illumination sources, for instance, UV illumination sources and may be electrically coupled to a power source carried by a cart via one or more cables. Alternatively, illumination sources may be located in the cart, and the wand(s) optically coupled thereto via one or more cables.

The sanitizing subsystem 216 may include one or more illumination sources positioned so as to be exposed to the ambient environment in order to provide illumination into the habitable environment 100 directly from a housing of the sanitizing subsystem 216. The illumination sources may be positioned on an exterior of the cart or within the exterior of the cart and optically communicatively coupled to the exterior via one or more optical ports (not shown). This may allow the general habitable environment 100 to be optically treated, for instance, with UV illumination. The wand(s) may, for instance, be used to treat areas or spaces that would not otherwise be treated via direct illumination from the illumination sources, for instance, areas or spaces that are not in a direct line of sight of the illumination sources. In some implementations, the illumination sources may provide the illumination which is optically coupled to the wand(s) via a cable.

Sanitizing may require as little as three hours of exposure to UV illumination, dependent of a variety of factors such as type of pathogens, distance and intensity (e.g., incident energies). Targeted pathogens may take a variety of forms, for example, mold spores, and organisms such as various bacillus, protozoa, virus, yeast. Mold spores may include, for instance: *Aspergillus flavus, Aspergillus glaucus, Aspergillus niger, Mucor racemosus* A, *Mucor racemosus* B, *Oospora lactis, Penicillium expansum, Ppenicillium roqueforti, Penicillium digitatum, Rhizopus nigricans*. Illumination may occur before, after, during or before and after application of a photocatalytic antimicrobial agent or coating. Operation may require that the habitable space be vacant during the entire period of treatment. Thus a remote control (e.g., wireless handheld transmitter and wireless receiver) or a delay start timer may be advantageously employed.

Various nontransitory media discussed above may store information such as data including configuration information in one or more data structures. Data structures may take a variety of forms, for example, records associated with relational databases, a database itself, lookup tables, etc. The data structures may store a variety of different information or data.

Figure 3:
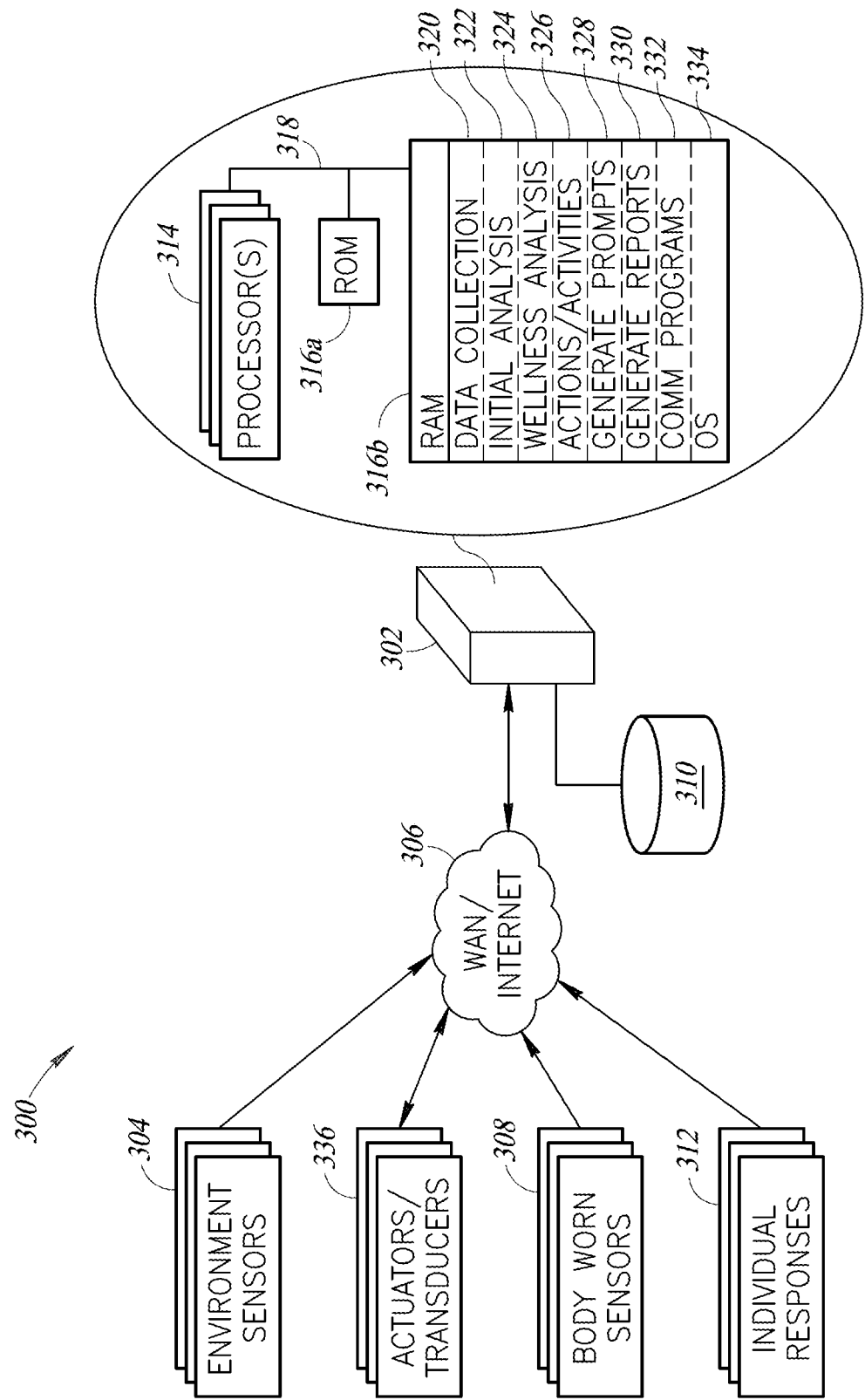
FIG. 3 is a block diagram that shows a portion of a wellness monitoring system, according to one illustrated embodiment.

FIG. 3 shows a block diagram of a wellness monitoring system 300 for monitoring individual and environmental characteristics within one or more habitable space environments 100 (FIG. 1), according to one illustrated embodiment. The components of FIG. 3 may be implemented in conjunction with or in addition to some or all of the components of FIGS. 1 and 2. The habitable space environment may include one or more types of spaces including, but not limited to, offices, homes, hotels, spas, hospitals, shopping centers, fitness centers, or vehicles (e.g., planes, trains, automobiles, ships).

The wellness monitoring system 300 includes a control subsystem 302, which may be operatively coupled to the various components shown in FIG. 2. The control subsystem 302 may take the form of one or more programmed computers or other processor-based systems or devices. For example, the control subsystem 302 may take the form of a conventional mainframe computer, mini-computer, workstation computer, personal computer (desktop or laptop), or handheld computer. The control subsystem 302 may be physically located remote from the other components of the wellness monitoring system 300. For example, the control subsystem 302 may include one or more server computer systems (e.g., server computer systems 244 and associated nontransitory data storage device 246 of FIG. 2). The control subsystem 302 and/or server computer systems 244 and associated nontransitory data storage device 246 may, for example, be controlled and operated by a facility (e.g., hotel, spa, apartment building, condominium building, hospital) in which one or more habitable space environments 100 (FIG. 1) are located, or by another entity.

The control subsystem 302 may include one or more processors or processing units 314, nontransitory processor-readable system memories 316A, 316B (collectively 316) and a system bus 318 that couples various system components including the system memory 316 to the processing unit(s) 314. The processing unit(s) 314 may be any logic processing unit, such as one or more central processing units (CPUs), digital signal processors (DSPs), application-specific integrated circuits (ASICs), field programmable gate arrays (FPGAs), programmable logic controllers (PLCs), artificial neural network circuits or systems or any other logic components. The system bus 318 can employ any known bus structures or architectures, including a memory bus with memory controller, a peripheral bus and a local bus. The system memory 316 includes nontransitory Flash or read-only memory ("ROM") 316A and nontransitory random access memory ("RAM") 316B.

The RAM 316B may store program engines, such as a data collection engine 320, an initial analysis engine 322, a wellness analysis engine 324, an actions/activities engine 326, a generate prompts engine 328, a generate reports engine 330, a communications engine 332, an operating system 334, or other programs or engines and program data. The functionality of the program engines 320-334 is discussed below with reference to FIGS. 4-11. The programs engines may include instructions that cause the processor(s) 314 to automatically receive input and/or display output via various user operable input/output (I/O) devices, controls, panels or kiosks 182 (FIG. 1) or television 184 (FIG. 1).

Figure 4:
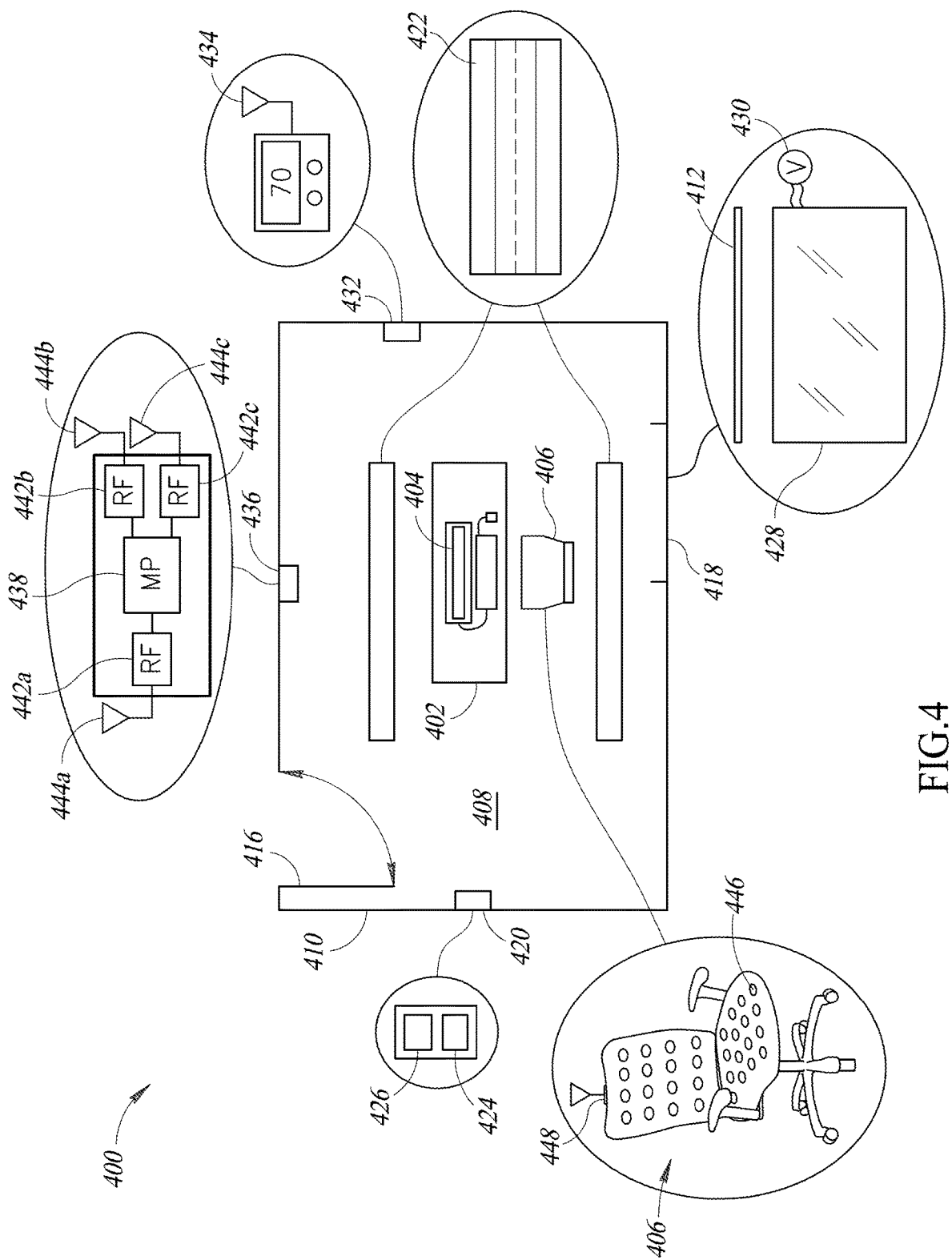
FIG. 4 is a schematic diagram of a habitable environment associated with a wellness monitoring system, according to one illustrated embodiment.
Figure 5:
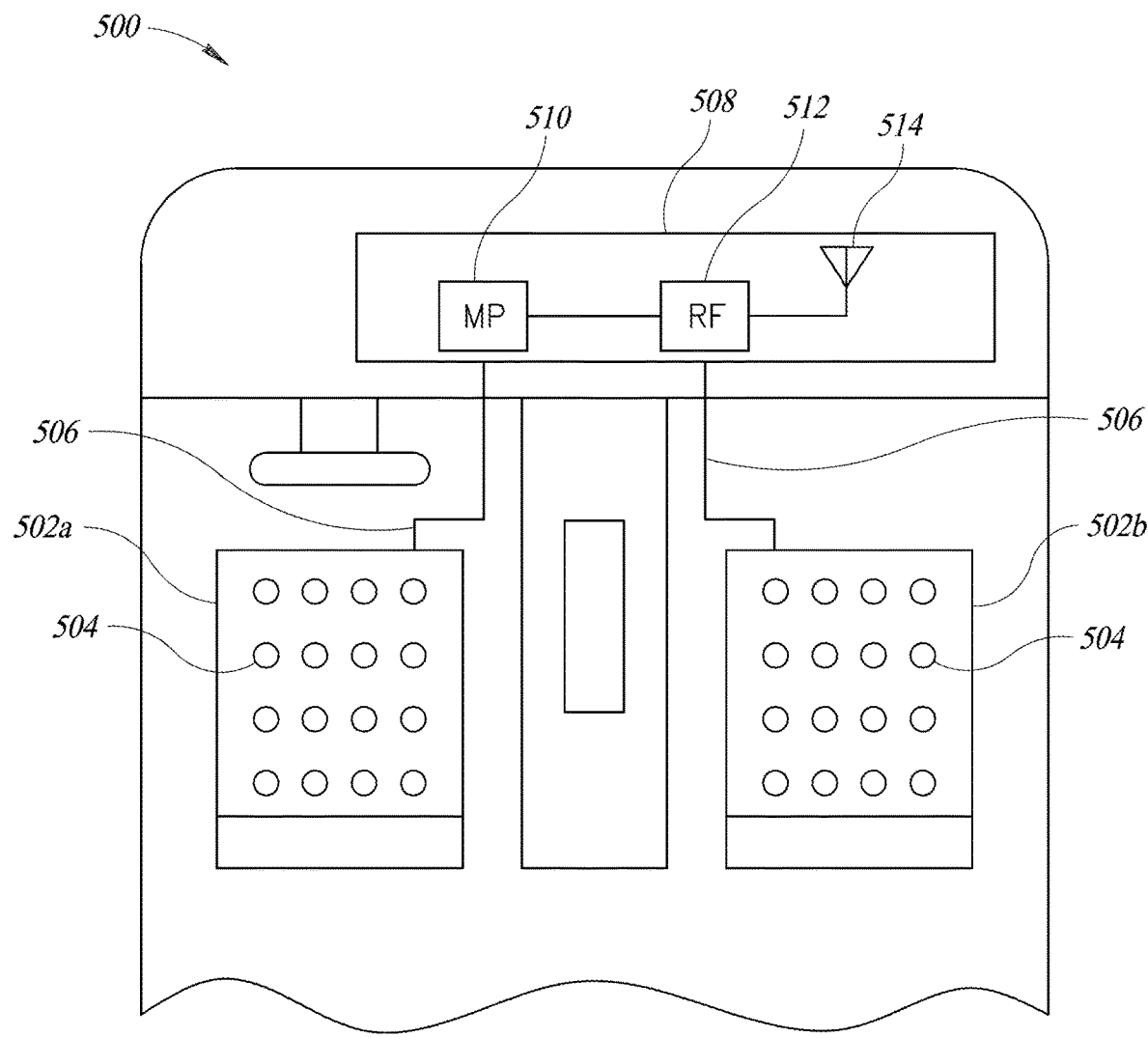
FIG. 5 is a schematic diagram of an automobile associated with a wellness monitoring system, according to one illustrated embodiment.

The control subsystem 302 may also be operatively coupled to one or more environmental sensors or transducers 304 via a communication network 306 (e.g., WAN, Internet). As discussed above, the environmental sensors 304 may include one or more occupant sensors or detectors 280 (FIG. 2), one or more temperature sensors or detectors 281 and one or more humidity sensors or detectors 282. One or more additional environmental sensors 304 may be provided that measure, for example, carbon dioxide, carbon monoxide, airborne particles, VOCs, ozone, nitric oxide, nitrogen dioxide, luminance, spectral distribution, ambient noise, pressure and motion. For example, the control subsystem 302 of the wellness monitoring system 300 may receive information representative of a measure of pressure asserted by at least a portion of the first individual on at least one of a piece of furniture (e.g., chair, bed) or flooring in the environment. FIGS. 4 and 5 illustrate various examples of environmental sensors 304 that may be included as part of the wellness monitoring system 300.

Figure 6:
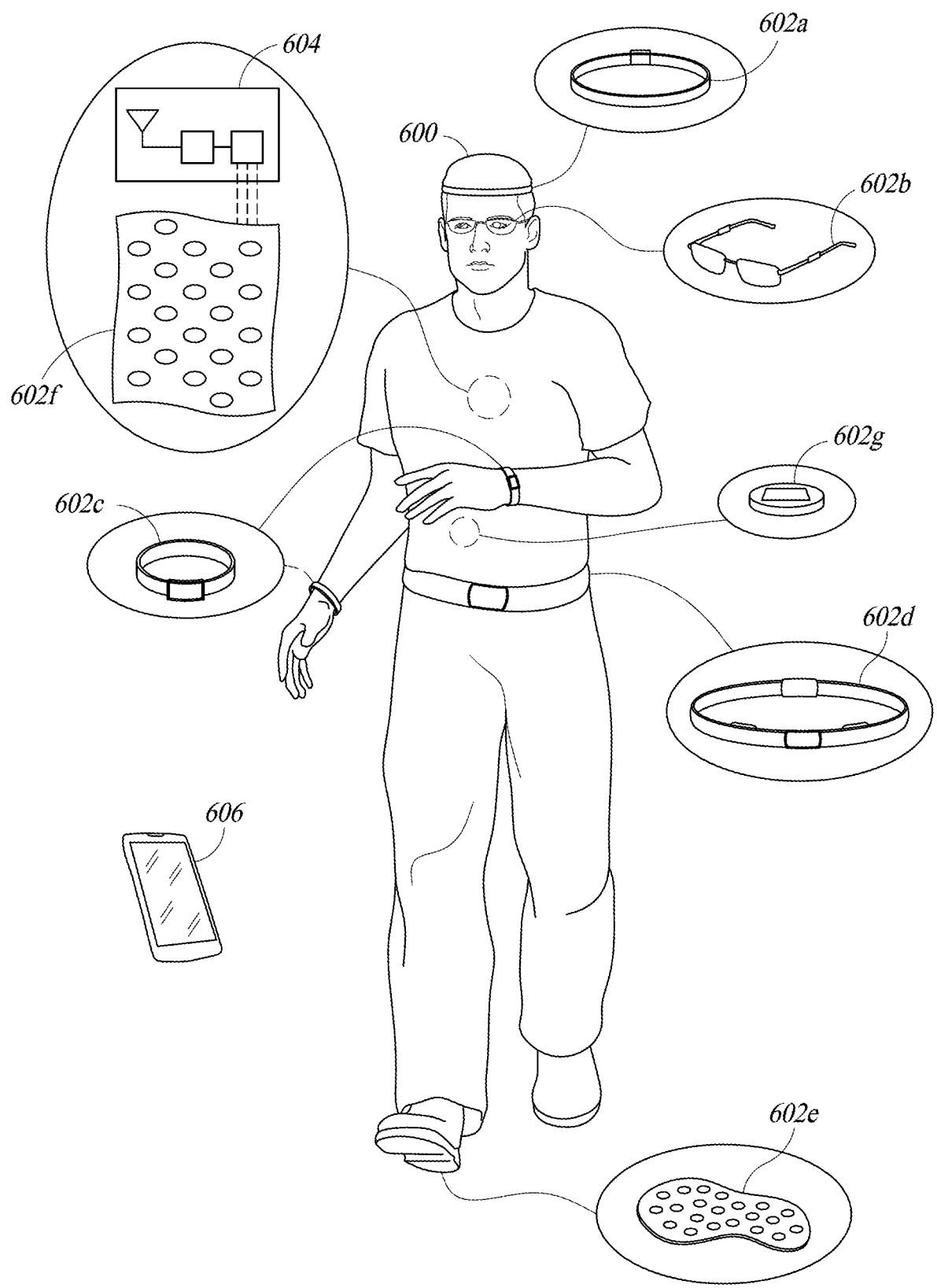
FIG. 6 is a schematic diagram of an individual wearing a plurality of body worn sensors associated with a wellness monitoring system, according to one illustrated embodiment.

The control subsystem 302 may also be operatively coupled to one or more individual sensors or body worn sensors or transducers 308. For example, the control subsystem 302 of the wellness monitoring system 300 may receive from the body worn sensors 308 information representative of at least one of a bodily temperature, heart rate, bodily level of oxygen, amount of perspiration, cardiovascular activity, amount of bodily activity, glucose level, blood pressure, weight, bodily alcohol level, amount of sleep, and/or level of sleep. The information may be received from the body worn sensors 308, for example, via one or more communications channels, for instance, one or more wired or wireless networks, Bluetooth® channels, USB® channels, infrared channels, etc. The body worn sensors or transducers 308 may take a variety of forms, wearable by the individual. For example, sensors may be ingested, integrated into armbands, smart watches, clothing, adhesive patches (e.g., EKG electrodes), headwear including hats or eyewear, shoes or orthotics for shoes. FIG. 6 illustrates various examples of body worn sensors 308 that may be included as part of the wellness monitoring system 300.

The control subsystem 302 may be coupled to one or more actuators/transducers 336 positioned within one or more of the habitable environments. For example, the control subsystem 302 may be operative coupled to the illumination subsystem 204 (FIG. 2), water treatment subsystem 206, air treatment subsystem 208, scent subsystem 210, sound subsystem 212, input/output (I/O) subsystem 214, sanitizing subsystem 216, temperature subsystem, or other controllable environmental subsystems.

The control subsystem 302 of the wellness monitoring system 300 may also receive data from a knowledge/studies data source 310 ("knowledge data source"). This data may relate to medical information including wellness parameters, health records, environmental records, building topology, cost/benefit analysis data, feasibility studies, recently published research, occupant socioeconomics, gender, age, health status, and the like. For example, the knowledge data source 310 may include results from sleep studies, wellness studies, environmental studies, light studies, or other types of available studies or knowledge. Some of the knowledge data may be reducible by building topology. As an example, hospitals, schools, and nursing homes have known demographic profiles. Health outcomes may detect objective or perceived changes in the health and wellness of occupants as measured by a survey, assessments, clinical outcomes, opinions of healthcare providers, or biometric measurements that may be stored in the survey data source 310.

The control subsystem 302 also receives information in the form of responses 312 from an individual to a number of queries proposed to the individual. Such may, for example, be entered via a user interface, for instance a keyboard, keypad, virtual keyboard, virtual keypad, touch interface, or microphone. Responses 312 may be in response to specific queries, for instance queries presented either individually or as part of a questionnaire. Queries may take a large variety of forms. Queries may be closed questions requiring yes/no responses or a selection from a list of proposed choices for response. Queries may be opened questions, allowing essentially free-form answers. Queries may solicit self-assessed values for various wellness related parameters, some or all of which may be difficult to objectively measure via sensors or transducers. For example, queries may be related to eating habits, drinking habits, sleeping habits, physical or mental wellness or well-being, schedules, levels of stress, and/or social interactions. Reported parameters may, for example, include: number of years smoking or since quitting smoking, number of alcoholic drinks per week and/or type of alcoholic drinks, level and type of drug use, whether such use is legal or illegal, family health history, own health history, or nutrition and dietary habits.

FIG. 4 shows a habitable space environment 400 that includes a plurality of environmental sensors which may be components of a wellness monitoring system, such as the wellness monitoring system 300 of FIG. 3. In the illustrated embodiment, the habitable space environment 400 takes the form of an office that includes a desk 402, a computer 404 and a chair 406. It should be appreciated that the habitable space environment 400 may be other types of indoor and/or outdoor environments.

The habitable space environment 400 includes a floor system 408, wall system 410, and ceiling system 412, and may include one or more doors 416 and/or windows 418. The door 416 may provide ingress and egress to an exterior environment, or may provide ingress and egress to other enclosed spaces within the habitable environment 400. For instance, the door 416 may provide passage between the habitable environment 400 and a hallway (not called out) outside of the habitable environment 400. Another door (not shown) may provide passage between one portion and another portion of the habitable environment 400.

The wall system 410 of the habitable space environment 400 includes an occupancy sensing wall switch 420 that is operatively coupled to overhead lights 422. The occupancy sensing wall switch 420 includes a sensor portion 424 and a switch portion 426. The sensor portion 424 may use passive infrared, ultrasonic and/or other sensing technology to detect an individual's presence in or absence from the habitable space environment 400. The wall switch 420 may be operatively coupled to the overhead lights 422 via a wired or wireless connection. In some implementations, the sensor portion 424 of the occupancy sensing wall switch 420 is mounted on the ceiling system 412 or floor system 408, rather than the wall system 410. The occupancy sensing wall switch 420 automatically turns on the lights 422 when motion is detected and automatically turns off the lights when motion is no longer detected. The switch portion 426 may be used to manually turn on or turn off the lights 422.

The habitable space environment 400 may also include one or more windows 418 from an exterior thereof, for example from a natural source of light (e.g., the Sun). These may include "smart" panes or electrochromatic panes 428 in the window 418 and associated actuator, for instance a voltage source 430 coupled to control a transmissivity of the electrochromatic panes. Electrochromatic panes 428 may commonly be referred to as electrochromatic glass, but the embodiments herein are not intended to be limited to glass. These may include one or more drapes, shades or curtains or other window coverings and an actuator such as an electric motor coupled by a transmission to drive the window covering along a track relative to the window(s) 418. Electrochromatic panes 428 may include glass, mirror or other material which is controllably or selectively transmissive of a light, some wavelengths in response to a stimulus, for instance in response to an applied signal such as an applied voltage and/or applied current. For example, electrochromatic panes 428 may be generally or substantially transparent to various wavelengths (e.g., white light) in response to a first signal, and generally or substantially opaque to various wavelengths (e.g., white light) in response to a second signal, different from the first signal. The electrochromatic panes 428 may be adjustable to control the intensity of light which is substantially passed or substantially blocked, and/or control wavelengths which are selectively substantially passed or substantially blocked. The panes 428 may utilize any suitable technology including, but not limited to, electrochromatic, photochromic, thermochromic, suspended particle, micro-blind or liquid crystal devices.

The habitable space environment 400 may also include a thermostat 432. The thermostat 432 may be sensor-driven and programmable, and may be coupled to the control subsystem 302 (FIG. 3) via a wireless transceiver 434 or a wired interface. The thermostat 432 may send sensor data (e.g., temperature, humidity, barometric pressure) to the control subsystem 302 directly or through one or more intermediate communication devices, such as a wall panel, kiosk, handheld computer, etc. The thermostat 432 may receive control data (e.g., temperature settings, humidity settings) from the control subsystem 302 or other communication devices.

The habitable space environment 400 may also include a panel 436 that facilitates communication between the sensors within the habitable space and the remotely positioned control subsystem 302. The panel 436 may include one or more processors 438 operatively coupled to a plurality of wireless transceivers 442A, 442B, 442C (collectively 442). Each of the wireless transceivers 442A, 442B, 442C is coupled to a respective antenna 444A, 444B, 444C to provide wireless communication between the panel 436 and remotely located devices, such as the control subsystem 302. The panel 436 may provide communication via one or more communications channels, for instance one or more wired or wireless networks, Bluetooth® channels, USB® channels, infrared channels, etc. The panel 436 may also include an I/O interface, such as a touchscreen, which allows an individual the ability to receive prompts from the control subsystem 302 and to input responses to the prompts.

The habitable space environment 400 also includes the chair 406, which includes a plurality of sensors 446 dispersed on a seat portion and a back portion of the chair. A wireless transceiver and antenna 448 may be operatively coupled to the sensors 446 to transmit sensor data to the panel 436 or to other computing devices (e.g., the control subsystem 302, smartphone). The sensors 446 may be operative to measure one or more of pressure, temperature or motion of an individual seated in the chair 406.

One or more queries associated with the chair 406 may also be provided to a user through a suitable interface, such as one or more user operable I/O devices, controls, panels or kiosks, or control subsystems.

The chair may also include one or more controllable actuators that adjust a physical characteristic of the chair. For example, the chair 406 may include one or more controllably inflatable members that may be used to selectively adjust a lumbar support of the chair 406, a height of the chair, a firmness of the seat of the chair, etc. The control subsystem may selectively adjust one or more of the controllable actuators based on information received from the sensors 446 or from other data sources (e.g., survey results) that may be relevant to user's physical wellness.

The sensors 446 may also be used to provide feedback to the user regarding one or more sitting habits, such as the user's posture, the duration the user sits in the chair 406 per day, etc.

FIG. 5 illustrates a portion of an automobile 500 that may be part of a wellness monitoring system, such as the wellness monitoring system 300 of FIG. 3. The automobile 500 includes seats 502A, 502B (collectively 502) having a plurality of seat sensors 504 coupled thereto. In some implementations, the seat sensors 504 may be embedded in the upholstery of the seats 502 beneath the surface of the seats. The seat sensors 504 may be operative to measure one or more of pressure, temperature or motion of an individual seated in seats 502.

The seat sensors 504 may be coupled by a wired connection 506 or by a wireless connection to a data collector device 508 which may include one or more processors 510. The one or more processors 510 may be operatively coupled to a wireless transceiver 512 and an antenna 514 which may be used to transmit sensor data from the seat sensors 504 to a remote device, such as a smartphone or a server (e.g., control subsystem 302 of FIG. 3).

The data collector device 508 may provide communication via one or more communications channels, for instance one or more wired or wireless networks, Bluetooth® channels, USB® channels, infrared channels, etc. The data collector device 508 may also include an I/O interface, such as a touchscreen, which allows an individual the ability to receive prompts from the control subsystem 302 and to input responses to the prompts.

FIG. 6 illustrates an individual 600 that is wearing a plurality of "body worn" sensors 602A-602G (collectively 602). Each of the body worn sensors 602 may be operative to sense or detect one or more of body temperature, body weight, heart rate or a heart rate characteristic (e.g., HR variability), a level of blood oxygen, a characteristic of a respiratory cycle, or a brainwave pattern. Each of the body worn sensors 602 may also include one or more biometric sensors that measure blood pressure, motion, activity levels (e.g., walking steps per day), nutrient intake, EKG, perspiration, sleep phase, sleep length, BMI, or other biometric parameters.

The body worn sensors 602 may include wearable body sensors such as a headband body sensor 602A, eyeglasses body sensor 602B, wristband body sensors 602C, belt body sensor 602D, orthotic insert body sensor 602E, and a clothing or garment embedded body sensor 602F. The body worn sensors may include sensors that are positioned (e.g., implanted, ingested) inside the individual's body, such as an ingestible body sensor 602G. The body worn sensors 602 may be surface-mounted on the individual's body in a fixed position using suitable attachment such as an adhesive. Wearable body sensors may be carried in different positions, in clothes pockets, by hand or in various bags. Generally, dependent on the biometric data sensed, body worn sensors may be positioned anywhere on, in, or near an individual so long as the desired data may be collected.

As shown in the depiction of the clothing or garment embedded body sensor 602F, each of the body worn sensors 602 may include a communications interface 604 that facilitates wired or wireless communications between a respective body worn sensor and one or more external devices. In some implementations, the body worn sensors 602 may communicate with a central unit or device 606, such as a smartphone associated with the individual 600. In some implementations, the central unit or device 606 is a device worn or otherwise carried by the individual. The central unit or device 606 may act as a data hub or data gateway, and may provide a user interface to view and manage applications in-situ. The body worn sensors 602 may utilize any suitable wired or wireless communication technologies to transmit sensor data to the control subsystem 302 (FIG. 3) directly or through one or more gateway devices. Through gateway devices, such as the central unit or device 606, it is possible to use short range wired or wireless communication to connect the body worn sensors 602 to the control subsystem 302 through a network such as the Internet.

The control subsystem 302 may assess wellness based on self-reported scores, scores assigned by a reviewer or examiner, or may be partially or fully automatically generated based on one or more criteria. The scores may be reported via various user interface devices, for instance a display, keyboard, keypad, or touch panel associated with a GUI. The scores may, for instance, be entered via a Webpage user interface and communicated to the system for evaluation. The control subsystem 302, or some other processor-based system, may perform comparisons of an individual from year to year, or between different individuals. The evaluation may be compared or scored against a defined set of wellness standards in each of a number of categories or pathways.

Wellness scores may be inferred from environmental sensors and occupant-based biometrics. For example, data gathered passively or actively from devices in the habitable environment, furniture or other biometric-reading devices, can contribute to a personal wellness score that can be used to directly or indirectly control elements in the built environment including lighting, sound, HVAC or other categories previously discussed. Relevant biometrics may include any health or wellness-related measurements, including but not limited to heart rate, heart-rate variability, sleep phase, sleep length, or respiration rate, walking steps per day, body weight, or body mass index (BMI).

The control subsystem 302 may generate individual wellness reports using information collected from the sensors 304, 308 (FIG. 3), responses 312, and knowledge data source 310. The individual wellness reports may summarize a wellness of an individual occupant of one or more buildings or habitable spaces, and may provide one or more wellness scores for the individual.

The control subsystem 302 may store training data gathered from the various inputs of the wellness monitoring system. The training data or training examples may be used by a machine learning circuit of the control subsystem 302 to learn which data are predictive of beneficial health outcomes for the occupants of a building or habitable space. The machine learning circuit may be implemented by a processor or logic associated with the control subsystem 302, or by some other computing system such as the one or more server computer systems 244 (FIG. 2).

Using the actuators/transducers 336 (FIG. 3), the control subsystem 302 may dynamically adjust at least one operational parameter of at least one of the active subsystems based on at least one of the collected environmental data and the collected personal wellness data. For example, the control subsystem 302 may dynamically change a setting for air temperature, relative humidity, illumination, scent dispersal, or other operational parameter. The change(s) may be stored for use on another occasion or for use with another habitable environment 400 (FIG. 4). Thus, the control subsystem 302 or a portion of the wellness monitoring system 300 may generate a new program, or execute an existing program with new or modified parameters, hence, in effect, constituting a new program. The control subsystem 302, or a portion of the wellness monitoring system 300, accordingly runs the new program with new parameters to provide environmental characteristics. Execution of the new program causes the various subsystems to provide the environmental characteristics or amenities in the habitable environment 400 (FIG. 4) in accordance with the new operational parameters.

To determine the dynamic adjustment to the at least one operational parameter of at least one of the active subsystems, the control subsystem 302 may evaluate or analyze the collected habitable space wellness data and/or the collected personal wellness data to provide dynamic feedback and personalized control of the environment of the habitable space 400 for the occupant. Generally, the control subsystem 202 may be operable to determine or predict operational parameters that are more optimally performing and tailored to specific occupants of the habitable space 400. Moreover, the control subsystem 402 may be operable to predict beneficial health outcomes for the occupant of the habitable space by evaluating the collected habitable space wellness data and/or the collected personal wellness data.

In addition to adjusting operational parameters of the active subsystems, the control subsystem 302 may provide informational feedback to the occupant after evaluating at least one of the personal wellness data and the habitable space wellness data. The information may be provided to the occupant using one or more in-room user operable input/output (I/O) controls, panels or kiosks 283, or using other user interfaces (e.g., an application executable on a user computing device). The in-room I/O control(s), panel(s) or kiosk(s) 283 may include a touch-sensitive or touch-responsive display, which allows presentation of information and a graphical user interface (GUI). For example, the control subsystem 302 may collect data relating to the occupant's nutrition intake, activity levels, and sleep quality. The control subsystem 302 may identify that the occupant has a higher sleep quality when the occupant is particularly active or eats certain foods. This information may be provided to the occupant (e.g., through the I/O controls, panels or kiosks 283) so the occupant may adjust his behavior accordingly. The control subsystem 302 may evaluate a large set of personal wellness data and habitable space wellness data from numerous input sources to identify patterns that may not otherwise be recognized.

Generally, by incorporating sensors, detectors, and other information feedback into the control subsystem 302, the control subsystem may utilize machine learning circuits or algorithms to allow it to conduct experimentation to find new modes of optimization. The machine learning circuit enables the control subsystem 302 to learn which data are most predictive of beneficial health outcomes for the occupants of a building, creating new ways to fine-tune the wellness monitoring system 300 beyond control programs that may be pre-programmed into the system.

Figure 7:
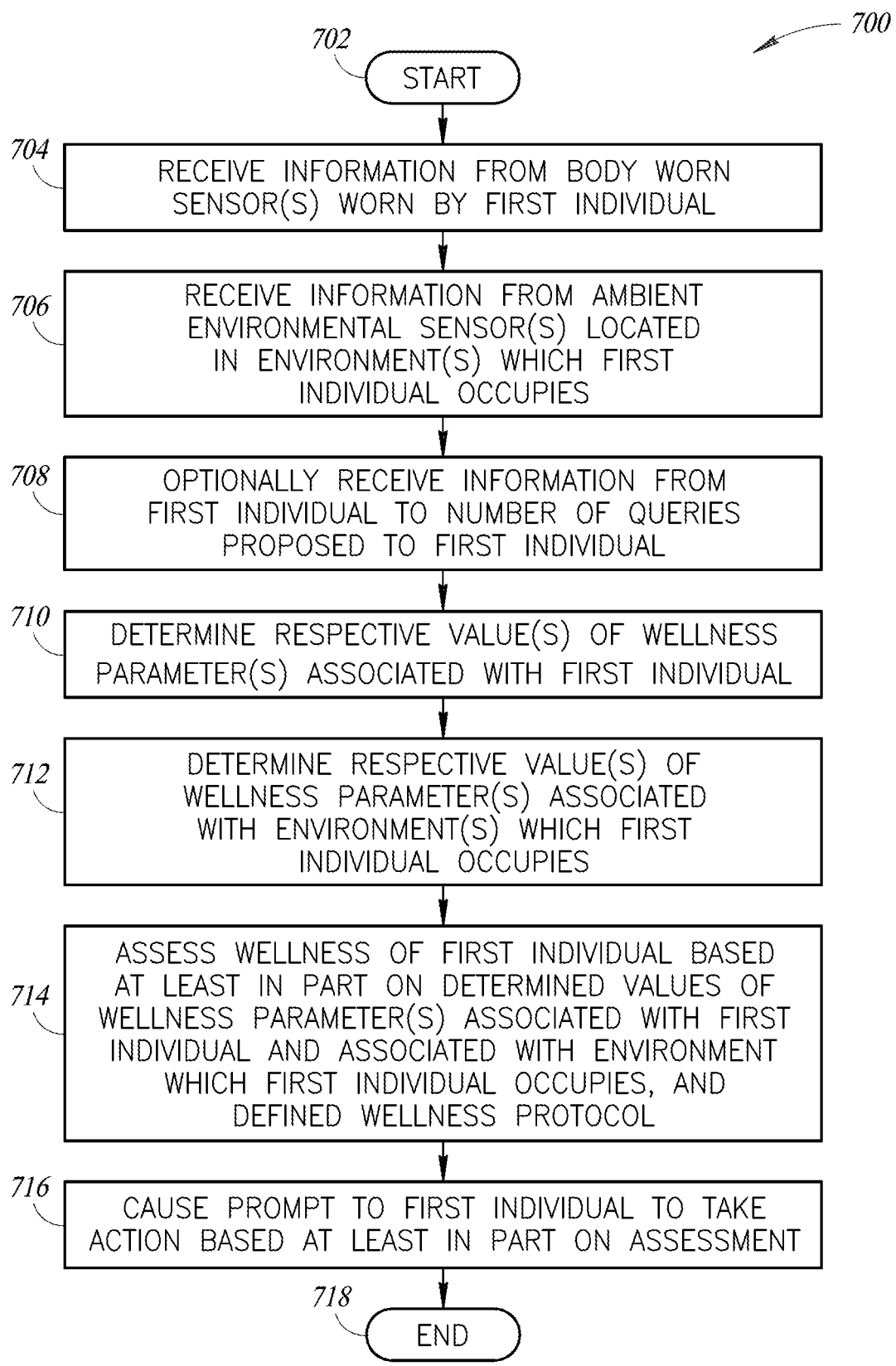
FIG. 7 is a flow diagram that shows a method of operation for a wellness monitoring system to prompt an individual to take action based on a wellness assessment, according to one illustrated embodiment.

FIG. 7 shows a method 700 of operation in a wellness monitoring system, according one illustrated embodiment.

The wellness monitoring system may include one or more processors, for example one or more microprocessors, digital signal processors, graphic processing units, field programmable gate arrays or application specific integrated circuits, or other controllers, and may include one or more central processing units and/or cores and registers. The wellness monitoring system may include one or more computer- or processor-readable media communicatively coupled to the one or more processors. The one or more computer- or processor-readable media store at least one of processor-executable instructions and/or data.

The wellness monitoring system may track wellness information for one or more individuals over time, and across one or more different environments. For example, the wellness monitoring system may track wellness information for a first individual across one, two or more different environments. The environments may, for example, include one or more residential environments, one or more work environments, one or more exercise environments, and/or one or more other environments for instance a spa, clinic or studio (e.g., yoga studio) environment and/or a vehicle environment (e.g., automobile, aircraft). The wellness monitoring system may track wellness information for one or more individuals using body worn sensors or transducers and/or environmental sensors or transducers. The wellness monitoring system may assess wellness for one or more individuals based on the tracked wellness information, for example, assessing such based on time, place or location, and/or in light of one or more defined wellness protocols.

The method 700 may start at 702. For example, the method 700 may start in response to a powering on of the wellness monitoring system, a call from a boot routine, or call from some other routine or set of processor-executable instructions, or receipt of a signal. The method 700 may be performed separately for each of a plurality of individuals and for each of one or more environments.

At 704, the processor(s) of the wellness monitoring system receives information from a number of body worn sensor(s) worn by at least a first individual. For example, the processor(s) of the wellness monitoring system may receive information representative of at least one of a bodily temperature, heart rate, bodily level of oxygen, amount of perspiration, electrocardiographic, amount of bodily activity, glucose level, blood pressure, weight, bodily alcohol level, amount of sleep, and/or level of sleep. The information may be received from a number of sensors or transducers, for example via one or more communications channels, for instance one or more wired or wireless networks, Bluetooth® channels, USB® channels, infrared channels, etc. The sensors or transducers may take a variety of forms, wearable by the first individual. For example, sensors may be integrated into armbands, smart watches, clothing, adhesive patches (e.g., EKG electrodes), headwear including hats or eyewear, or shoes or orthotics for shoes.

At 706, the processor(s) of the wellness monitoring system receives information from a number of environmental sensors located in each of a number of environments which the first individual occupies, inhabits or frequents. For example, the processor(s) of the wellness monitoring system may receive information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment. The information may be received from a number of sensors or transducers, for example via one or more communications channels, for instance one or more wired or wireless networks, Bluetooth® channels, USB Channels®, infrared channels, etc. The sensors or transducers may take a variety of forms, fixed or moveable in the environment or environments which the first individual occupies or frequents. For example, sensors may be integrated into the environments, for instance attached to or carried by walls, ceilings, furniture, flooring, etc.

Optionally at 708, the processor(s) of the wellness monitoring system may receive information in the form of responses from the first individual to a number of queries proposed to the first individual. Such may, for example, be entered via a user interface, for instance a keyboard, keypad, virtual keyboard, virtual keypad, touch interface, or microphone with associated speech recognition software. Responses may be in response to specific queries, for instance queries presented either individually or as part of a questionnaire. Queries may take a large variety of forms. Queries may be closed questions requiring yes/no responses or a selection from a list of proposed choices for response. Queries may be opened questions, allowing essentially free-form answers. Queries may solicit self-assessed values for various wellness related parameters, some or all of which may be difficult to objectively measure via sensors or transducers. For example, queries may be related to eating habits, drinking habits, sleeping habits, physical or mental wellness or well-being, schedules, levels of stress, and/or social interactions. Reported parameters may, for example, include: number of years smoking or since quitting smoking, number of alcoholic drinks per week and/or type of alcoholic drinks, level and type of drug use, whether such use is legal or illegal, family health history, own health history, or nutrition and dietary habits.

At 710, the processor(s) of the wellness monitoring system determines respective values of one or preferably more wellness parameters associated with first individual. The wellness monitoring system may determine respective values based on the received information, for example information received from body worn sensors, responses to queries, and optionally from environmental sensors or transducers. Some wellness parameters may map one-to-one with sensed parameters, for instance blood pressure, while other wellness parameters may be derived from one or more sensed parameters, for instance level of activity, weight, or eating and drinking habits.

At 712, the processor(s) of the wellness monitoring system determines respective values of one or preferably more wellness parameters associated with the one or preferably more environments which the first individual occupies or inhabits from time to time. The wellness monitoring system may determine respective values based on the received information, for example information received from environmental sensors or transducers, responses to queries, and optionally from body worn sensors. As noted above, some wellness parameters may map one-to-one with sensed parameters, while other wellness parameters may be derived from one or more sensed parameters. The number of environments and/or types of environments may vary. In some instances, only a small number of environments in which the individual spends most of their time may be monitored and/or assessed. Some environments may have an effect on wellness, either positive or negative, that is out of proportion to the relative amount of time the individual spends in that environment. Thus, in some instances, a relatively large number of environments may be tracked and assessed, including environments where the individual may spend a relatively small amount of time (e.g., clinic, studio, automobile).

At 714, the processor(s) of the wellness monitoring system assesses a wellness of the first individual based at least in part on the determined values of wellness parameters associated with first individual and/or with the determined values of wellness parameters associated with the one or more environments which the first individual occupies or frequents. The wellness protocols may be defined from a sampling and/or scientific research, and may account for a small or even a large number of parameters with a demonstrable effect on wellness. A single wellness protocol may be employed for all individuals, or respective wellness protocols may be defined for each of a number of demographic groups (e.g., gender, age bracket, shared histories of health related issues such as diabetes). In some implementations, a respective wellness protocol may even be defined on an individual-by-individual basis, for example taking into account family health history, personal health history, age, height, weight or body mass index, occupation or employment, etc. The wellness monitoring system may assess wellness for any given individual based on current and even past sensed, measured or reported parameters. As part of assessing wellness, the wellness monitoring system may determine one or more areas or parameters in which an individual is either excelling, on target, or deficient. Such may provide a basis for providing reports, suggestions, alerts, indications, notifications or other forms of prompting to the individual. For example, the wellness monitoring system may identify a pattern of weight gain which correlates to a pattern of either lack of sleep or high levels of reported stress at work and/or at home and/or during a daily commute.

At 716, the processor(s) of the wellness monitoring system causes one or more prompts to be provided to the first individual to take action based at least in part on assessment of wellness. Prompts may be laudatory, admonishing or may take other forms, for instance simple, constructive, nonjudgmental instructions identifying a corrective action. The prompts may indicate an action that the first individual may take to modify the first individual's own behavior, for example sleeping longer, exercising more, adjusting diet, avoiding situations or environments associated with physical or psychological stress. Such actions may be tailored to the specific individual. For example, the wellness monitoring system made determine that a particular environment or activity may be particular stressful to a specific individual, where the same environment or activity may not be particularly stressful to other individuals. The prompts may indicate an action the first individual may take to modify the environment, for example opening a window to increase a ratio of oxygen to carbon dioxide in an indoor environment, closing blackout curtains, installing or changing a water filter or chlorine remover to a water tap or shower, adjusting a temperature or humidity in an indoor environment. Again, the actions may be tailored to the specific individual and/or environment.

The method 700 may terminate at 718, for example until called again. Alternatively, the method 700 may repeat continually or from time to time, for example repeatedly operating as a number of respective threads in a multi-threaded system to handle multiple individuals in multiple environments.

Figure 8:
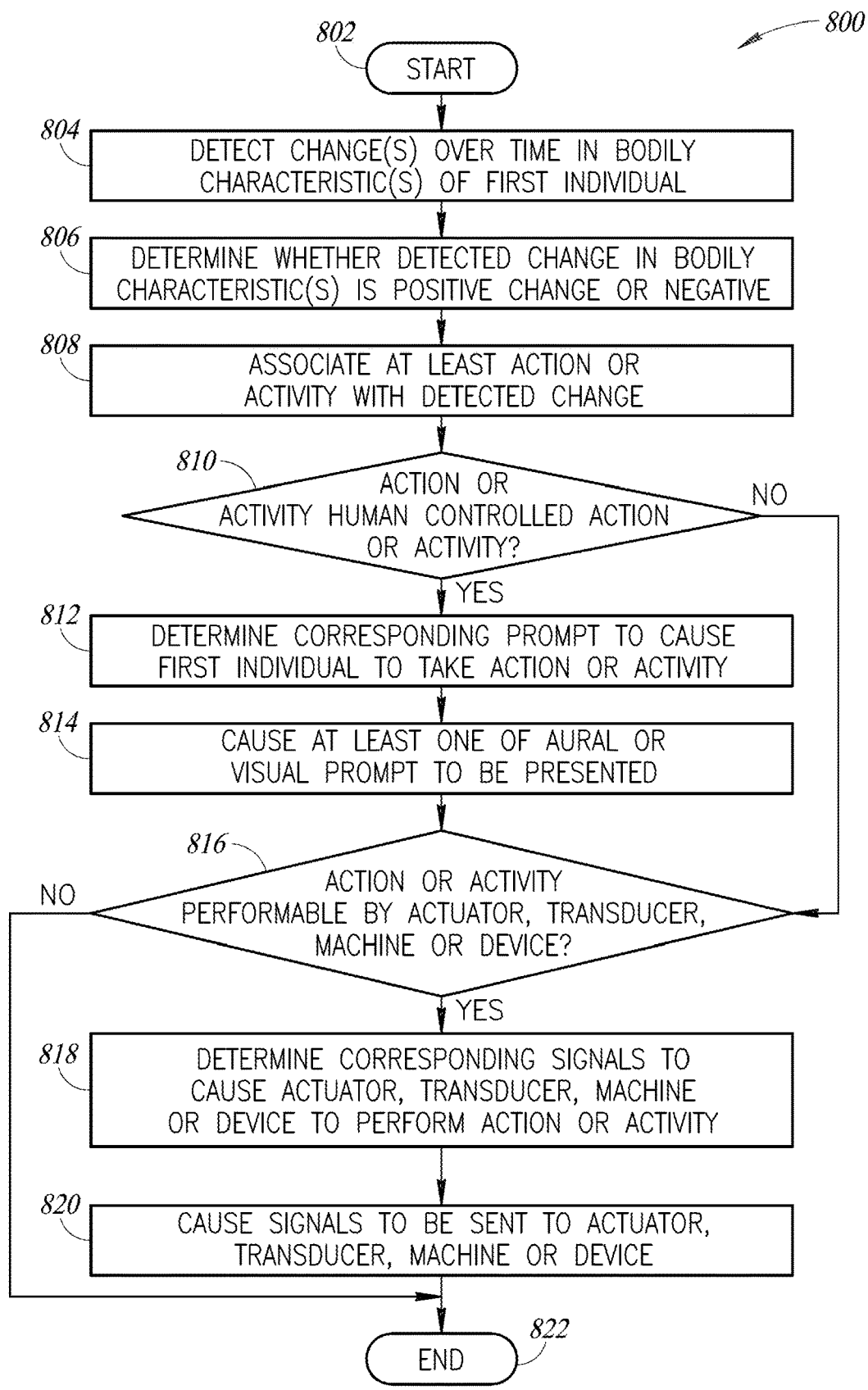
FIG. 8 is a flow diagram that shows a method of operation for a wellness monitoring system to respond to changes in wellness over time, according to one illustrated embodiment.

FIG. 8 shows a method 800 of operation in a wellness monitoring system, according one illustrated embodiment. The method 800 may be performed as part of the method 700 (FIG. 7).

The method 800 may start at 802. For example, the method 800 may start in response to a powering on of the wellness monitoring system, a call from a boot routine, or call from some other routine or set of processor-executable instructions. The method 800 may be performed separately for each of a plurality of individuals and for each of one or more environments.

At 804, the processor(s) of the wellness monitoring system detects one or more changes over time in bodily characteristic(s) of at least a first individual.

At 806, the processor(s) of the wellness monitoring system determines whether detected change over time in bodily characteristic(s) is a positive change or a negative change.

At 808, the processor(s) of the wellness monitoring system associates at least one action or activity with the detected change over time. For example, the wellness monitoring system associates a remedial or corrective action with a detected change over time that is a negative change. Also for example, the wellness monitoring system associates a reinforcing action with a detected change over time that is a positive change.

At 810, the processor(s) of the wellness monitoring system determines whether the action or activity is a human controlled action or activity. If the action or activity is a human controlled action or activity, at 812 the processor(s) of the wellness monitoring system determines at least one prompt corresponding to at least one human controlled action or activity. At 814, the processor(s) of the wellness monitoring system causes at least one of an aural or a visual prompt to be presented.

At 816, the processor(s) of the wellness monitoring system determines whether the action or activity is an automated action or activity autonomously performable by an actuator, transducer, machine or device. If the action or activity is an action or activity autonomously performable by an actuator, transducer, machine or device, at 818 the at one processor of the wellness monitoring system determines a corresponding signal or signals that will cause the actuator, transducer, machine or device to perform such action or activity. At 820, the processor(s) of the wellness monitoring system causes the at least one signal to be sent to cause the at least one actuator, transducer, machine or device to autonomously perform the at least one action or activity.

The method 800 may terminate at 822, for example until called again. Alternatively, the method 800 may repeat continually or from time to time, for example repeatedly operating as a number of respective threads in a multi-threaded system to handle multiple individuals in multiple environments.

Figure 9A:
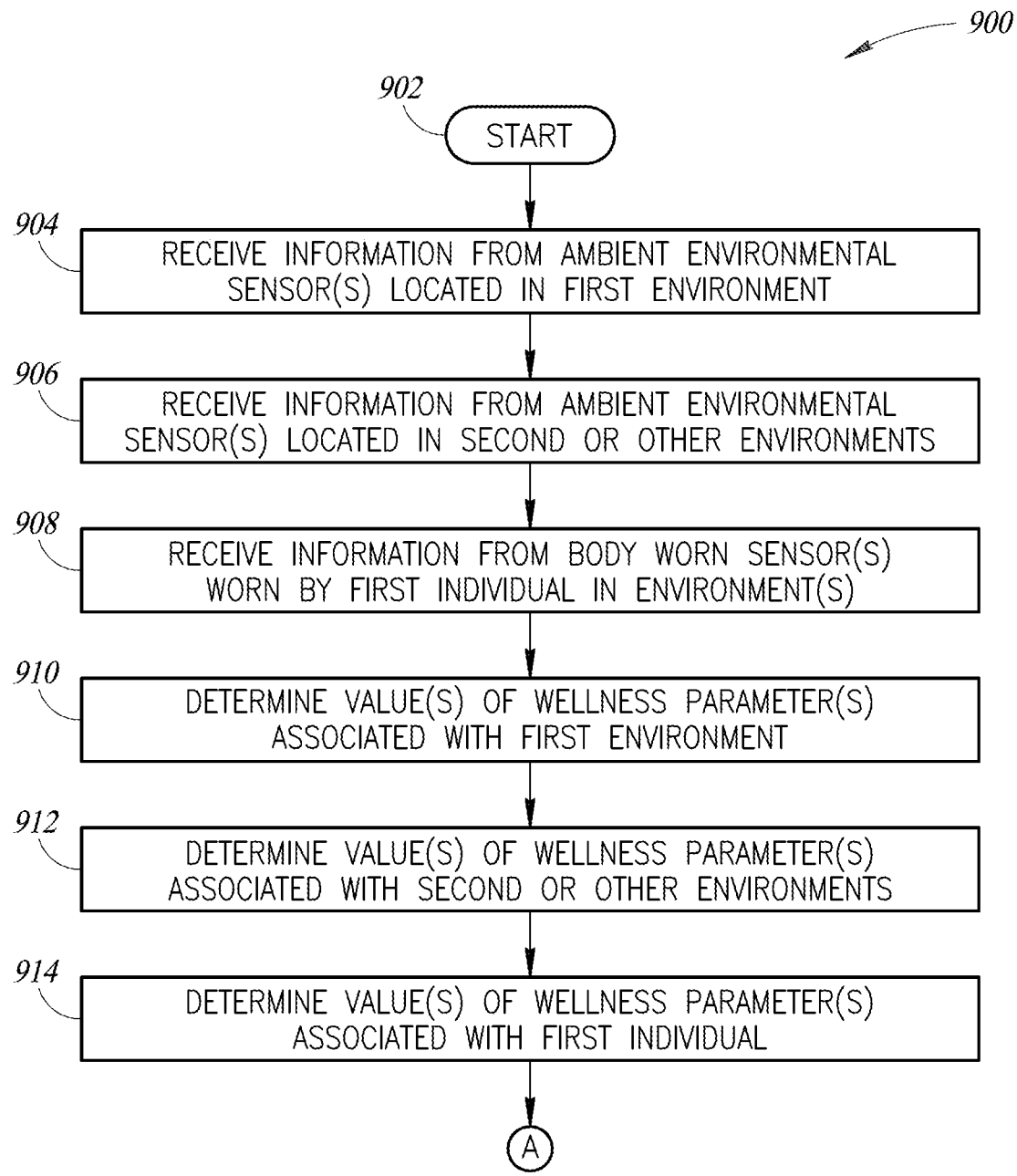
FIGS. 9A and 9B is a flow diagram that shows a method of operation for a wellness monitoring system to monitor wellness of an individual in multiple habitable environments, according to one illustrated embodiment.
Figure 9B:
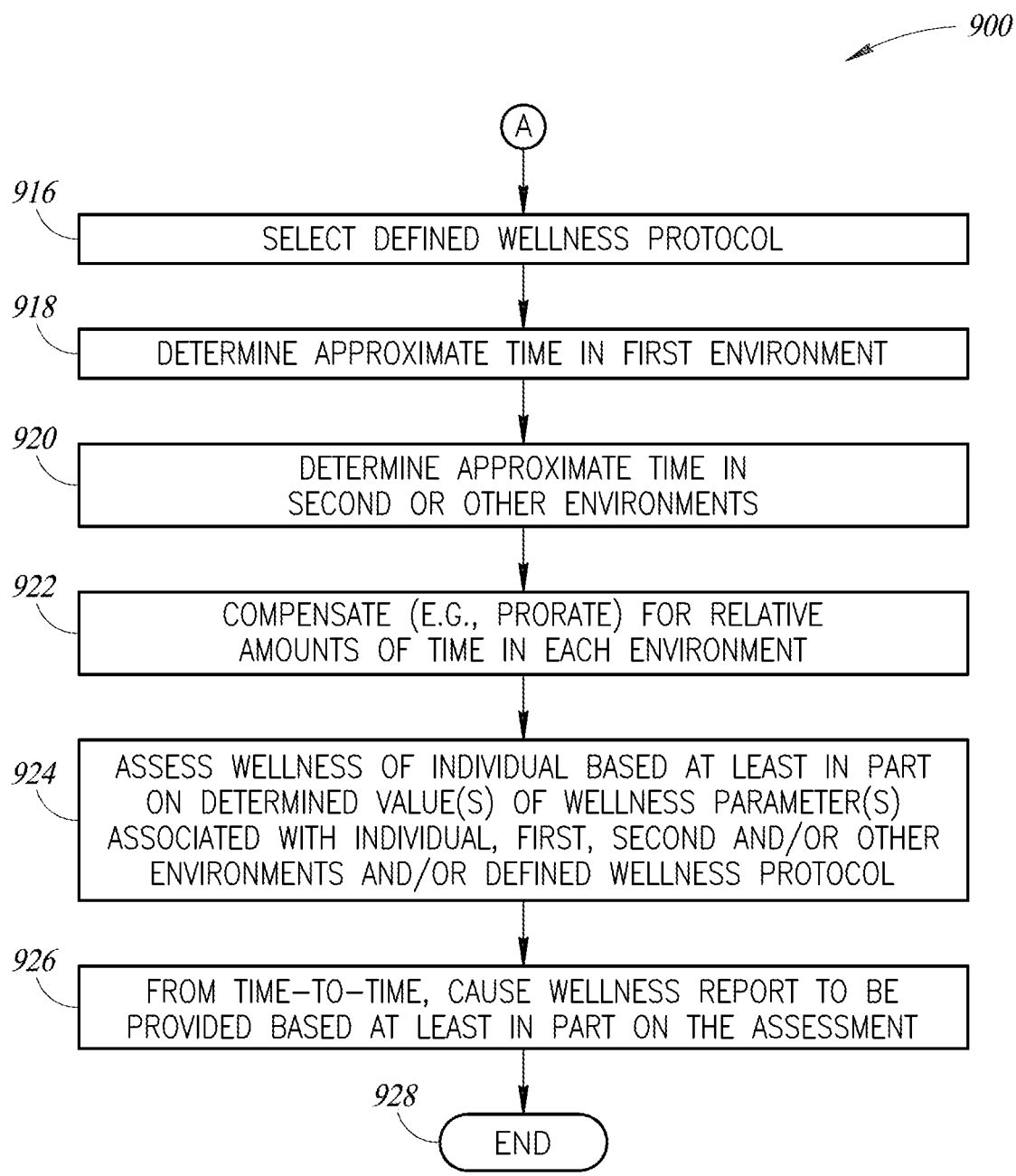

FIGS. 9A and 9B shows a method 900 of operation in a wellness monitoring system, according one illustrated embodiment.

The method 900 may start at 902. For example, the method 900 may start in response to a powering on of the wellness monitoring system, a call from a boot routine, or call from some other routine or set of processor-executable instructions. The method 900 may be performed separately for each of a plurality of individuals and for each of one or more environments.

At 904, the processor(s) of the wellness monitoring system receives information from a number of ambient environmental sensors located in at least the first environment which the first individual occupies. For example, the processor(s) may receive information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment. The first environment is a first indoor environment, for example a residential environment which the first individual occupies or inhabits.

Optionally at 906, the processor(s) of the wellness monitoring system receives information from a number of ambient environmental sensors located in at least a second environment which the first individual occupies, the second environment different from the first environment. The second environment may be a second indoor environment, for example a work environment which the first individual inhabits. The processor(s) of the wellness monitoring system may additionally or alternatively receive information from a number of ambient environmental sensors located in other environments, for example a location in which the first individual exercises such as a gymnasium or yoga studio, or a vehicle such as an automobile.

Optionally at 908, the processor(s) of the wellness monitoring system receives information from a number of body worn sensors worn by the first individual. The first individual may wear the body worn sensors in the first environment and/or in the second environment, or in other environments. The first individual may wear some of the body worn sensors only in specific environments, while wearing other ones of the body worn sensors in two or more different environments or in most or even all environments. For instance, some body worn sensors may be specific to detecting sleep related bodily characteristics, so may only be worn in sleeping environments such as bedrooms in a home, hotel, motel, other place of hospitality, or in a clinical setting such as a sleep clinic. Also for instance, some of the body worn sensors may be applicable to a large number of environments, for example a pulse sensor, pulse oximetry sensor, etc. The information may, for example, include information representative of at least one of a bodily temperature, a heart rate, a bodily level of oxygen, an amount of perspiration, an electrocardiograph, an amount of bodily activity, a glucose level, a blood pressure, bodily alcohol level, an amount of sleep, or a level of sleep.

At 910, the processor(s) of the wellness monitoring system repeatedly determines respective value(s) of wellness parameter(s) associated with the first environment which the first individual occupies, inhabits or frequents. For example, the processor(s) of the wellness monitoring system may determine a respective value of at least one wellness parameter associated with at least the first environment which the first individual occupies from the received information from the number of ambient environmental sensors located in at least the first environment. Also for example, the processor(s) of the wellness monitoring system may determine a respective value of at least one wellness parameter associated with at least the first individual from the received information from the number of body worn sensors worn by the first individual.

Optionally at 912, the processor(s) of the wellness monitoring system repeatedly determines a respective value of at least one wellness parameter associated with a second environment which the first individual occupies, inhabits or frequents.

At 914, the processor(s) of the wellness monitoring system repeatedly determines respective value(s) of wellness parameter(s) associated with first individual. For example, the processor(s) of the wellness monitoring system may determine a respective value of at least one wellness parameter associated with at least the first environment which the first individual occupies from the received information from the number of ambient environmental sensors located in at least the first environment, the second environment, and or other environments which the first individual occupies from time to time. For example, the processor(s) of the wellness monitoring system may determine a respective value of at least one wellness parameter associated with the first individual includes determining the respective values of at least one wellness parameter associated with the first individual while the first individual occupies the second environment.

At 916, the processor(s) of the wellness monitoring system optionally selects one or more defined wellness protocols.

At 918, the processor(s) of the wellness monitoring system optionally determines at least an approximation of time the first individual spends in the first environment. At 920, the processor(s) of the wellness monitoring system optionally determines at least an approximation of time the first individual spends in the at least the second, and possible other environments. At 922, the processor(s) of the wellness monitoring system optionally compensates for the relative amounts of time the first individual spends in each of the environments. For example, the processor(s) may prorate at least one environmental exposure measurement based on a relative amount of time that first individual occupies each environment.

At 924, the processor(s) of the wellness monitoring system assesses wellness of first individual based at least in part on determined respective value(s) of wellness parameter(s) associated with first individual and associated with first environment. The processor(s) of the wellness monitoring system may assess wellness of the first individual based at least in part on the determined respective values of the at least one wellness parameter associated with the first individual and the determined respective values of the at least one wellness parameter associated with the first environment and the second environment which the first individual occupies. The assessment may be based in part on a defined wellness protocol.

At 926, the processor(s) of the wellness monitoring system, from time to time, cause a wellness report to be provided based at least in part on the assessment. For example, the processor(s) causes a wellness dashboard to be provided. Additionally or alternatively, the processor(s) causes a transmission of an electronic message with an electronic copy of the wellness report attached, or with a hyperlink to an electronic copy of the wellness report attached.

The method 900 may terminate at 928, for example until called again. Alternatively, the method 900 may repeat continually or from time to time, for example repeatedly operating as a number of respective threads in a multi-threaded system to handle multiple individuals in multiple environments.

Figure 10:
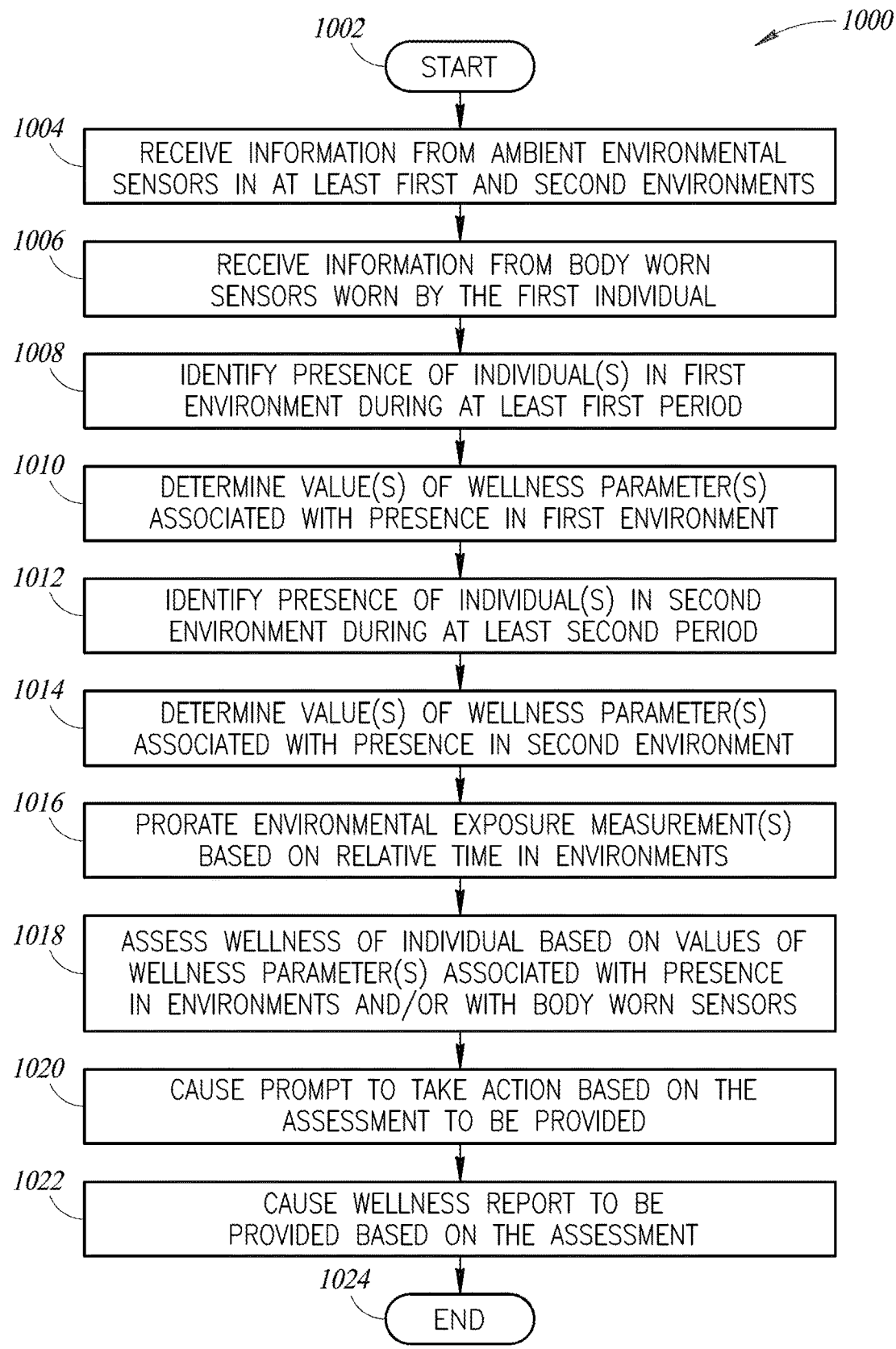
FIG. 10 is a flow diagram that shows a method of operation for a wellness monitoring system to monitor wellness of an individual and generate a wellness report, according to one illustrated embodiment.

FIG. 10 shows a method 1000 of operation in a wellness monitoring system, according one illustrated embodiment.

The method 1000 may start at 1002. For example, the method 1000 may start in response to a powering on of the wellness monitoring system, a call from a boot routine, or a call from some other routine or set of processor-executable instructions. The method 1000 may be performed separately for each of a plurality of individuals and for each of one or more environments.

At 1004, the processor(s) of the wellness monitoring system receives information from a number of ambient environmental sensors located in respective ones of at least a first environment and a second environment which the first individual occupies, inhabits or frequents. For example, the processor(s) of the wellness monitoring system may receive information representative of at least one of a room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment. The information may be received from a number of sensors or transducers, for example via one or more communications channels, for instance one or more wired or wireless networks, Bluetooth® channels, USB® channels, infrared channels, etc. The sensors or transducers may take a variety of forms, fixed or moveable in the environment or environments which the first individual frequents. For example, sensors may be integrated into the environments, for instance attached to or carried by walls, ceilings, furniture, flooring, etc.

At 1006, the processor(s) of the wellness monitoring system receives information from a number of body worn sensor(s) worn by at least a first individual. For example, the processor(s) of the wellness monitoring system may receive information representative of at least one of a bodily temperature, heart rate, bodily level of oxygen, amount of perspiration, electrocardiographic, amount of bodily activity, glucose level, blood pressure, weight, bodily alcohol level, amount of sleep, and/or level of sleep. The information may be received from a number of sensors or transducers, for example via one or more communications channels, for instance one or more wired or wireless networks, Bluetooth® channels, USB® channels, infrared channels, etc. The sensors or transducers may take a variety of forms, wearable by the first individual. For example, sensors may be integrated into armbands, smart watches, clothing, adhesive patches (e.g., EKG electrodes), headwear including hats or eyewear, shoes or orthotics for shoes.

At 1008, the processor(s) of the wellness monitoring system identifies a presence of at least a first individual in a first environment during at least a first period. In many implementations, any given environment may have one, two or more individuals during any given period of time. Thus, the processor(s) of the wellness monitoring system may often identify a presence of a second, third or other individual in the first environment, either during the first period, or during other periods of time which may overlap or not overlap with the first period. A variety of devices and approaches may be used to identify the presence of specific individuals in a given environment. For any given implementation, the same devices and approaches may be used for each environment, or different devices and approaches may be used for different ones of the environments. The processor(s) of the wellness monitoring system may, for example, receive signals from one or more sensors located in the various embodiments, for instance motion sensors, or sensors that detect a turning on/turning off of lights or opening of a door. Additionally or alternatively, the processor(s) of the wellness monitoring system may, for example, receive signals via one or more antennas, transmitted from one or more transponders. The transponders, for instance wireless transponders, may be worn by, or be otherwise physically associated with, respective ones of the individuals. The wireless transponders may take a variety of forms, for example radio frequency identification (RFID) transponders. The transponders may, for example, take the form of smartphones or other processor-based devices with wireless transmitters or transceivers that emit identifying information (e.g., MAC address, network address). Each transponder stores and transmits a unique identifier. Individuals to be monitored for wellness may be uniquely associated with the unique identifier of one or more transponders. Alternatively or additionally, some environments may be generally inhabited by a single individual. In such environments, simple detection of the presence or absence of a person may be treated as detection of the presence or absence of a specific individual.

At 1010, the processor(s) of the wellness monitoring system determines a value of at least one wellness parameter associated with the presence during the first period of the first individual in the first environment. For example, the processor(s) of the wellness monitoring system may determine a respective value of at least one wellness parameter associated with at least the first environment which the first individual occupies during at least the first period from the received information from the number of ambient environmental sensors located in at least the first environment. Also for example, the processor(s) of the wellness monitoring system may determine a respective value of at least one wellness parameter associated with at least the first individual from the received information from the number of body worn sensors worn by the first individual during periods when the first individual is in the first environment. Likewise, the processor(s) of the wellness monitoring system determine a value of at least one wellness parameter associated with the presence of a second or other individuals in the first environment, during the first period and/or during other periods.

At 1012, the processor(s) of the wellness monitoring system identifies a presence of the first individual in a second environment during at least a second period, the second environment different from (e.g., remote from) the first environment, the second period different from the first period.

At 1014, the processor(s) of the wellness monitoring system determines a value of at least one wellness parameter associated with the presence during the second period of the first individual in the second environment. For example, the processor(s) of the wellness monitoring system may determine a respective value of at least one wellness parameter associated with at least the second environment which the first individual occupies during at least the second period from the received information from the number of ambient environmental sensors located in at least the second environment. Also for example, the processor(s) of the wellness monitoring system may determine a respective value of at least one wellness parameter associated with at least the first individual from the received information from the number of body worn sensors worn by the first individual during periods when the first individual is in the second environment. Likewise, the processor(s) of the wellness monitoring system determines a value of at least one wellness parameter associated with the presence of a second, third or other individuals in the second or other environments, during the second period and/or during other periods.

Optionally at 1016, the processor(s) of the wellness monitoring system prorates at least one environmental exposure measurement based on a relative amount of time that the first individual occupies each of at least the first and the second environments.

At 1018, the processor(s) of the wellness monitoring system assesses a wellness of at least the first individual based at least in part on the determined values of the at least one wellness parameter associated with the presence during at least the first and the second periods of the first individual in the first and the second environments, respectively. Likewise, the processor(s) of the wellness monitoring system may assess a wellness of at least a second individual based at least in part on the determined values of the at least one wellness parameter associated with the presence of the second individual in the first, the second, and/or other environments. The processor(s) of the wellness monitoring system assesses wellness based on one or more defined wellness protocols. As discussed above in reference to method 1000 (FIG. 10), the wellness monitoring system may employ a single wellness protocol for all individuals, respective wellness protocols for various demographic groups or groups of similar situated individuals, and/or even employ wellness protocols which are specific to specific individuals. Assessing wellness may, for example, include detecting changes in bodily characteristics over time, for example as described in method 800 (FIG. 8).

At 1020, the processor(s) of the wellness monitoring system causes a prompt to take an action based at least in part on the assessment to be provided to the first individual.

At 1022, the processor(s) of the wellness monitoring system from time to time causes a wellness report to be provided based at least in part on the assessment. The method 1000 may terminate at 1024, for example until called again.

Alternatively, the method 1000 may repeat continually or from time to time, for example repeatedly operating as a number of respective threads in a multi-threaded system to handle multiple individuals in multiple environments.

Figure 11:
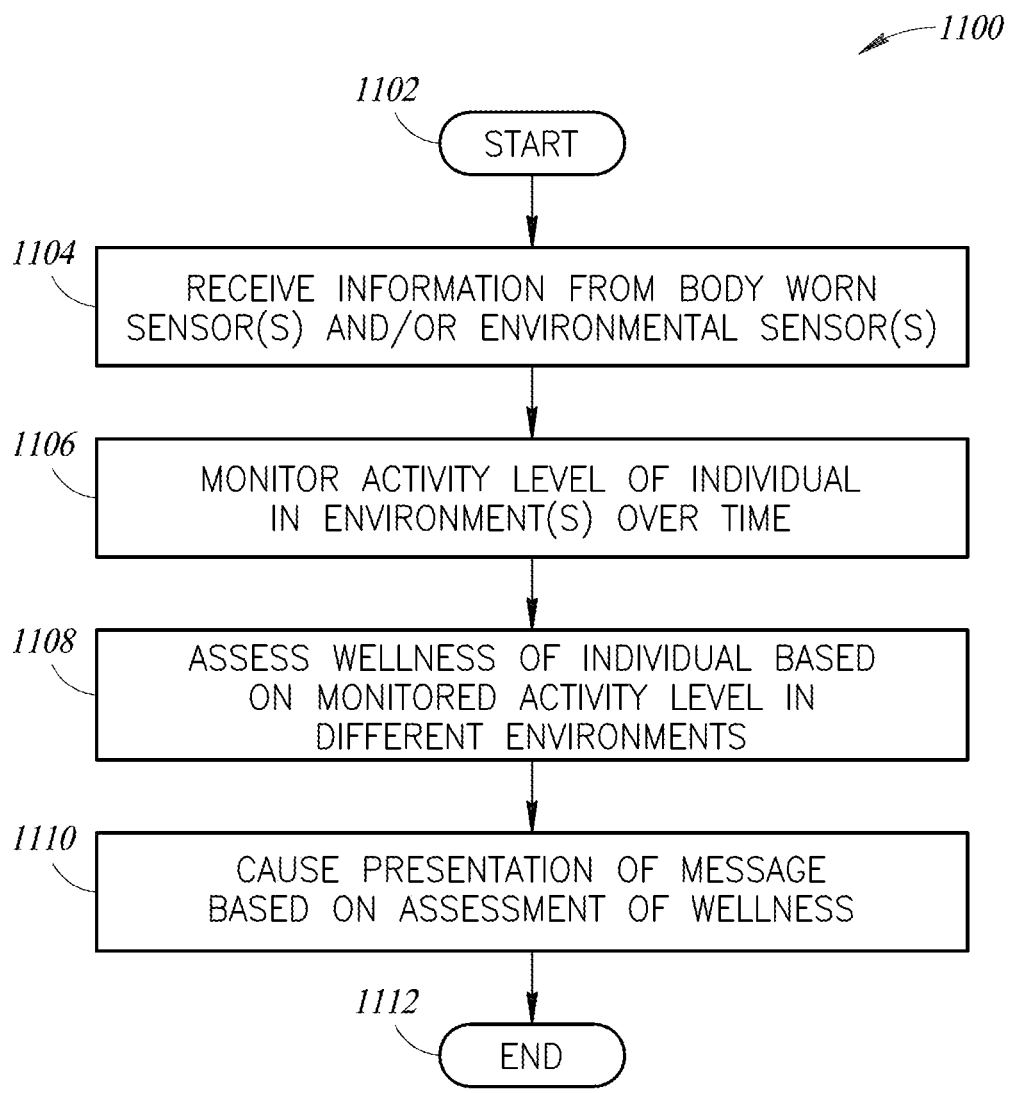
FIG. 11 is a flow diagram that shows a method of operation for a wellness monitoring system to monitor wellness of an individual based on monitored activity levels of the individual in multiple environments, according to one illustrated embodiment.

FIG. 11 shows a method 1100 of operation in a wellness monitoring system, according one illustrated embodiment.

The method 1100 may start at 1102. For example, the method 1100 may start in response to a powering on of the wellness monitoring system, a call from a boot routine, or call from some other routine or set of processor-executable instructions. The method 1100 may be performed separately for each of a plurality of individuals and for each of one or more environments.

At 1104, the processor(s) of the wellness monitoring system receives information from at least one of a number of body worn sensors worn by the first individual, or a number of environmental sensors. The processor(s) of the wellness monitoring system receives, for example, the information from a residential environment, a business environment, and a vehicle environment. The processor(s) of the wellness monitoring system may, for example, receive information from at least one motion sensor or accelerometer worn by the first individual. The processor(s) of the wellness monitoring system may, for example, receive information from at least one pressure sensor located in at least one shoe worn by the first individual, for instance in an orthotic. The processor(s) of the wellness monitoring system may, for example, receive information from at least one of a number of sensors in at least one of a chair, a sofa, a bed, or a seat in a vehicle. The processor(s) of the wellness monitoring system may, for example, receive location specific information, for instance from at least one global position transceiver or wireless communications transceiver.

At 1106, the processor(s) of the wellness monitoring system monitors a level of activity of a first individual in each of at least two environments over a period of time, a first one of the environments different from a second one of the environments. Monitoring the level of activity of a first individual in each of at least two environments over a period of time may, for example, include combining information received from both body worn sensors and environmental sensors. The processor(s) of the wellness monitoring system may determine the level of activity on a basis of a time and a location based on the received information. The processor(s) of the wellness monitoring system may identify a pattern in the determined level of activity based on the time and the location.

At 1108, the processor(s) of the wellness monitoring system assesses a wellness of the first individual based at least in part on the monitored level of activity of the first individual in the at least two different environments. The processor(s) of the wellness monitoring assesses a wellness of the first individual based one at least one defined wellness protocol.

At 1110, the processor(s) of the wellness monitoring system causes at least one message to be presented to the first individual based on the assessment of wellness of the first individual. For example, the processor(s) of the wellness monitoring system may cause an alert to be provided in response to an out of threshold condition. Additionally or alternatively, the processor(s) of the wellness monitoring system may, for example, cause a suggestion for improving or maintaining a wellness to be provided.

The method 1100 may terminate at 1112, for example until called again. Alternatively, the method 1100 may repeat continually or from time to time, for example repeatedly operating as a number of respective threads in a multi-threaded system to handle multiple individuals in multiple environments.

A habitable environment may include any combination of one or more of the passive or active components. Some components may reside in, or be controlled as part of a different subsystems than illustrated.

Also for instance, while various methods and/or algorithms have been described, some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays or programmable logic circuits (PLCs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other non-transitory computer-readable storage media.

U.S. provisional patent application Ser. No. 62/102,963, filed Jan. 13, 2015, and U.S. provisional patent application Ser. No. 61/694,125, filed Aug. 28, 2012, and U.S. patent application Ser. No. 14/012,444, filed Aug. 28, 2013, are incorporated herein by reference in their entireties. PCT patent application Serial No. PCT/US13/57070, filed Aug. 28, 2013, is incorporated herein by reference in its entirety. U.S. provisional patent application Ser. No. 61/946,159, filed Feb. 28, 2014, is incorporated herein by reference in its entirety. The various embodiments described above can be combined to provide further embodiments. Aspects of the embodiments can be modified, if necessary or desirable to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation in a wellness monitoring system which includes at least one processor, a plurality of body worn sensors, and a plurality of ambient environmental sensors, and at least one nontransitory processor-readable medium which stores at least one of processor-executable instructions or data communicatively coupled to the at least one processor, the method comprising: sensing biometric data by at least one body worn sensor integrated into an armband worn by a first individual, wherein the at least one body worn sensor is communicatively coupled to the at least one processor and is configured to transmit the biometric data to the at least one processor; repeatedly determining by the at least one processor a respective value of at least one wellness parameter associated with the first individual from the biometric data; sensing environmental data by at least one ambient environmental sensor located in an environment which the first individual occupies, wherein the at least one ambient environmental sensor is communicatively coupled to the at least one processor and is configured to transmit environmental data to the at least one processor; repeatedly determining by the at least one processor a respective value of at least one wellness parameter associated with the environment which the first individual occupies from the environmental data; autonomously tracking over time the at least one wellness parameter associated with the first individual; assessing a wellness of the first individual by the at least one processor by comparing the determined value of the at least one wellness parameter associated with the first individual to a target range for the at least one wellness parameter defined in a wellness protocol; and upon determining the at least one wellness parameter associated with first individual is outside the target range, identifying at least one wellness parameter associated with the environment corresponding with the at least one wellness parameter associated with the first individual that is outside the target range, and automatically causing by the at least one processor, a transmission of an electronic message to an electronic device associated with the first individual and configured to display the electronic message, the electronic message prompting the first individual to take an action based at least in part on the assessment and the identified at least one wellness parameter associated with the environment; upon determining the at least one wellness parameter associated with first individual is outside the target range, causing at least one actuator to dynamically adjust at least one operational parameter of at least one active subsystem in the wellness monitoring system based at least in part on the assessment and the identified at least one wellness parameter associated with the environment.

2. The method of claim 1, wherein the biometric data maps one-to-one with the respective value of the at least one wellness parameter associated with the first individual.

3. The method of claim 1, wherein the environmental data sensed by the at least one ambient environmental sensor located in the environment which the first individual occupies includes at least one of room temperature in the environment, a level of light in the environment, a spectral distribution of light in the environment, an amount of noise in the environment, a measure of air quality in the environment, a measure of water quality in the environment, or a measure of pressure asserted by at least a portion of the first individual on at least one of a piece of furniture or flooring in the environment.

4. The method of claim 1, further comprising:
receiving information in the form of responses from the first individual to a number of queries proposed to the first individual.

5. The method of claim 4 wherein determining a respective value of at least one wellness parameter associated with the first individual includes determining the respective value of at least one wellness parameter associated with the first individual based on at least one of the responses from the first individual.

6. The method of claim 4 wherein determining a respective value of at least one wellness parameter associated with an environment which the first individual occupies includes determining the respective value of at least one wellness parameter associated with the environment which the first individual occupies based on at least one of the responses from the first individual.

7. The method of claim 1, further comprising:
detecting a change over time in at least one bodily characteristic of the first individual;
determining whether the detected change over time in at least one bodily characteristic of the first individual is a positive change or a negative change;
associating the detected change over time with at least one action, via the at least one processor; and
causing the at least one action to be taken autonomously by at least one actuator.

8. The method of claim 1 wherein the processor prorates the at least one wellness parameter based on a relative amount of time that the first individual occupies the environment.

9. The method of claim 1 wherein the wellness protocol is defined for a demographic group selected from at least one of gender, age bracket, and shared history of health-related issues.

10. The method of claim 1 wherein the at least one ambient environmental sensor is attached to or carried by a piece of furniture in the environment.

11. The method of claim 10 wherein the piece of furniture is at least one of a chair, a sofa, a bed, or a seat in a vehicle.

12. The method of claim 4 wherein the responses from the first individual to the number of queries proposed to the first individual are captured via an automated survey presented to the first individual via a graphical user interface on the electronic device associated with the first individual.

13. The method of claim 1 wherein the electronic message includes an aural prompt.

14. The method of claim 1, wherein the at least one active subsystem includes at least one of a control subsystem, an illumination subsystem, a water treatment subsystem, an air treatment subsystem, a scent subsystem, or a sound subsystem.

15. The method of claim 1, wherein at least one operational parameter includes at least one of air temperature, relative humidity, illumination, or scent dispersal.

16. The method of claim 1, wherein the actuator adjusts at least one of an electrochromatic pane or an electric motor coupled by a transmission to drive a window covering to dynamically adjust illumination in the environment.

17. The method of claim 1 wherein the biometric data includes at least one of a bodily temperature, heart rate, bodily level of oxygen, amount of perspiration, electrocardiographic data, amount of bodily activity, glucose level, blood pressure, bodily alcohol level, amount of sleep, or sleep quality.

* * * * *